US008227408B2

(12) United States Patent
Tezapsidis

(10) Patent No.: US 8,227,408 B2
(45) Date of Patent: Jul. 24, 2012

(54) LEPTIN AS AN ANTI-AMYLOIDOGENIC BIOLOGIC AND METHODS FOR DELAYING THE ONSET AND REDUCING ALZHEIMER'S DISEASE-LIKE PATHOLOGY

(75) Inventor: Nikolaos Tezapsidis, West Orange, NJ (US)

(73) Assignee: Neurotez, Inc., Bridgewater, NJ (US)

( * ) Notice: Subject to any disclaimer, the term of this patent is extended or adjusted under 35 U.S.C. 154(b) by 1142 days.

(21) Appl. No.: 11/516,224

(22) Filed: Sep. 6, 2006

(65) Prior Publication Data

US 2007/0066527 A1 Mar. 22, 2007

Related U.S. Application Data

(60) Provisional application No. 60/714,948, filed on Sep. 7, 2005.

(51) Int. Cl.
*A61K 38/22* (2006.01)

(52) U.S. Cl. ........................ 514/5.8; 514/17.8; 514/18.2

(58) Field of Classification Search ........................ None
See application file for complete search history.

(56) References Cited

U.S. PATENT DOCUMENTS 4,105,027 A 8/1978 Lundquist
4,192,309 A 3/1980 Poulsen
4,227,522 A 10/1980 Carris
4,627,432 A 12/1986 Newell et al.
4,778,054 A 10/1988 Newell et al.
4,811,731 A 3/1989 Newell et al.
5,035,237 A 7/1991 Newell et al.
5,521,283 A 5/1996 DiMarchi et al.
5,552,522 A 9/1996 DiMarchi et al.
5,552,523 A 9/1996 Basinski et al.
5,552,524 A 9/1996 Basinski et al.
5,698,389 A 12/1997 de la Brousse
5,756,461 A 5/1998 Stephens
5,830,450 A 11/1998 Lallone
6,001,816 A 12/1999 Morsy
6,001,968 A 12/1999 Friedman et al.
6,020,004 A 2/2000 Shah
6,025,324 A 2/2000 Bailon et al.
6,025,325 A 2/2000 Campfield et al.
6,048,837 A 4/2000 Friedman
6,068,976 A 5/2000 Briggs
6,284,221 B1 * 9/2001 Schenk et al. ................ 424/9.2
6,309,853 B1 10/2001 Friedman
6,352,970 B1 3/2002 Ke
6,429,290 B1 8/2002 Friedman
6,471,956 B1 10/2002 Friedman
6,475,984 B2 11/2002 Kirwin
6,518,235 B1 2/2003 Oomura
6,630,346 B1 10/2003 Morsy
6,716,810 B1 4/2004 Brennan
6,777,388 B1 8/2004 Grasso
6,921,527 B2 7/2005 Platz et al.
6,936,439 B2 8/2005 Mann et al.
7,074,397 B1 7/2006 Matthews
7,109,159 B1 9/2006 Barkan
7,183,254 B2 2/2007 DePaoli
7,186,694 B2 3/2007 Grasso
7,208,572 B2 4/2007 Grasso
7,291,458 B2 11/2007 Broekaert
7,307,142 B2 12/2007 Gertler
7,354,896 B2 4/2008 Kirwin
7,544,492 B1 6/2009 Friedman
7,582,292 B2 9/2009 Wilkison
7,629,315 B2 12/2009 Zhao
2002/0015709 A1 2/2002 Kirwin
2002/0019351 A1 2/2002 Ke
2002/0019352 A1 2/2002 Brems
2002/0107211 A1 8/2002 Friedman
2003/0036526 A1 2/2003 Broekaert
2003/0130192 A1 7/2003 Kirwin
2003/0215423 A1 11/2003 Morsy
2004/0043932 A1 3/2004 Grasso
2004/0053366 A1 3/2004 Lo
2004/0202652 A1 10/2004 Karsenty
2004/0213763 A1 10/2004 Friedman (Continued)

FOREIGN PATENT DOCUMENTS

WO WO 91/16038 10/1991

(Continued)

OTHER PUBLICATIONS

Vickers. A vaccine against Alzheimer's disease: developments to date. Drugs Aging 2002; 19(7):487-94.*

Fewlass et al. Obesity-related leptin regulates Alzheimer's Abeta. FASEB J. Dec. 2004;18(15):1870-8.*

Farr et al. Effects of leptin on memory processing. Peptides. Jun. 2006;27(6):1420-5. Epub Nov. 15, 2005.*

Purves, Dale, et al (Eds.), Neuroscience, 2001, Sinauer Associates, Inc., 2nd Edition, pp. 403, 554, 555 and 678.*

Kotilinek et al. Reversible memory loss in a mouse transgenic model of Alzheimer's disease. J Neurosci. Aug. 1, 2002;22(15):6331-5.*

Tomas et al. Enhanced muscle fat oxidation and glucose transport by ACRP30 globular domain: acetyl-CoA carboxylase inhibition and AMP-activated protein kinase activation. Proc Natl Acad Sci U S A. Dec. 10, 2002;99(25):16309-13. Epub Nov. 27, 2002.*

Idris et al. Familial hyperinsulinaemia associated with epilepsy and mental retardation—a syndrome of familial insulin resistance. Diabet Med. Jun. 2004;21(6):628-31.*

(Continued)

*Primary Examiner* — Daniel E Kolker
*Assistant Examiner* — Gregory S Emch
(74) *Attorney, Agent, or Firm* — Beverly W. Lubit; Greenberg Traurig, LLP

(57) ABSTRACT

The present invention relates to methods for treating, preventing, or diagnosing the pathology of progressive cognitive disorders resulting from accumulation of an amyloid peptide, in particular, Alzheimer's disease, Down's syndrome and cerebral amyloid angiopathy, in mammalian subjects using a composition comprising therapeutically effective amount of a leptin, leptin mimic, leptin derivative, leptin agonist, or AMP-dependent protein kinase activator, alone, or in combination with, one or more lipolytic/antilipogenic compounds. It further relates to methods for improving cognitive function using a composition comprising a therapeutically effective amount of leptin, a leptin mimic, a leptin derivative, an AMP-dependent protein kinase activator, a leptin agonist, a leptin blocker, a mimic of a leptin blocker, a leptin antagonist, an AMP-dependent protein kinase inhibitor; or a pharmaceutically acceptable salt thereof.

26 Claims, 11 Drawing Sheets

U.S. PATENT DOCUMENTS

2005/0020496 A1 1/2005 DePaoli
2005/0049193 A1 3/2005 Grasso
2005/0065078 A1 3/2005 Cawthorne
2005/0163799 A1 7/2005 Mann et al.
2005/0250690 A1 11/2005 Gonzalez
2005/0272656 A1 12/2005 Matthews
2006/0079442 A1 4/2006 Ilan
2006/0079443 A1 4/2006 Ilan
2006/0154859 A1 7/2006 Gertler
2006/0165683 A1 7/2006 Karsenty
2006/0205660 A1 9/2006 De Sauvage
2006/0206948 A1 9/2006 Zhao
2006/0281699 A1 12/2006 Merchiers et al.
2007/0066527 A1 3/2007 Tezapsidis
2007/0099836 A1 5/2007 DePaoli
2007/0104697 A1 5/2007 Wilkison
2007/0135510 A1 6/2007 Blackburn et al.
2007/0162987 A1 7/2007 Grasso
2007/0218504 A1 9/2007 Zhao
2008/0009475 A1 1/2008 Garner et al.
2008/0108567 A1 5/2008 Grasso
2008/0118503 A1 5/2008 Strasburger
2008/0138811 A1 6/2008 Mack et al.
2008/0242612 A1 10/2008 Kirwin
2009/0029919 A1 1/2009 Gonzalez
2009/0031434 A1 1/2009 Han
2009/0175841 A1 7/2009 Berry
2009/0281522 A1 11/2009 Thio
2010/0113358 A1 5/2010 Tezapsidis

FOREIGN PATENT DOCUMENTS

WO WO 96/23513 8/1996
WO WO 96/23514 8/1996
WO WO 96/23515 8/1996
WO WO 96/23516 8/1996
WO WO 96/23517 8/1996
WO WO 96/23518 8/1996
WO WO 96/23519 8/1996
WO WO 96/23520 8/1996
WO WO9629405 9/1996
WO WO9724440 7/1997
WO WO9748419 12/1997
WO WO9748806 12/1997
WO WO9824896 6/1998
WO WO9846257 10/1998
WO WO9951253 10/1999
WO WO0009165 2/2000
WO WO0011173 3/2000
WO WO0020872 4/2000
WO WO0033658 6/2000
WO WO0040615 7/2000
WO WO0047741 8/2000
WO WO 2005110468 A2 * 11/2005

OTHER PUBLICATIONS

Smith et al. Levodopa with carbidopa diminishes glycogen concentration, glycogen synthase activity, and insulin-stimulated glucose transport in rat skeletal muscle. J Appl Physiol. Dec. 2004;97(6):2339-46. Epub Jul. 16, 2004.*

Sirtori et al. Re-evaluation of a biguanide, metformin: mechanism of action and tolerability. Pharmacol Res. Oct.-Nov. 1994;30(3):187-228.*

Chen et al. Antidiabetic drug metformin (GlucophageR) increases biogenesis of Alzheimer's amyloid peptides via up-regulating BACE1 transcription. Proc Natl Acad Sci U S A. Mar. 10, 2009;106(10):3907-12. Epub Feb. 23, 2009.*

Geldmacher et al. A randomized pilot clinical trial of the safety of pioglitazone in treatment of patients with Alzheimer disease. Arch Neurol. Jan. 2011;68(1):45-50. Epub Sep. 13, 2010.*

Harrington et al. Rosiglitazone does not improve cognition or global function when used as adjunctive therapy to AChE inhibitors in mild-to-moderate Alzheimer's disease: two phase 3 studies. Curr Alzheimer Res. Aug. 2011;8(5):592-606.* de la Monte et al. Review of insulin and insulin-like growth factor expression, signaling, and malfunction in the central nervous system: relevance to Alzheimer's disease. J Alzheimers Dis. Feb. 2005;7(1):45-61.*

Arnalich et al., "Relationship of Plasma Leptin to Plasma Cytokines and Human Survivalin Septsis and Septic Shock," J. Infect. Dis. 180:908-11 (1999).

Barrett-Connor et al., "Weight loss precedes dementia in community-dwelling older adults," J Am Geriatr Soc. 44:1147-52 (1996).

Batterham, R.L., et al., "Inhibition of food intake in obese subjects by peptide YY3-36," N Engl J Med. 349:941-8 (2003).

Baumann, H. et al., "The Full-Length Leptin Receptor has Signaling Capabilities of Interleukin 6-Type Cytokine Receptors," Proc. Natl. Acad. Sci. USA 93:8374 (1996).

Benveniste et al., "Immunological Aspects of Microglia: Relevance to Alzheimer's Disease," Neurochem Int'l, 39:381-91 (2001).

Bickel, P.E. et al., Flotillin and epidermal surface antigen define a new family of caveolae-associated integral membrane, J Biol Chem. 272:13793-802 (1997).

Bissoli, L. et al., "Energy balance in Alzheimer's disease," J Nutr Health Aging. 6:247-53 (2002).

Bjorbaek, C., K. et al., "The Role of SOCS-3 in Leptin Signaling and Leptin Resistance," J. Biol. Chem. 274:30059 (1999).

Blasko et al., "TNFalpha Plus IFNgamma Induce the Production of Alzheimer Beta-Amyloid Peptides and Decrease the Secretion of APPs," FASEB J. 13:63-68 (1999).

Bradford, M.M. et al., A rapid and sensitive method for the quantitation of microgram quantities of protein utilizing the principle of protein-dye binding, Anal Biochem. 72:248-54 (1976).

Brown, M.S. et al., "The SREBP pathway: regulation of cholesterol metabolism by proteolysis of a membrane-bound transcription factor," Cell. 89:331-40 (1997).

Cheng, A. N. et al., "Attenuation of Leptin Action and Regulation of Obesity by Protein Tyrosine Phosphatase 1B," Dev. Cell 2:497 (2002).

Chezet, F., A. et al., "Leptin: A Potential Regulator of Polymorphonuclear Neutrophil Bactericidal Action," J. Leukocyte Biol. 69:414 (2001).

Chung, W.K. et al., "Heterozygosity for Lep/ob or Lepr/db affects body composition and leptin homeostasis in adult mice," American Journal of Physiology. 274:R985-R990 (1998).

Cordy, J.M. et al., "Exclusively targeting {beta}-secretase to lipid rafts by GPI-anchor addition up-regulates {beta}-site processing of the amyloid precursor protein," Proc Natl Acad Sci U S A. 100:11735-11740 (2003).

Couce, M.E. et al. "Localization of leptin receptor in the human brain," Neuroendocrinology, 66:145-50 (1997).

Danik, M. et al., "Brain lipoprotein metabolism and its relation to neurodegenerative disease," Crit Rev Neurobiol. 13:357-407 (1999).

De Strooper, "Aph-1, Pen-2, and Nicastrin with Presenilin Generate an Active γ-Sectetase Complex," Neuron. 38:9-12 (2003).

Duff, K. et al., "Increased amyloid-beta42(43) in brains of mice expressing mutant presenilin 1," Nature. 383:710-3 (1996).

Emmerling et al., "The Role of Complement in Alzheimer's Disease Pathology," Biochem Biophys Acta 1502:158-71 (2000).

Fagan, A.M. et al., "Unique lipoproteins secreted by primary astrocytes from wild type, apoE (-/-), and human apoE transgenic mice," J Biol Chem. 274:30001-7 (1999).

Faggioni, R. et al., "Leptin Regulation of the Immune Response and the Immunodeficiency of Malnutrition," FASEB J. 15:2565-71 (2001).

Farris, W., S. et al., "Insulin-degrading enzyme regulates the levels of insulin, amyloid-beta protein, and the beta-amyloid precursor protein intracelllular domain in vivo," Proc Natl Acad Sci U S A. 100:4162-4167 (2003).

Feng, B., et al., "The endoplasmic reticulum is the site of cholesterol-induced cytotoxicity in macrophages," Nat Cell Biol. 5:781-92 (2003).

Figueiredo-Pereira et al., "Distinct secretases, a cysteine protease and a serine protease, generate the C termini of amyloid beta-proteins Abeta1-40 and Abeta1-42, respectively," J Neurochem. 72:1417-22 (1999).

Ford, M.J. et al., "Selective expression of prion protein in peripheral tissues of the adult mouse," Neuroscience. 113:177-92 (2002).

Ghosh, Tapash K. et al., "Transdermal and Topical Drug Delivery Systems," Culinary and Hospitality Industry Publications Services, pp. 249-297 (2007).
Heshka, J.T. et al., "A Role for Dietary Fat in Leptin Receptor, OB-Rb, Function," Life Sci. 69:987-1003 (2001).
Holcomb, L. et al., "Accelerated Alzheimer-type phenotype in transgenic mice carrying both mutant amyloid precursor protein and presenilin 1 transgenes," Nat Med. 4:97-100 (1998).
Hsiao, K. et al., "Correlative memory deficits, Abeta elevation, and amyloid plaques in transgenic mice," Science. 274:99-102 (1996).
Isidori, A., et al., "Leptin and Aging: Correlation with endocrine changes in male and female healthy adult populations of different body weights," The Journal of Clinical Endocrinilogy & Metabolism. 85:1954-1962 (2000).
Johnsingh et al., "Altered Binding of Mutated Presenilin with Cytoskeleton-Interacting Proteins," J. Neurosci. 14:4769-79 (2000).
Johnsingh, A.A. et al., "Altered binding of mutated presenilin with cytoskeleton-interacting proteins," FEBS Lett. 465:53-8 (2000).
Kang, D.E. et al., "Modulation of amyloid beta-protein clearance and Alzheimer's disease susceptibility by the LDL receptor-related protein pathway," J Clin Invest. 106:1159-66 (2000).
Kawarabayashi, T. et al., "Age-dependent changes in brain, CSF, and plasma amyloid (beta) protein in the Tg2576 transgenic mouse model of Alzheimer's disease," J Neurosci. 21:372-81 (2001).
Kempen, H.J. et al., "Secretion of apolipoproteins A-I and B by HepG2 cells: regulation by substrates and metabolic inhibitors," J Lipid Res. 36:1796-1806 (1995).
Kersten, "Mechanisms of Nutritional and Hormonal Regulation of Lipogenesis," EMBO Reports 2(4):282-286 (2001).
King et al., "AMP-Activated Protein Kinase (AMPK) Activating Agents Cause Dephosphorylation of Akt and Glycogen Synthase Kinase-3," Biochem. Pharmacol. 71:1637-47 (2006).
LaDu, M.J. et. al., "Apolipoprotein E and apolipoprotein E receptors modulate A beta-induced glial neuroinflammatory responses," Neurochem Int. 39:427-34 (2001).
Lee Y., et al., "Liporegulation in Diet-Induced Obesity," J. Biol Chem. 276(8):5629-35 (2001).
Lemaire-Vieille, C. et al. "Epithelial and endothelial expression of the green fluorescent protein reporter gene under the control of bovine prion protein (PrP) gene regulatory sequences in transgenic mice," Proc Natl Acad Sci U S A. 97:5422-7 (2000).
Lichtenthaler, S.F. et al., "Amyloid at the cutting edge: activation of α-secretase prevents amyloidogenesis in an Alzheimer disease mouse model," J. Clin. Invest. 113:1384-1387 (2004).
Puglielli, L. et al., "Acyl-coenzyme A: cholesterol acyltransferase modulates the generation of the amyloid beta-peptide," Nature Cell Biology. 3:905-912 (2001).
Loftus, T.M. et. al., "Reduced food intake and body weight in mice treated with fatty acid synthase inhibitors," Science. 288:2379-81 (2000).
Lord, G.M. et al., Leptin Modulates the T-Cell Immune Response and Reverses Starvation-Induced Immunosuppression, Nature 394:897 (1998).
Martin-Romero, C., V., et al., "Human Leptin Activates P13K and MAPK Pathways in Human Peripheral Blood Mononuclear Cells: Possible Role of Aam68," Cell., Immunol. 212-83 (2001).
Minokoshi, Y. et al., "Leptin stimulates fatty-acid oxidation by activating AMP-activated protein kinase," Nature. 415:339-43 (2002).
Mobbs, C.V.M., H. 2002. "Block the FAS, loose the fat," Nature Medicine. 8:335-336.
Loftus, et al., "Reduced Food Intake and Body Weight in Mice Treated with Fatty Acid Synthase Inhibitors," Science. 288:2379-81 (2002).
Narita, M. et. al., "Cellular catabolism of lipid poor apolipoprotein E via cell surface LDL receptor-related protein," J Biochem (Tokyo). 132:743-9 (2002).
Paula G. Ulery et al., "LRP in Alzheimer's Disease: Friend or Foe?," J. Clin. Invest. 106(9):1077-1079 (2000).
Qiu, et al., "Degradation of amyloid beta-protein by a metalloprotease secreted by microglia and other neural and non-neural cells," J Biol Chem. 272:6641-6646 (1997).
Refolo, et al., "Hypercholesterolemia accelerates the Alzheimer's amyloid pathology in a transgenic mouse model," Neurobiol Dis. 7:321-31 (2000).
Sanchez-Margalet, V.C. et al., Human Leptin Signaling in Human Peripheral Blood Mononuclear Cells: Activation of the JAK-STAT Pathway, Cell. Immunol. 211:30 (2001).
Schindler et al., "Transcriptional Responses to Polypeptide Ligands: The JAK-STAT Pathway," Ann. Rev. Biochem. 64:621-51 (1995).
Schwartz, M.W. et al., "Central nervous system control of food intake," In Nature. vol. 404. 661-71 (2000).
Shanley, L.J. et al., "Leptin inhibits rat hippocampal neurons via activation of large conductance calcium-activated K+ channels," Nat Neurosci. 5:299-300 (2002).
Shimano et al., "Isoform 1c of Sterol Regulatory Element Binding Protein is Less Active Than Isoform 1a in Livers of Transgenic Mice and in Cultured Cells," J. Cli. Inv. 99:846-854 (1997).
Shimoda, et al., "A high percentage yield of tyrosine hydroxylase-positive cells from rat E14 mesencephalic cell culture," Brain Res. 586:319-31 (1992).
Shimomura, et al., "Increased Levels of Nuclear SREBP-1c Associated with Fatty Livers in Two Mouse Models of Diabetes Mellitus," J Biol Chem. 274:30028-32 (1999).
Simons, M. et al., "Cholesterol Depletion Inhibits the Generation of Beta-Amyloid in Hippocampal Neurons," Proc Natl Acad Sci U S A. 95:6460-4 (1998).
Sleeman, et al., "The Ciliary Neurotrophic Factor and its Receptor, CNTFR Alpha," Pharm Acta Helv. 74:265-72 (2000).
Takeshima, T., et al., "Mesencephalic Type 1 Astrocytes Rescue Dopaminergic Neurons from Death Induced by Serum Deprivation," J Neurosci. 14:4769-79 (1994).
Takeshima, T. et al., "Standardized Methods to Bioassay Neurotrophic Factors for Dopaminergic Deurons," J Neurosci Methods. 67:27-41 (1996).
Tartaglia, Louis, A., "The Leptin Receptor," J. Biol, Chem. Minireview, 272:6093-6096 (1997).
Tezapsidis, N. et al., "Microtubular Interactions of Presenilin Direct Kinesis of A Beta Peptide and its Precursors," FASEB J. 17:1322-1324 (2003).
Toyoshima et al., "Leptin Improves Insulin Resistance and Hyperglycemia in a Mouse Model of Type 2 Diabetes," Endocrinology 146:4024-35 (2005).
Unger RH., "The Physiology of Cellular Liporegulation," Annu Rev Physiol. 65:333-47 (2003).
Unger, "Lipotoxic Diseases," Annu Rev. Med. 53:319-36 (2002).
Ur, E. et al., "Leptin Immunoreactivity is Localized to Neurons in Rat Brain," Neuroendocrinology. 75:264-72 (2002).
Watson, G.S.C., S. 2003. The Role of Insulin Resistance in the Pathogenesis of Alzheimer's Disease: Implications for Treatment, CNS Drugs. 17:27-45 (2003).
Wilentz, Robb E. et al., Lipogenic Enzymes Fatty Acid Synthase and Acetyl-Coexpressed with Sterol Regulatory Element Binding Protein and Ki-67 in Fetal Tissues, Pediatric and Developmental Pathology, 3(6):525-531 (2000).
Wood, W.G. et al., "Brain membrane cholesterol domains, aging and amyloid beta-peptides," Neurobiol Aging. 23:685-694 (2002).
Xiao et al., "Leptin Modulates Inflammatory Cytokine and Neuroendocrine Responses to Endotoxin in the Primate," Endocrinology 144:4350-53 (2003).
Yu, Y.H., et al., "Posttranscriptional Control of the Expression and Ffunction of Diacylglycerol Acyltransferase-1 in Mouse Adipocytes," J Biol Chem. 277:50876-84 (2002).
Zarkesh-Esfahani, H., G. et al., "High-Dose Leptin Activates Human Leukocytes Via Receptor Expression on Monocytes," J. Immunol. 157:4593 (2001).
Zhao, Y., R. et al., "Expression of Leptin Receptors and Response to Leptin Stimulation of Human Nature Killer Cell Lines," Biochem. Biophys. Res. Commun. 300:247(2003).
Frenkel, Dan et al., "Nasal Vaccination with a Proteosome-Based Adjuvant and Glatiramer Acetate Clears β-Amyloid in a Mouse Model of Alzheimer Disease," J. Clin. Invest. 115:2423-2433 (2005).
Gandy, Sam "The Role of Cerebral Amyloid β Accumulation in Common Forms of Alzheimer Disease," J. Clin. Invest. 115:1121-1129 (2005).

Kawarabayashi, Takeshi et al., "Dimeric amyloid β Protein Accumulates in Lipid Rafts Followed by Apolipoprotein E and Phosphorylated Tau Accumulation in the Tg2576 Mouse Model of Alzheimer's Disease," J. Neurosci. 24(15):3801-3809 (2004).
Matarese, Giuseppe et al., "Leptin in Immunology," J. of Immun. 173:3137-3142 (2005).
Postina, Rolf et al., "A Disintegrin-Metalloproteinase Prevents Amyloid Plaque Formation and Hippocampal Defects in an Alzheimer Disease Mouse Model." J. Clin. Invest. 113:1456-1464 (2004).
Truett, Gary E. et al., "Rat Obesity Gene Fatty (fa) Maps to Chromosome 5: Evidence for Homology with the Mouse Gene Diabetes (db)," Proc. Natl. Acad. Sci. USA. 88:7806-7809 (1991).
Tschape, Jakob A. et al., "Therapeutic Perspectives in Alzheimer's Disease," Recent Patents on CNS Drug Discovery 119-127 (2006).
Yanagisawa, Makoto et al., "Roles of Lipid Rafts in Integrin-Dependent Adhesion and gp130 Signalling Pathway in Mouse Embryonic Neural Precursor Cells," Genese to Cells 9:801-809 (2004).
International Search Report for PCT/US09/63310 dated Feb. 25, 2010.
Hardy et al., "The Amyloid Hypothesis of Alzheimer's Disease: Progress and Problems on the Road to Therapeutics"; Science's Compass Review; Science, vol. 297, pp. 353-356 (2002).
McGowen et al., "Amyloid-like Inclusions in Huntington's Disease", Neuroscience 100(4): 677-680 (2000).
Conway et al., "Fibrils Formed in Vitro from α-Synuclein and Two Mutant Forms Linked to Parkinson's Disease are Typical Amyloid", Biochemistry, 39, pp. 2552-2563 (2000).
Schwartz et al., "Central Nervous System Control of Food Intake", Nature vol. 404, Apr. 6, 2000; pp. 661-671.
Schindler et al., "Transcriptional Responses to Polypeptide Ligands: The JAK-STAT Pathway", Annu. Rev. Biochem. 1995 64:621-51.
Tartaglia, Louis A., "The Leptin Receptor", The Journal of Biological Chemistry, vol. 272, No. 10, Issue of Mar. 7, pp. 6093-6096 (1997).
Martin-Romero et al., "Human Leptin Activated PI3K and MAPK Pathways in Human Peripheral Blood Mononuclear Cells: Possible Role of Sam68", Cellular Immunology, 212, 81-91 (2001).
Sanchez-Margalet et al., "Human Leptin Signaling on Human Peripheral Blood Mononuclear Cells: Activation of the JAK-STAT Pathway", Cellular Immunology, 211, 30-36 (2001).
Unger, Robert H., "The Physiology of Cellular Liporegulation", Annu. Rev. Physiol. 2003. 65: 333-47.
Lee et al., "Liporegulation in Diet-induced Obesity: The Antisteatotic Role of Hyperleptinemia", The Journal of Biological Chemistry, vol. 276, No. 8, Issue of Feb. 23, 2001, pp. 5629-5635.
Toyoshima et al., "Leptin Improves Insulin Resistance and Hyperglycemia in a Mouse Model of Type 2 Diabetes", Endocrinology 146(9): 4024-4035 (2005).
Kersten, Sander "Mechanisms of nutritional and hormonal regulation of lipogenesis", EMBO reports, vol. 2, No. 4, pp. 282-286 (2001).
Merrifield, R. B., "Solid Phase Peptide Synthesis. I. The Synthesis of a Tetrapeptide", J. Am. Chem. Soc. 85: 2149-2154, Jul. 20, 1963.
Carpino et al., "The 9-Fluorenylmethoxycarbonyl Amino-Protecting Group", J. Org. Chem., vol. 37, No. 22, pp. 3404-3409 (1972).
Fields et al., "Solid phase peptide synthesis utilizing 9-fluorenylmethoxycarbonyl amino acids", Int. J. Peptide Protein Res. 35, pp. 161-214 (1990).
Langer, Robert, "New Methods of Drug Delivery", Science, vol. 249, pp. 1527-1533 (1990).
Ishida et al., "Stabilization of Camodulin-dependent Protein Kinase II through the Autoinhibitory Domain", The Journal of Biological Chemistry, vol. 270, No. 5, Issue of Feb. 3, pp. 2163-2170 (1995).
Zhou et al., "Role of AMP-activated protein kinase in mechanism of metformin action", The Journal of Clinical Investigation, Oct. 2001, vol. 108, No. 8, pp. 1167-1174.
Klein, et al., "A molecular mechanism for the effect of lithium on development", Proc. Natl. Acad. Sci. USA, vol. 93, pp. 8455-8459 (1996).
Clare et al., "The Cyclin-dependent Kinases cdk2 and cdk5 Act by a Random, Anticooperative Kinetic Mechanism", The Journal of Biological Chemistry, vol. 276, No. 51, Issue of Dec. 21, pp. 48292-48299 (2001).
Chen et al., "Characterization of ATP-independent ERK inhibitors identified through silico analysis of the active ERK2 structure", Bioorganic & Medicinal Chemistry Letters 16, pp. 6281-6287 (2006).
Han, et al., "c-Jun N-terminal kinase is required for metalloproteinase expression and joint destruction in inflammatory arthritis", The Journal of Clinical Investigation, vol. 108, No. 1, pp. 73-81 (2001).
Kase et al., "K-252 Compounds, Novel and Potent Inhibitors or Protein Kinase C and Cyclic Nucleotide-Dependent Protein Kinases", Biochemical and Biophysical Research Communications, vol. 142, No. 2, pp. 436-440 (1987).
Siddiquee et al., "Selective chemical probe inhibitor of Stat3, identified through structure-based virtual screening, induces antitumor activity", Proc. Natl. Acad. Sci. USA, vol. 104, No. 18, pp. 7391-7396 (2007).
Bilancio et al., "Key role of the p110σ isoform of PI3K in B-cell antigen and IL-4 receptor signaling: comparative analysis of genetic and pharmacologic interference with p110σ function in B cells", Blood, vol. 107, No. 2, pp. 642-650 (2006).
Hu et al., "3-(Hydroxymethyl)-Bearing Phosphatidylinositol Ether Lipid Analogues and Carbonate Surrogates Block PI3-K, Akt, and Cancer Cell Growth", J. Med. Chem. 2000, 43, pp. 3045-3051 (2000).
de Laszlo et al., "Pyrroles and Other Heterocycles as Inhibitors of P38 Kinase", Bioorganic & Medicinal Chemistry Letters 8, pp. 2689-2694 (1998).
Ye et al., "The Dipeptide H-Trp-Glu-OH Shows Highly Antagonistic Activity Against PPARγ: Bioassay with Molecular Modeling Simulation", ChemBioChem, 7, pp. 74-82 (2006).
Peterson et al., "Design, Development, Manufacturing, and Testing of Transdermal Drug Delivery Systems", Transdermal and Topical Drug Delivery Systems, pp. 249-297, Interpharm Press, Inc. (1997).
Diagnostics Criteria for Dementia of the Alzheimer's Type, Diagnostic and Statistical Manual of Mental Disorders, Fourth Edition, Copyright American Psychiatric Association (1994).

* cited by examiner

Abeta peptide amino acid sequence, membrane domain and cleavage sites

Mechanisms of Abeta production and clearance d e a b c d b c d e

LEPTIN AS AN ANTI-AMYLOIDOGENIC BIOLOGIC AND METHODS FOR DELAYING THE ONSET AND REDUCING ALZHEIMER'S DISEASE-LIKE PATHOLOGY

CROSS-REFERENCE TO RELATED APPLICATION

This application claims priority benefit of U.S. Provisional Application Ser. No. 60/714,948, filed Sep. 7, 2005, which is hereby incorporated by reference in its entirety.

FIELD OF THE INVENTION

The present invention relates to methods for treating, preventing, or diagnosing the pathology of progressive cognitive disorders resulting from accumulation of an amyloid peptide.

BACKGROUND OF THE INVENTION

Weight loss frequently is observed in Alzheimer's disease (AD) patients prior to the onset of dementia, supportive of an underlying metabolic disorder. (Barrett-Connor et al., *J Am Geriatr Soc.* 44:1147-52 (1996); Bissoli et al., *J Nutr Health Aging.* 6:247-53 (2002)). Furthermore, lipid homeostasis (meaning the multi-layered regulatory networks of lipid metabolism, transport, and signal transduction) specifically, as exemplified in cell culture and animal models in addition to clinical studies with lipid-lowering agents, e.g., statins, can have an impact on amyloidogenic pathways. Such pathways lead to the generation of amyloid β (Aβ) peptide through proteolytic processing of the amyloid precursor protein (APP). (Stefan F. Lichtenthaler and Christian Haass, *J Clin. Invest.* 113:1384-1387 (2004); Puglielli et al., *Nature Cell Biol.* 3:905-912. (2001)). An important modulator of lipid homeostasis in non-adipose tissues is the pluripotent peptide leptin (Unger in Annu Rev Med. Vol. 53. 319-36 (2002).

In addition to deregulation of lipid metabolism in the CNS, the immune system has been implicated in the pathobiology of Alzheimer's disease. Amyloid plaques are decorated with proteins of the complement system, eicosanoids and cytokines, integral components of ongoing inflammatory processes that augment the harmful effects of Aβ (Emmerling et al., Biochim Biophys Acta 1502: 158-71 (2000)). Important regulators of the immune system include the cytokines and chemokines, secreted by leukocytes (B or T cells, normally scarce in the brain) or antigen presenting cells (APC) (microglia, perivascular macrophages, astrocytes in the brain). In AD brain, both pro-inflammatory cytokines and anti-inflammatory cytokines are expressed (Benveniste et al., Neurochem Int'l, 39: 381-91 (2001)). In addition to immune function, cytokines may directly affect the processing of APP (Blasko et al., FASEB J. 13: 63-68 (1999)). Leptin has very similar structural and functional characteristics to the cytokines (Heshka, J. T., and P. J. Jones, *Life Sci.* 69:987-1003 (2001)), sharing post-receptor pathways and participating in our immune response to pathogens and infections. Leptin deficiency is associated with impaired T cell immunity (Faggioni, R., K. R. Feingold, and C. Grunfeld. 2001. FASEB J. 15:2565-71 (2001)) and increased sensitivity to the lethal effects of bacterial endotoxin and TNF-a. Most importantly, these effects can be reversed with leptin administration, which attenuates inflammatory cytokine and neuroendocrine responses to infection (Xiao et al., Endocrinology 144: 4350-53 (2003)). Further, in critically ill septic patients, higher leptin levels are positively correlated with survival (Amalich et al., J. Infect. Dis. 180: 908-11 (1999)).

According to the present invention, the question of whether leptin and leptin signaling pathways are relevant to the pathology of a progressive brain disorder has been examined. The proposition is based on leptin's anti-amyloidogenic activity (Tezapsidis studies), leptin's ability to attenuate inflammation and leptin's ability to increase insulin sensitivity, a biological profile that could provide a multifaceted benefit to AD patients as a therapy and to the elderly as an intervention.

Leptin is a peptide hormone that controls adaptive metabolic mechanisms to energy availability leading to storage or mobilization of fat (Schwartz et al., Nature. 404: 661-71 (2000)). Adipocyte-derived leptin primarily exerts its central action through the arcuate nucleus neurons (an aggregation of neurons in the mediobasal hypothalamus); however, it can affect other populations, including hippocampal neurons and cells of the periphery (Shanley et al., *Nat Neurosci.* 5:299-300 (2002)). Ablation of leptin or of leptin signaling is sufficient to cause obesity as exemplified by leptin-deficient obese, hyperinsulinemic mice having the genotype ob/ob; diabetic mice with a mutation in the leptin receptor gene having the genotype db/db, which produce but are non-responsive to leptin; rats of the genotype fa/fa, which have the "fatty" obesity gene, which is a mutated leptin receptor; and in a few rare genetic cases (Schwartz et al., Nature. 404: 661-71 (2000)).

The leptin receptor (ObR), a member of the class I cytokine receptor superfamily (Lord, G. M., et al. *Nature* 394:897 (1998)) has at least six isoforms as a result of alternative splicing. As used herein the term "isoform" refers to a version of a protein that has the same function as another protein but that has some small differences in its sequence. All isoforms of ObR share an identical extracellular ligand-binding domain (Couce et al., *Neuroendocrinology.* 66:145-50 (1997)). Leptin's functional receptor (ObRb), the b isoform, is expressed not only in the hypothalamus, where it regulates energy homeostasis and neuroendocrine function, but also in other brain regions and in the periphery, including all cell types of innate and adaptive immunity (Lord, G. M., et al., *Nature* 394:897 (1998); Zhao, Y., R. et al., *Biochem. Biophys. Res. Commun.* 300: 247 (2003)); Zarkesh-Esfahani, H., G. et al., *J. Immunol.* 157: 4593 (2001) Caldefie-Chezet, F., A. et al., *J. Leukocyte Biol.* 69:414 (2001)). The full-length b isoform (ObRb) lacks intrinsic tyrosine kinase activity and is involved in several downstream signal transduction pathways.

Leptin binding to its functional receptor recruits Janus tyrosine kinases and activates the receptor, which then serves as a docking site for cytoplasmic adaptors such as STAT (Baumann, H., et al. *Proc. Natl. Acad. Sci. USA* 93:8374 1996)). According to the general model for JAK/STAT activation, STAT proteins initially are present in inactive forms in the cytoplasm. Following ligand stimulation and receptor dimerization, the JAK/STAT pathway is activated by activation of receptor-bound JAK kinases. These JAK kinases subsequently phosphorylate the receptor at tyrosine residues, which recruits STATs to the receptor. STATs then are phosphorylated to form phosphoSTATs, dimerized, and translocated to the nucleus, where the phosphoSTAT dimers bind to specific sequences in the promoter regions of their target genes, and stimulate the transcription of these genes (Schindler et al., *Ann. Rev. Biochem.* 64: 621-51 (1995)), including negative regulators, such as the suppressor of cytokine signaling 3 (Bjorbaek, C., K. et al. *J. Biol. Chem.* 274:30059 (1999)) and the protein tyrosine phosphatase 1B (Cheng, A. N. et al. *Dev. Cell* 2:497 (2002), Schwartz et al., *Nature,*

404:661-71 (2000), Louis A. Tartaglia, *J. Biol. Chem. Minireview,* 272:6093-6096 (March 1997)).

In addition to the JAK-2-STAT-3 pathway, other pathways also are involved in mediating leptin's effect in the brain and on the immune cells. For example, the mitogen-activated protein kinase (MAPK) pathways, the insulin receptor substrate 1 (IRS1) pathway, and the phosphatidylinositol 3'-kinase (PI3'K) pathway (Martin-Romero, C., V. Sanchez-Margalet. *Cell. Immunol.* 212:83 (2001)) also mediate leptin's action (Sanchez-Margalet, V., C. Martin-Romero, *Cell. Immunol.* 211:30 (2001)).

Leptin also may have a physiologic role as a liporegulatory hormone responsible for maintaining intracellular homeostasis in the face of wide variations in caloric intake (Unger R H. 2003. Annu Rev Physiol. 65:333-47). This is achieved by directly stimulating lipolysis, (meaning fat breakdown), and inhibiting lipogenesis (meaning fat synthesis) (Lee Y, et al., J. Biol Chem. 276(8):5629-35 (2001)). Leptin also can improve insulin resistance and hyperglycemia by a mechanism not completely understood (Toyoshima et al., Endocrinology 146: 4024-35 (2005)), despite insulin's ability to stimulate lipogenesis (Kersten, *EMBO Reports* 2(4): 282-286 (2001). This aspect of leptin's physiological role is important, because insulin and Aβ share a mechanism for their clearance, namely degradation by insulin degrading enzyme (IDE).

The levels of cholesterol and fatty acids in cells also are regulated tightly by a single family of transcription factors named Sterol Regulatory Element-Binding Proteins (SREBPs) which activate relevant target genes (Brown and Goldstein, *Cell.* 89:331-40 (1997)). SREBPs are transcription factors that regulate the expression of genes for both cholesterol and fatty acid synthesis. The inactive precursor form of SREBPs resides in cytoplasmic membranes. Intracellular lipid depletion triggers proteolytic cleavage of the SREBPs, allowing the amino terminus to enter the nucleus and activate the expression of enzymes, including acetyl-CoA carboxylase (ACC) and fatty acid synthase (FAS), major biosynthetic enzymes for fatty acid synthesis. (Wilentz, Robb E. et al., *Pediatric and Developmental Pathology,* 3 (6): 525-531 (2000)).

In the central nervous system (CNS, meaning the brain and spinal cord), metabolic pathways involving lipids serve mainly to provide the building blocks for membranes, vitamins, second messengers and to modify proteins by acylation, because there are no main mechanisms for utilizing triglycerides/fatty acids as energy sources.

It is well documented that brain lipids are intricately involved in Amyloid β (Aβ)-related pathogenic pathways. The Aβ peptide is the major proteinaceous component of the amyloid plaques found in the brains of Alzheimer's disease (AD) patients and is regarded by many as the culprit of the disorder. The amount of extracellular Aβ accrued is critical for the pathobiology of AD and clearly depends on the antagonizing rates of its production/secretion and its clearance. It has been shown (Tezapsidis et al., *FASEB J.* 17:1322-1324 (2003)) that neurons depend on the interaction between Presenilin 1 (PS1) and Cytoplasmic-Linker Protein 170 (CLIP-170) to both generate Aβ and to take it up through the lipoprotein receptor related protein (LRP) pathway. Further to this requirement, formation of Aβ depends on the assembly of key proteins in lipid rafts (LRs) (Simons et al., *Proc Natl Acad Sci USA.* 95: 6460-4 (1998)). The term "lipid rafts" as used herein refers to membrane microdomains enriched in cholesterol, glycosphingolipids and glucosylphosphatidylinositol-(GPI)-tagged proteins implicated in signal transduction, protein trafficking and proteolysis. Within the LRs it is believed that Aβ's precursor, Amyloid Precursor Protein (APP), a type I membrane protein, is cleaved first by the protease β-secretase (BACE) to generate the C-terminal intermediate fragment of APP, CAPPβ, which remains imbedded in the membrane. The amino acid sequence of Aβ peptide showing its cleavage sites and membrane domain is shown in FIG. 1*a*. CAPPβ is subsequently cleaved at a site residing within the lipid bilayer by γ-secretase, a high molecular weight multi-protein complex containing presenilin, (PS1/PS2), nicastrin, PEN-2, and APH-1 or fragments thereof (De Strooper, *Neuron.* 38: 9-12 (2003)). Aβ finally is released outside the cell, where it can: a) start accumulating following oligomerization and exerting toxicity to neurons or b) be removed either by mechanisms of endocytosis (involving apolipoprotein-E (apoE) and LRP or Scavenger Receptors) or by degradation by extracellular proteases including insulin-degrading enzyme (IDE) and neprilysin (Farris et al., *Proc Natl Acad Sci USA.* 100:4162-4167 (2003)) (FIG. 1*b*).

Fatty acid and cholesterol availability and cellular composition modifies the transbilayer distribution of cholesterol and, consequently, overall membrane fluidity, function and localization of lipid rafts, a process which changes with aging (Wood et al., *Neurobiol Aging.* 23:685-694 (2002)). Therefore, it was hypothesized that leptin's lipolytic/antilipogenic activity could affect the composition of the LRs, affecting Aβ turnover.

The present invention demonstrates leptin's ability to modify the levels of Aβ both in vitro and in vivo. Leptin, similarly to methyl-β-cyclodextrin, reduces β-secretase activity in neuronal cells, possibly, but without being limited by theory, by altering the lipid composition of membrane LRs. This contrasts the results of treatments with cholesterol and etomoxir (an inhibitor of carnitine-palmitoyl transferase-1). Conversely, inhibitors of acetyl CoA carboxylase and fatty acid synthase mimicked leptin's action. Additionally, leptin was able to increase apoE-dependent Aβ uptake in vitro. Thus, according to the present invention, leptin can modulate indirectly bi-directional Aβ kinesis, reducing its levels extracellularly. Most strikingly, chronic administration of leptin to AD-transgenic animals reduced the brain Aβ load, illustrating its therapeutic potential.

SUMMARY OF THE INVENTION

The present invention provides a method for treating or preventing a disease, disorder or condition resulting from accumulation of an amyloid peptide, the method comprising the step: administering to a subject in need thereof a first composition comprising (i) a therapeutically effective amount of leptin, a leptin mimic or a leptin derivative and (ii) a pharmaceutically acceptable carrier, thereby modulating accumulation of the amyloid peptide. In one embodiment of this method, amyloid peptide levels in the circulation are monitored by detecting such levels in a sample of cerebrospinal fluid or blood.

In one embodiment of the present invention, the composition further comprises a therapeutically effective amount of one or more lipolytic/antilipogenic compounds.

In another embodiment, the composition is administered by at least one route selected from the group consisting of orally, buccally, parenterally, intranasally, rectally or topically.

In another embodiment of the present invention, the method further comprises the step of serially administering a second composition comprising a therapeutically effective amount of one or more lipolytic/antilipogenic compounds in an amount effective to reduce extracellular amyloid peptide accumulation.

In another aspect, the present invention provides methods for diagnosing a cognitive disorder, disease or condition in a subject comprising the steps of (a) collecting a sample of cerebrospinal fluid or blood from the subject (b) measuring circulating leptin levels in the sample of cerebrospinal fluid or blood; and (c) identifying the subject as having a need to be treated.

Additional methods are provided for modulating amyloid peptide levels in a subject, the methods comprising the step of administering to the subject a composition comprising (i) a leptin inhibitor and (ii) a pharmaceutically acceptable carrier. In another embodiment of the present invention, the composition further comprises (iii) a therapeutically effective amount of one or more lipolytic/antilipogenic compounds.

The present invention also provides methods of modulating amyloid peptide accumulation in a subject, the methods comprising interfering with at least one step in at least one signaling pathway associated with leptin. In one embodiment, the method comprises the step of administering a composition to a subject, wherein the composition comprises a therapeutically effective amount of leptin, a leptin mimic, a leptin derivative, or a leptin agonist, and a pharmaceutically acceptable carrier, thereby modulating accumulation of the amyloid peptide. In another embodiment, the method comprises the step of administering a composition to a subject, wherein the composition comprises a therapeutically effective amount of a leptin inhibitor, a leptin inhibitor mimic, a leptin inhibitor derivative, or a leptin antagonist, and a pharmaceutically acceptable carrier, thereby modulating accumulation of the amyloid peptide.

In panel (a), Neuro2a cells stably transfected with hygsa134 were treated for about 2 h or about 5 h with about 100 ng/ml leptin, Ob (black); about 125 mg/ml cyclodextrin, CDX (gray stripe); about 5 mg/ml cholesterol, Ch (pale gray); leptin plus cholesterol, Ob+Ch (medium gray).

In panel (b), Neuro2a cells stably transfected with hygsa134 were treated for about 2 h or 5 h with about 400 ng/ml leptin, Ob (black); about 250 mg/ml cyclodextrin, CDX (gray stripe), 10 mg/ml cholesterol, Ch (pale gray) and leptin plus cholesterol, Ob+Ch (medium gray).

In panel (c), extracts of SY5Y cells treated with about 400 ng/ml leptin, about 10 μg/ml cholesterol, or both about 400 ng/nl leptin and about 10 μg/ml cholesterol, in the presence of the γ-secretase inhibitors L-685,458 (100 nM) or Z-VL-CHO (100 μM) for about 5 h analysed by SDS-PAGE and Western blotting using an antibody directed against the C-terminal fraction of APP (C-APP, lanes 1-4), actin (top lanes 5-8) or full-length APP (bottom lanes 5-8).

In panel (d), SDS-PAGE and Western blot analysis of sucrose gradient fractions of Triton-X solubilized extracts prepared from SY5Y cells treated with about 400 ng/ml leptin, about 10 μg/ml cholesterol, or both about 400 ng/nl leptin and about 10 μg/ml cholesterol, in the presence of the γ-secretase inhibitors L-685,458 (100 nM) or Z-VL-CHO (100 μM) for about 5 h to detect APP and flotillin (a marker for lipid rafts).

In panel (e), sucrose gradient fractions in (d) were assayed for β-secretase activity using a fluorescence-quenching assay (QTL Biosystems, NM).

Figure 5:
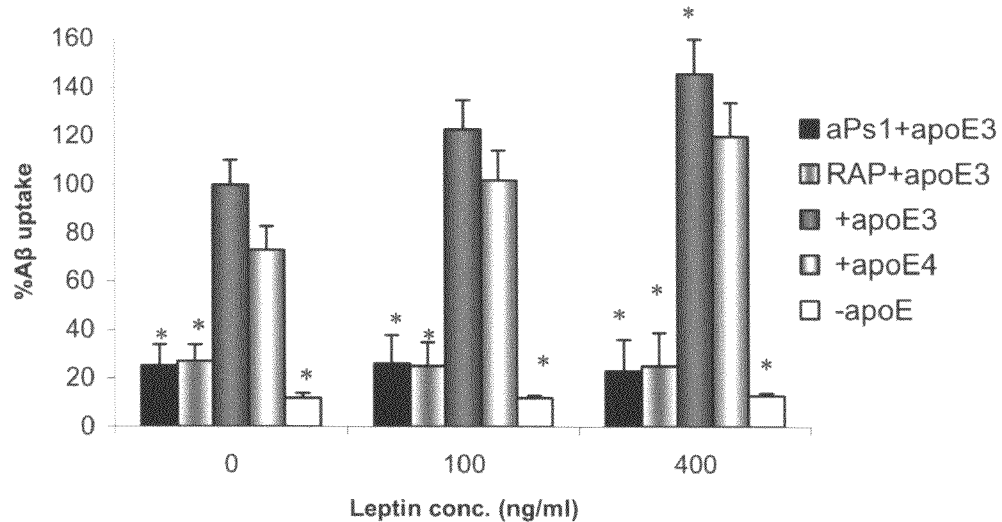
Figure 5:
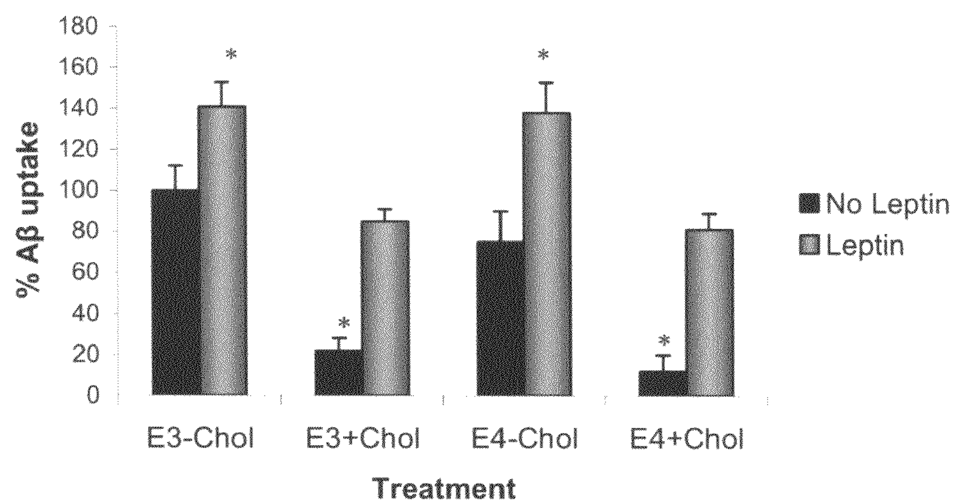
Figure 5:
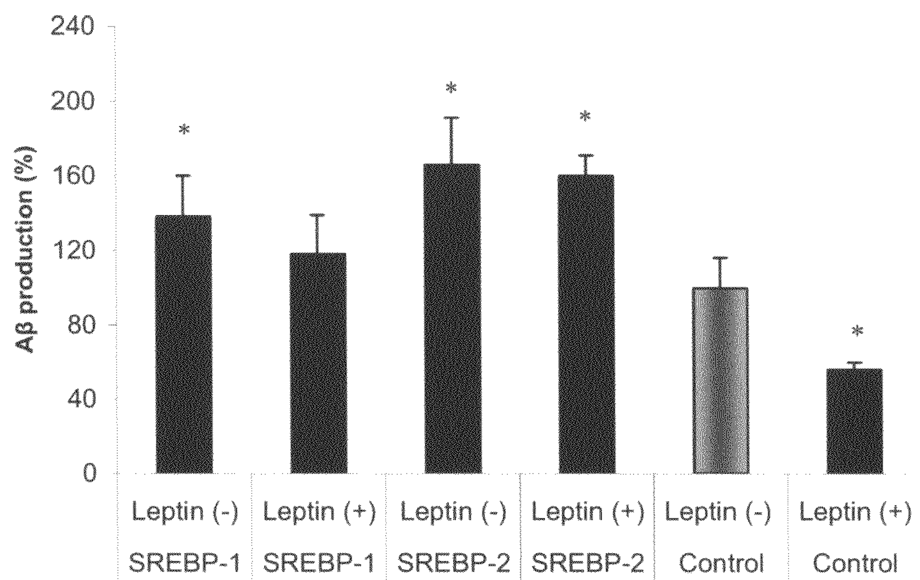
Figure 5:
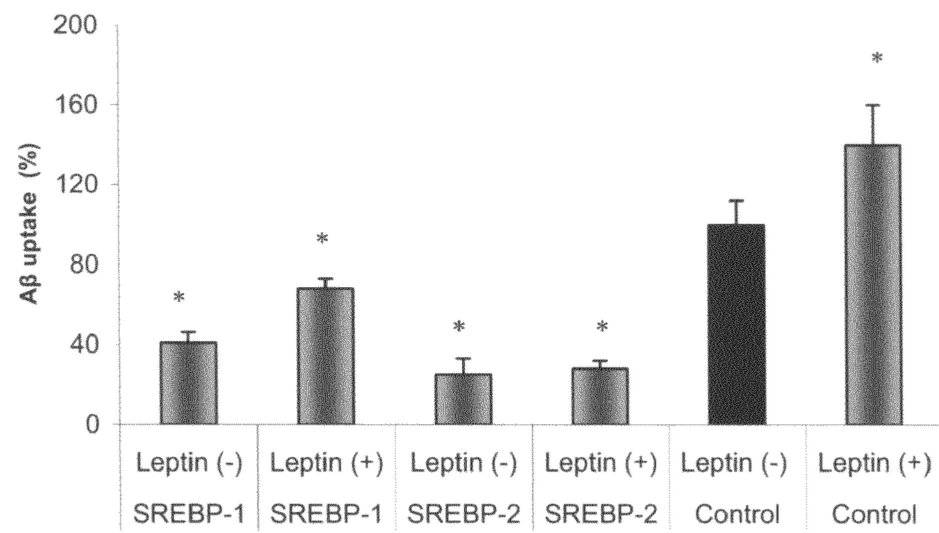

FIG. 5 shows that leptin affects apoE-dependent Aβ-uptake and the possible involvement of SREBPs.

In panel (a), Aβ uptake in SY5Y cells following treatment with about 0 ng/ml, about 100 ng/ml or about 400 ng/ml leptin. Uptake did not take place without apoE (white). Uptake was also dependent on PS1 and LRP, as shown in cells previously transfected with antisense DNA for PS1 (black) and in cells treated with RAP (gray stripe) respectively. Leptin induced a dose-dependent increase in Aβ uptake with a preference for apoE3 (medium gray) over apoE4 (light gray).

In panel (b), Aβ uptake in SY5Y cells pre-treated with about 10 mg/ml cholesterol (+Chol) or normal medium (−Chol). in the absence (black) or the presence (gray) of about 400 ng/ml leptin is shown. Cells were more resistant to taking-up Aβ when pre-loaded with cholesterol. Asterisks indicate that the value is significantly different to that set as 100% (set at $p<0.05$).

In panel (c), measurement of Aβ in the medium of SY5Y cells transiently transfected with SREBP-1 cDNA, SREBP-2 cDNA, or an empty vector (Control) by ELISA following treatment with (+) or without (−) leptin is shown.

In panel (d), measurement of Aβ uptake in SY5Y cells transiently transfected with transcriptionally active forms of SREBP-1a cDNA, SREBP-2 cDNA, or an empty vector (Control) following treatment with (+) or without (−) leptin is shown.

Figure 6:
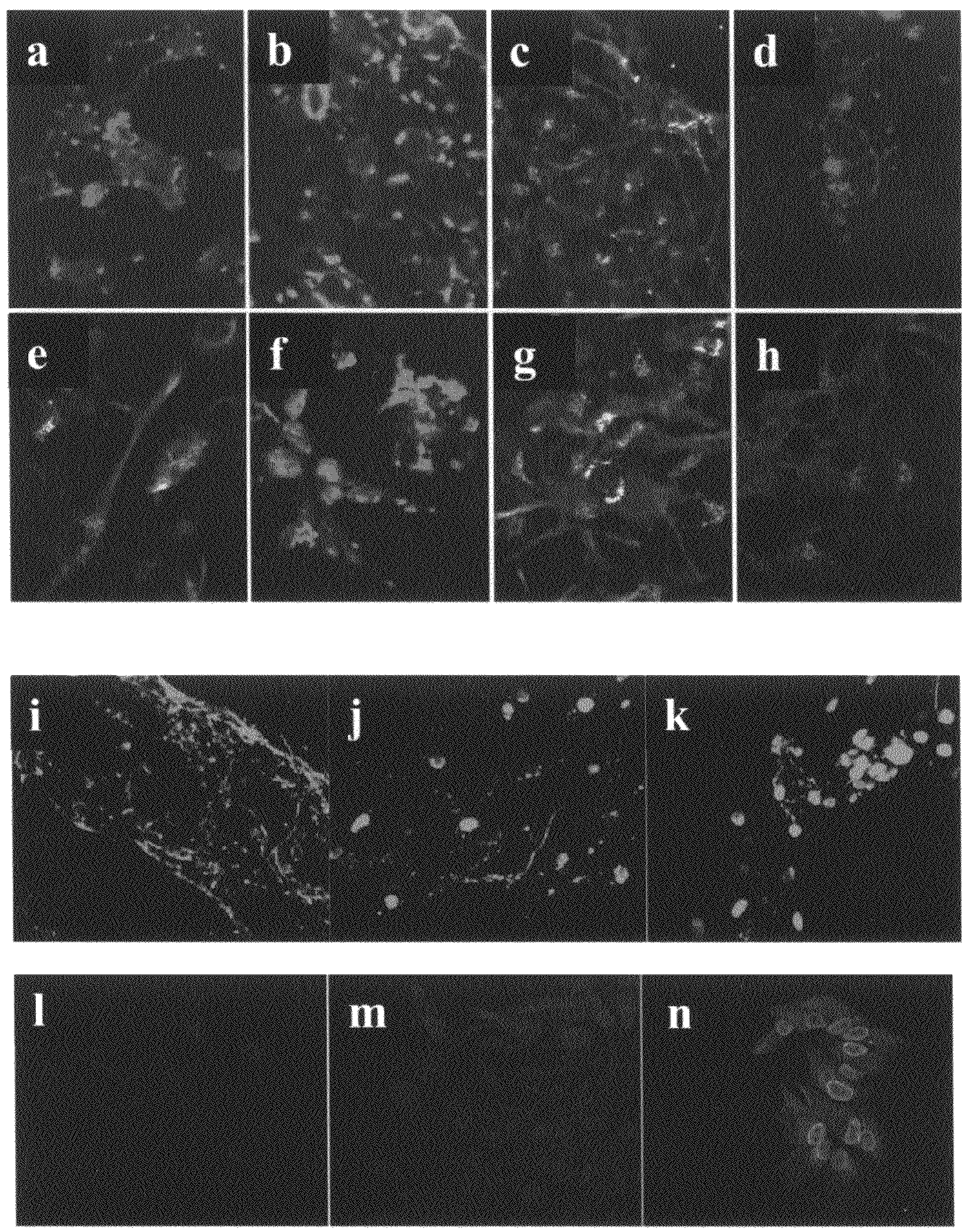

FIG. 6 shows that leptin modulates free cholesterol-rich membrane domains and that surplus cholesterol may trigger leptin. Neural cultures from E15 rat cerebral cortex were processed for enrichment in neurons (a-d) or astrocytes (e-h) and, after about 7 days to 10 days in culture, treated for about 5 h with about 10 μg/ml cholesterol (b, f) or about 400 ng/ml leptin plus cholesterol (c, g) or leptin alone (d, h). Controls (a, e) were treated with media alone. Cells were stained for filipin. Neurons (i-k) and astrocytes (l-n) treated with about 0 μM (i, l), about 5 μM (j, m) or about 10 μM cholesterol (k, n) for about 5 h were immunostained for leptin.

Figure 7:
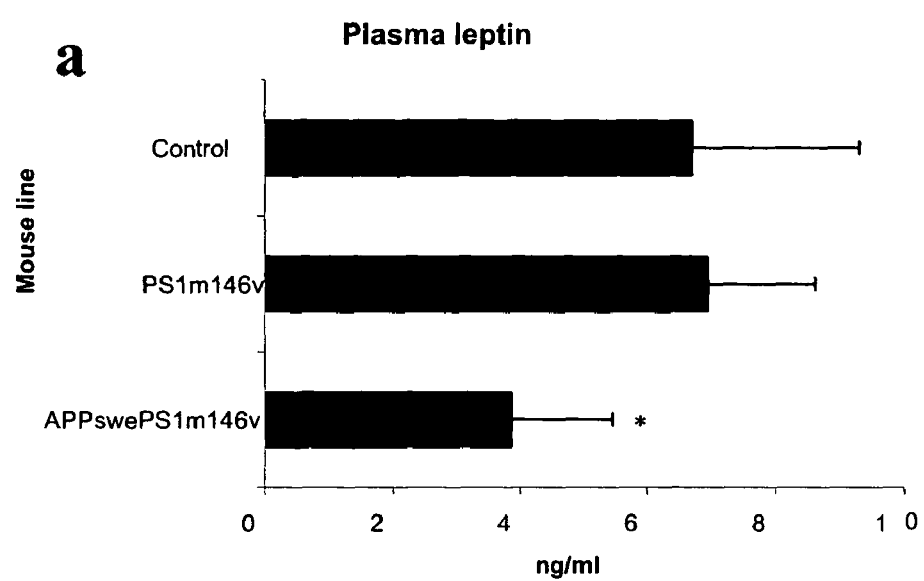
Figure 7:
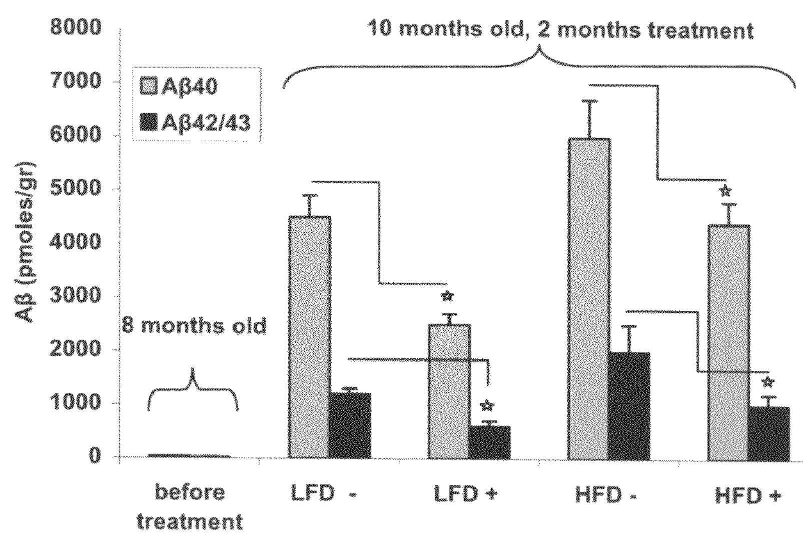
Figure 7:
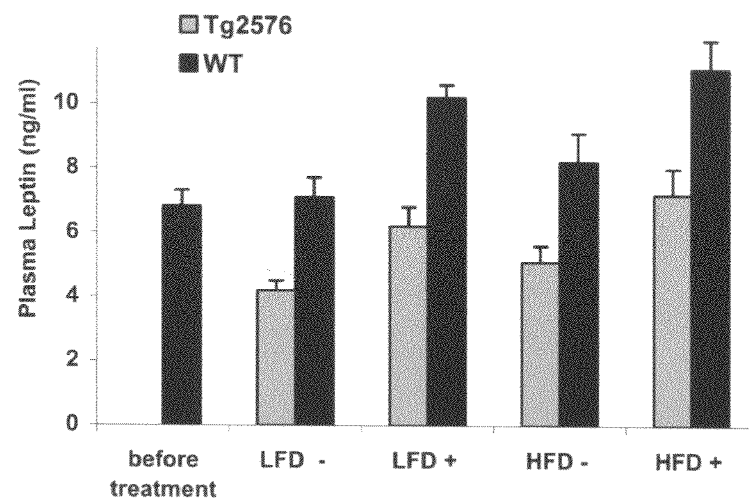
Figure 7:
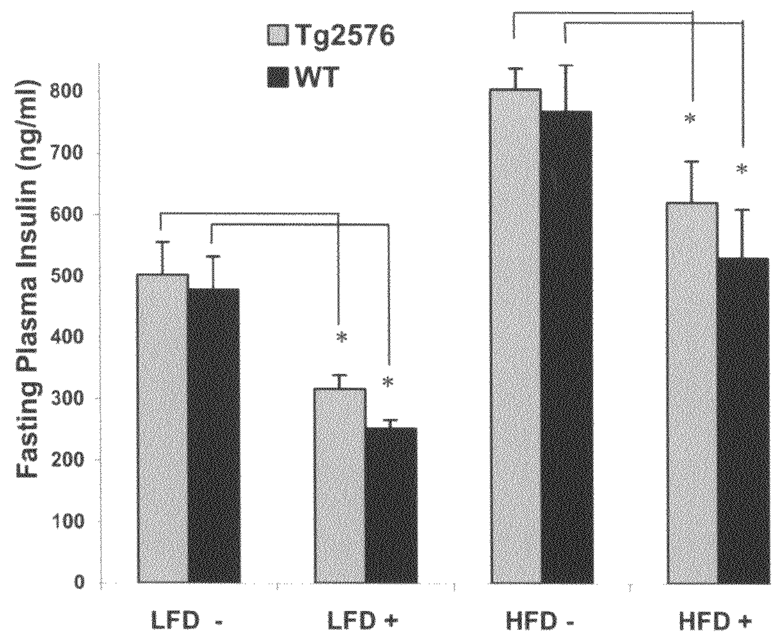
Figure 7:
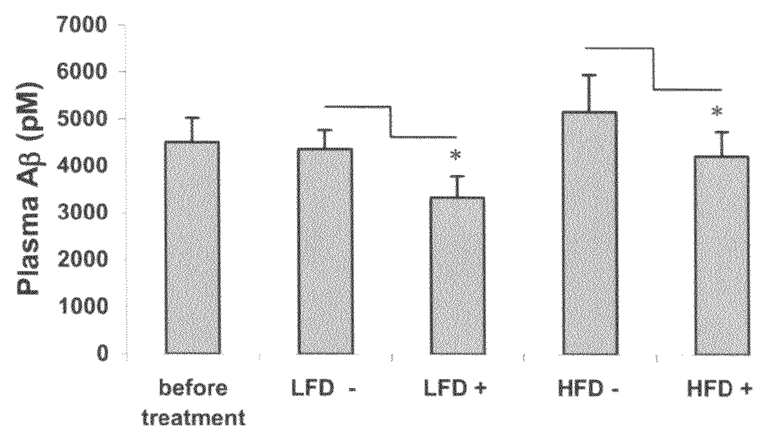

FIG. 7 shows the deficiency of leptin in AD transgenic mice and the effect of leptin supplementation on amyloid load.

In panel (a), plasma leptin was quantified in one year old mice with the following genotypes: a) double mutant $APP_{Swe}PS1_{M146V}$ b) single mutant $PS1_{M146V}$ and c) wild-type (a cross between C57BL/6Ntac and B6SJLF1). Asterisk indicates that the value is significantly different to that of non-transgenic controls (set at $p<0.05$).

In Panel (b) Tg2576 mice under a high fat diets (HFD) and a low fat diets (LFD) from one week prior to the implantation of the Alzet pump subcutaneously (s.c) for constant delivery of leptin (+) or vehicle PBS (−). Pump was replaced after 4 weeks for another 4 week period of treatments. Aβ40 and Aβ42 content in formic acid brain extracts prepared from Tg2576 and wild type (WT) mice were determined by ELISA. Plasma total Aβ (Aβ40 plus Aβ42/43) was measured in 10 month Tg2576 mice following a 2 month LFD or HFD with (+) or without (−) leptin infusion.

In panel (c), plasma leptin levels were determined by RIA in 10 month old Tg2576 and WT littermate mice following treatments as described in FIG. 7*b*. Leptin also was measured in WT (but not Tg2576) mice prior to treatment.

In panel (d), plasma insulin levels were determined by RIA in 8 month old WT and Tg2576 mice and then again following a 2 month LFD or HFD with (+) or without (−) leptin infusion.

In panel (e), plasma total Aβ (Aβ40 plus Aβ42/43) was measured in 8 month Tg2576 mice and then again following a 2 month LFD or HFD with (+) or without (−) leptin infusion.

DETAILED DESCRIPTION OF THE INVENTION

Alzheimer's disease (AD) is characterized histologically by the presence of extracellular amyloid deposits in the brain, together with widespread neuronal loss. Extracellular amyloid deposits are known as neuritic or senile plaques. Amyloid deposits can also be found within and around blood vessels. The main protein constituent of AD and AD-like senile plaques, a peptide known as Aβ, is a normal proteolytic product of a much larger transmembrane protein, the amyloid precursor protein (APP). Aβ can be detected in plasma and cerebrospinal fluid (CSF) in vivo, and in cell culture media in vitro. The terms "amyloid peptide" "amyloid β peptide" and "Aβ" are used interchangeably herein to refer to the family of peptides generated through proteolytic processing of the amyloid precursor protein (APP). APP exists as three different spliced isoforms, one having 770 amino acids (isoform a) (SEQ ID NO:1), one having 751 amino acids (isoform b) (SEQ ID NO:2), and one having 695 amino acids (SEQ ID NO:3). The term "APP" as used herein refers to all three isoforms. The terms "amyloid peptide" "amyloid β peptide" and "Aβ" include, but are not limited to, Aβ40 (SEQ ID NO:4), Aβ42 (SEQ ID NO:5) and Aβ43 (SEQ ID NO:6). The two major forms of Aβ are Aβ40 (SEQ ID NO:4), corresponding to a 40 amino acid-long peptide and Aβ42 (SEQ ID NO:5), corresponding to a 42 amino acid-long peptide. Aβ43 (SEQ ID NO:6) corresponds to a 43 amino acid-long Aβ peptide.

The term "amyloidoses" as used herein refers to a group of conditions of diverse etiologies characterized by the accumulation of insoluble fibrillar proteins (amyloid) in various organs and tissues of the body, wherein eventually organ function is compromised. The associated disease states may be inflammatory, hereditary or neoplastic and the deposition of the amyloid peptide may be localized, generalized or systemic.

The present invention provides a method for treating or preventing the pathology of a disease, disorder or condition resulting from accumulation of an amyloid peptide in a subject. Preferably, the amyloid peptide is an amyloid β peptide. Such a disease, disorder or condition may be any cognitive impairment, including, but not limited to, a dementia; amyloidoses, such as AD and senile systemic amyloidosis; Down's syndrome (patients with Down's syndrome, characterized by trisomy 21, have an extra copy of APP and develop senile plaques from about 12 years of age); cerebral amyloid angiopathy (CAA), also known as congophilic angiopathy or cerebrovascular amyloidosis (a disease of small blood vessels in the brain in which deposits of amyloid protein in the vessel walls may lead to stroke, brain hemorrhage, or dementia); as well as diseases, disorders or conditions co-morbid with (meaning occurring in association with) AD or with any of the above diseases, disorders or conditions, such as Parkinson's disease and epilepsy.

The term "dementia" as used herein refers to a decline or a progressive decline in cognitive function due to damage or disease in the brain beyond what might be expected from normal aging. The term "cognitive function" refers to the intellectual processes resulting in an understanding, perception, or awareness of one's ideas as well as the ability to perform mental tasks, such as thinking, learning, judging, remembering, computing, controlling motor functions, and the like.

As used herein the term "treating" includes abrogating, substantially inhibiting, slowing or reversing the progression of a disease, condition, or disorder, substantially ameliorating clinical or aesthetical symptoms of a condition, substantially preventing the appearance of clinical or aesthetical symptoms of a disease, condition, or disorder, and protecting from harmful or annoying stimuli.

The term "disease" or "disorder" as used herein refers to an impairment of health or a condition of abnormal functioning. The term "syndrome," as used herein, refers to a pattern of symptoms indicative of some disease or condition. The term "injury," as used herein, refers to damage or harm to a structure or function of the body caused by an outside agent or force, which may be physical or chemical. The term "condition", as used herein, refers to a variety of health states and is meant to include disorders or diseases caused by any underlying mechanism or disorder, injury, and the promotion of healthy tissues and organs.

The term "subject" as used herein includes animal species of mammalian origin, including humans. It further includes cells and tissues derived from these species.

Accumulation of amyloid peptide in the disease, disorder or condition may occur extracellularly, meaning located or occurring outside a cell or cells. In a further embodiment, the accumulation of amyloid peptide is in the central nervous system (CNS) of the subject, and may be either in the brain or on cerebral blood vessels walls.

In one aspect, the method of the present invention comprises the step of administering to a subject susceptible to or having a disease, disorder or condition resulting from accumulation of an amyloid peptide a composition comprising (i) a therapeutically effective amount of leptin, a leptin mimic, a leptin derivative, or a leptin agonist, and (ii) a pharmaceutically acceptable carrier, and thereby modulating accumulation of the amyloid peptide. As used herein, the term "modulate" or "modulating" refers to adjusting, changing, or manipulating the function or status of amyloid peptide accumulation. Such modulation may be any change in the rate of accumulation, including an undetectable change.

In another embodiment of the method of the present invention, the method comprises monitoring circulating levels of amyloid peptide. Such monitoring may be performed one or more times at any point, i.e., before, during, or after, administration of leptin to a subject. Methods for monitoring include measuring leptin levels detected in a sample of cerebrospinal fluid or blood collected from the subject.

Figure 2:
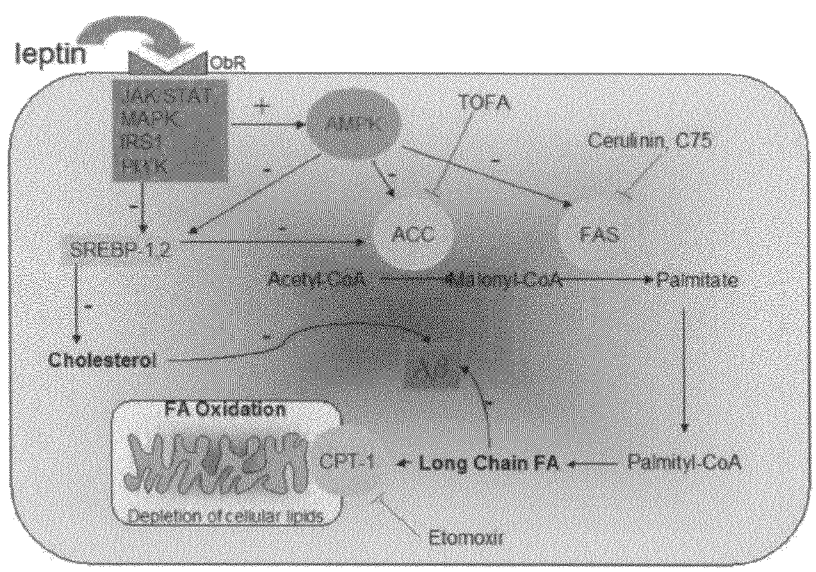
FIG. 2 shows pathways related to or affected by leptin, leading to inhibition of lipogenesis and stimulation of lipolysis, inhibiting Aβ production.

The terms "leptin mimic, leptin mimetic or leptin peptidomimetic" are used interchangeably herein to refer to a leptin derivative comprising a functional domain of the leptin protein, alone or in combination with another molecule, which will produce a biological effect, namely the effect of modulating amyloid peptide levels in a subject. More specifically, a peptidomimetic is a compound containing non-peptidic structural elements capable of mimicking or antagonizing (meaning neutralizing or counteracting) the biological action(s) of a natural parent peptide. Particularly useful for the present invention is a peptidomimetic incorporating the portion of leptin mediating activity, such as decreasing amyloid peptide levels, that is of a size small enough to penetrate the blood-brain barrier. Likewise, a leptin agonist is a compound capable of activating the leptin receptor and/or downstream effectors (see FIG. 2) and modulating amyloid peptide levels in a subject. Moreover, an activator of AMP-dependent protein kinase (AMPK) may have anti-amyloidogenic activity, based on AMPK's ability to promote lipolysis and inhibit lipogenesis upon activation. For example, phenformin and 5-aminoimidazole-4-carboxamide riboside (AICAR) are two drugs widely used to activate AMPK experimentally (King et al. *Biochem. Pharmacol.* 71:1637-47 (2006)). In addition, the antidiabetic drugs metformin and rosiglitazone may also exert some of their pharmacological actions through AMPK.

The terms "blood brain barrier" or "blood-CSF barrier" are used interchangeably herein to describe naturally-occurring systems for excluding substances from the brain and for transporting substances from blood to CSF or brain and vice versa to preserve homeostasis in the nervous system. The barriers facilitate entry of necessary metabolites, but block entry or facilitate removal of unnecessary metabolites or toxic substances. For any solute (i.e., a substance dissolved in and by a solvent), the efficacy of the exclusion or the transport is determined by morphological and functional characteristics of the brain and spinal cord capillaries and by the biochemical and biophysical characteristics of the solute. The barrier systems include carrier-mediated transport systems. Since lipid solubility enhances the transport of substances, ionized polar compounds enter the brain slowly unless there is a specific transport system for them.

Also useful according to the present invention is a leptin blocker; mimic, mimetic or peptidomimetic of a leptin blocker, such as a leptin-binding protein; or a leptin antagonist, which increases amyloid peptide levels. Also, compounds capable of inhibiting AMPK (e.g., compound C) can have leptin blocking properties. For example, and without limitation, such blockers or inhibitors are useful in providing an experimental approach to accelerate AD-like pathology in existing animal models of AD, and for in vitro experimental approaches.

The term "derivative" as used herein refers to an amino acid sequence produced from a leptin-derived peptide, either directly or by modification or partial substitution of the leptin-derived peptide. For example, and without limitation, derivatives of leptin include truncated and fusion leptin products (see infra).

The administered composition according to the present invention may further comprise a therapeutically effective amount of one or more lipolytic/antilipogenic compounds. The term "lipolytic compound" as used herein refers to a compound whose activity pertains to, is characterized by, or causes lipolysis (meaning the disintegration or splitting of fats). The term "antilipogenic compound" as used herein refers to a compound whose activity pertains to, is characterized by, or causes inhibition of lipid synthesis. In a preferred embodiment, the lipolytic/antilipogenic compound may be an acetyl CoA carboxylase inhibitor (such as 5-(tetraecyloxyl-2-furoic acid (TOFA)), a fatty acid synthase inhibitor (such as cerulenin), an acetyl CoA carboxylase inhibitor and a fatty acid synthase inhibitor, or an AMPK activator. In addition, the administered composition may be used in conjunction with other pharmaceuticals.

Furthermore, if the subject in need of treatment according to the method of the present invention has indications of other complications, such as cardiovascular disease, diabetes, or is a carrier of the apoE ϵ4 allele, the subject also may be instructed to follow additional varied treatment regimens. As used herein the term "allele" refers to an alternative DNA coding of the same gene occupying a given gene locus. The ϵ4 allele of the apoE gene likely constitutes a major risk factor for amnyloid β peptide accumulation and late-onset AD. One such regimen may be to follow a low-fat diet in combination with treatments described herein.

In another aspect, the present invention provides a method of modulating amyloid peptide accumulation in a subject comprising interfering with (meaning affecting or disrupting) at least one step in at least one metabolic or signaling pathway associated with leptin. The metabolic pathways or signaling pathways associated with leptin include, but are not limited to, the amyloidogenic pathways (which lead to generation of the Aβ peptide), the LRP pathway (which leads to endocytosis/clearance of the Aβ peptide), the insulin degrading pathway (which leads to degradation of the Aβ peptide), and any other pathway(s) affected by, or associated with, leptin. (See FIG. 2 for signaling pathways associated with leptin.)

Figure 1A:
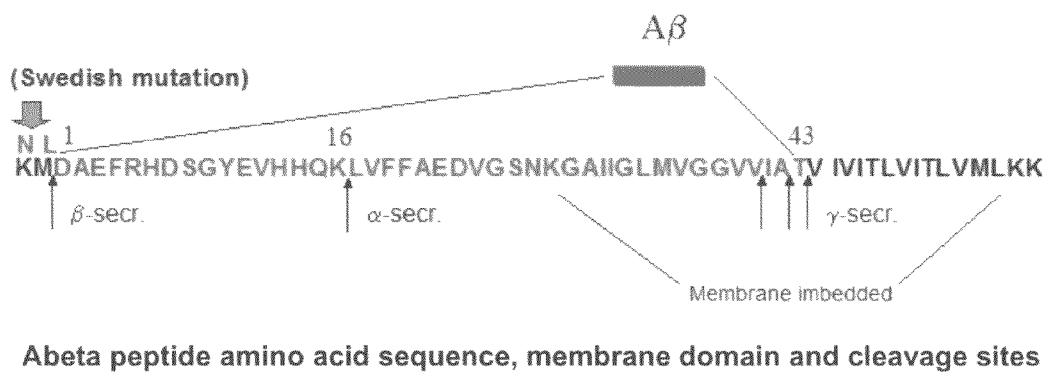
FIG. 1*a* shows the amino acid sequence, cleavage sites and membrane domain of Aβ.
Figure 1B:
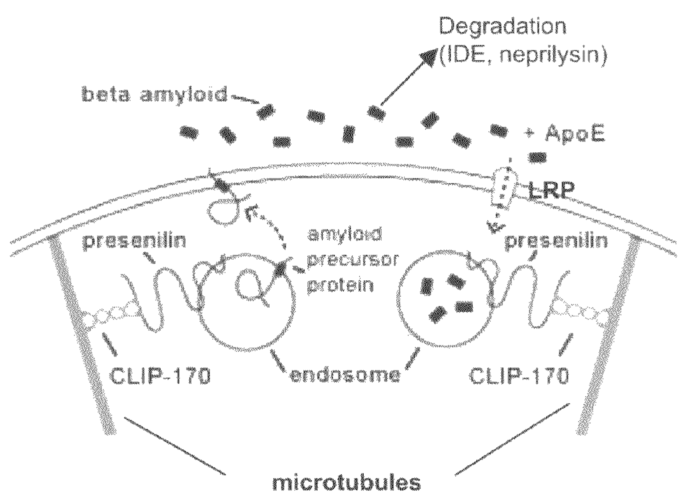
FIG. 1*b* shows mechanisms of Aβ production and clearance.
Figure 3:
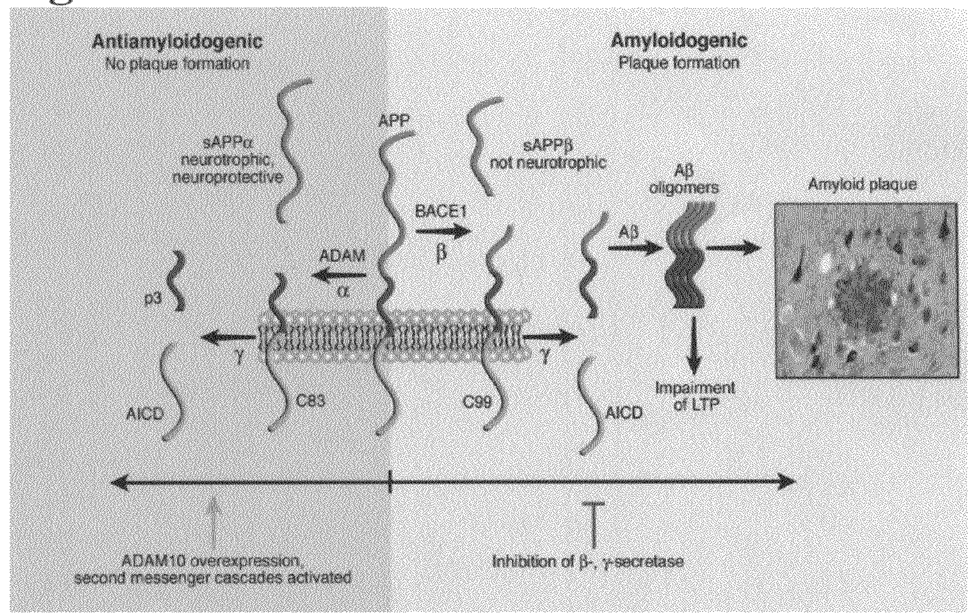
FIG. 3 shows the amyloidogenic and anti-amyloidogenic pathways (from Lichtenthaler, S. F. and Haass, C., *J. Clin. Invest.* 113:1384-1387 (2004)).

The term "amyloidogenic pathway" as used herein refers to the cellular mechanisms by which APP is proteolytically processed to generate amyloid-β, as shown in FIGS. 1 and 3. APP is proteolytically processed either through the amyloidogenic pathway or the antiamyloidogenic pathway. In the amyloidogenic pathway, consecutive cleavage of APP by β- and γ-secretase generates Aβ. In the amyloidogenic pathway, cleavage of APP by the protease β-secretase (BACϵ1) occurs at the N-terminus of the Aβ domain to yield the secreted sAPPβ (SEQ ID NO:7) as well as a C-terminal fragment of APP of 99 amino acids (C99) (SEQ ID NO:8). C99 is further cleaved within its transmembrane domain by γ-secretase, leading to the secretion of the Aβ peptide and the generation of the APP intracellular domain (AICD). The Aβ peptide so generated is prone to aggregation. Aβ peptide oligomers are neurotoxic and lead to an impairment of long-term potentiation (LTP). Finally, large amounts of Aβ peptide are deposited in amyloid plaques, which are the characteristic pathological hallmarks of AD.

In the anti-amyloidogenic pathway, cleavage of APP by α-secretase within the Aβ peptide domain yields the neurotrophic and neuroprotective sAPPα. The α-secretase is a member of the ADAM (A Disintegrin And Metalloproteinase) family of metalloproteases. α-Cleavage of APP can be induced upon overexpression of ADAM10 or by the activation of second messenger cascades.

As used herein, the term "lipoprotein receptor related protein (LRP) pathway" refers to the pathway in neurons whereby the LDL receptor-related protein (LRP) modulates Aβ deposition. In neurons, the major apoE receptor is the LDL receptor-related protein (LRP), a large endocytic receptor that regulates proteinase and lipoprotein levels by mediating their catabolism. LRP modulates Aβ deposition by increasing its clearance and by serving as a receptor for APP, apoE, and alpha 2-macroglobulin (α2M), all of which have been genetically linked to AD. (Paula G. Ulery and Dudley K. Strickland, J Clin Invest. 106(9): 1077-1079 (2000)). It is believed that LRP is involved in the pathobiology of AD.

As used herein the term "insulin degrading pathway" refers to the pathway by which insulin-degrading enzyme (IDE), a 110-kDa metalloendopeptidase, degrades Aβ peptides.

The present invention also provides a method for diagnosing a cognitive disorder, disease, condition or precondition comprising measuring circulating leptin levels.

The present invention also provides methods of improving cognitive function in a subject in need thereof, the method comprising the step of administering to the subject (i) a composition comprising (i) leptin, a leptin mimic, a leptin derivative, a leptin agonist, an AMP-dependent protein kinase (AMPK) activator, or a leptin blocker, a mimic of a leptin blocker, a leptin antagonist, or an AMPK inhibitor and (ii) a pharmaceutically acceptable carrier to the subject. As used herein, the term "cognitive function" is as defined in above to refer to the intellectual processes resulting in an understanding, perception, or awareness of one's ideas as well as the ability to perform mental tasks, such as thinking, learning, judging, remembering, computing, controlling motor functions, and the like. The expression "resilience of cognitive function" refers to the ability of functional elements of cognitive function to resist deterioration over time. As used herein, the term "cognitive function enhancing amount" refers to that amount of the compositions of the present invention that will noticeably impact the ability to perform mental tasks, as measured by tests for memory, computation, attention, or other mental or cognitive attribute, or as suggested by an individual's perception of his or her abilities in these realms.

According to the present invention, the compositions of the invention may be administered orally, buccally, parenterally, intranasally, rectally, or topically.

The compositions of the present invention may be in a form suitable for oral use, for example, as tablets, troches, lozenges, aqueous or oily suspensions, dispersible powders or granules, emulsions, hard or soft capsules or syrups or elixirs. As used herein, the terms "oral" or "orally" refer to the introduction into the body by mouth whereby absorption occurs in one or more of the following areas of the body: the mouth, stomach, small intestine, lungs (also specifically referred to as inhalation), and the small blood vessels under the tongue (also specifically referred to as sublingually). Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient(s) in admixture with non-toxic pharmaceutically-acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch or alginic acid; binding agents, for example, starch, gelatin or acacia; and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They also may be coated for controlled release.

Compositions of the present invention also may be formulated for oral use as hard gelatin capsules, where the active ingredient(s) is(are) mixed with an inert solid diluent, for example, calcium carbonate, calcium phosphate or kaolin, or soft gelatin capsules wherein the active ingredient(s) is (are) mixed with water or an oil medium, for example, peanut oil, liquid paraffin, or olive oil.

The compositions of the present invention may be formulated as aqueous suspensions wherein the active ingredient(s) is (are) in admixture with excipients suitable for the manufacture of aqueous suspensions. Such excipients are suspending agents, for example, sodium carboxymethylcellulose, methylcellulose, hydroxy-propylmethylcellulose, sodium alginate, polyvinylpyrrolidone, gum tragacanth, and gum acacia; dispersing or wetting agents may be a naturally-occurring phosphatide such as lecithin, or condensation products of an alkylene oxide with fatty acids, for example, polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions also may contain one or more coloring agents, one or more flavoring agents, and one or more sweetening agents, such as sucrose or saccharin.

Compositions of the present invention may be formulated as oily suspensions by suspending the active ingredient in a vegetable oil, for example arachis oil, olive oil, sesame oil or coconut oil, or in a mineral oil, such as liquid paraffin. The oily suspensions may contain a thickening agent, for example, beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Compositions of the present invention may be formulated in the form of dispersible powders and granules suitable for preparation of an aqueous suspension by the addition of water. The active ingredient in such powders and granules is provided in admixture with a dispersing or wetting agent, suspending agent, and one or more preservatives. Suitable dispersing or wetting agents and suspending agents are exemplified by those already mentioned above. Additional excipients, or example, sweetening, flavoring and coloring agents also may be present.

The compositions of the invention also may be in the form of an emulsion. An emulsion is a two-phase system prepared by combining two immiscible liquid carriers, one of which is disbursed uniformly throughout the other and consists of globules that have diameters equal to or greater than those of the largest colloidal particles. The globule size is critical and must be such that the system achieves maximum stability. Usually, separation of the two phases will not occur unless a third substance, an emulsifying agent, is incorporated. Thus, a basic emulsion contains at least three components, the two immiscible liquid carriers and the emulsifying agent, as well as the active ingredient. Most emulsions incorporate an aqueous phase into a non-aqueous phase (or vice versa). However, it is possible to prepare emulsions that are basically non-aqueous, for example, anionic and cationic surfactants of the non-aqueous immiscible system glycerin and olive oil. Thus, the compositions of the invention may be in the form of an oil-in-water emulsion. The oily phase may be a vegetable oil, for example, olive oil or arachis oil, or a mineral oil, for example a liquid paraffin, or a mixture thereof. Suitable emulsifying agents may be naturally-occurring gums, for example, gum acacia or gum tragacanth, naturally-occurring phosphatides, for example soy bean, lecithin, and esters or partial esters derived from fatty acids and hexitol anhydrides, for example sorbitan monooleate, and condensation products of the partial esters with ethylene oxide, for example, polyoxyethylene sorbitan monooleate. The emulsions also may contain sweetening and flavoring agents.

The compositions of the invention also may be formulated as syrups and elixirs. Syrups and elixirs may be formulated with sweetening agents, for example, glycerol, propylene glycol, sorbitol or sucrose. Such formulations also may contain a demulcent, a preservative, and flavoring and coloring agents. Demulcents are protective agents employed primarily to alleviate irritation, particularly mucous membranes or abraded (meaning torn or cut) tissues. A number of chemical substances possess demulcent properties. These substances include the alginates, mucilages, gums, dextrins, starches, certain sugars, and polymeric polyhydric glycols. Others include acacia, agar, benzoin, carbomer, gelatin, glycerin, hydroxyethyl cellulose, hydroxypropyl cellulose, hydroxypropyl methylcellulose, propylene glycol, sodium alginate, tragacanth, hydrogels and the like.

For buccal administration, the compositions of the present invention may take the form of tablets or lozenges formulated in a conventional manner.

The compositions of the present invention may be in the form of a sterile injectable aqueous or oleaginous suspension. The term "parenteral" as used herein refers to introduction into the body by way of an injection (i.e., administration by injection), including, for example, subcutaneously (i.e., an injection beneath the skin), intramuscularly (i.e., an injection into a muscle); intravenously (i.e., an injection into a vein), intrathecally (i.e., an injection into the space around the spinal cord), intrasternal injection, or infusion techniques. A parenterally administered composition of the present invention is delivered using a needle, e.g., a surgical needle. The term "surgical needle" as used herein, refers to any needle adapted for delivery of fluid (i.e., capable of flow) compositions of the present invention into a selected anatomical structure. Injectable preparations, such as sterile injectable aqueous or oleaginous suspensions, may be formulated according to the known art using suitable dispersing or wetting agents and suspending agents.

The sterile injectable preparation also may be a sterile injectable solution or suspension in a nontoxic parenterally acceptable diluent or solvent, for example, as a solution in 1,3-butanediol. A solution generally is considered as a homogeneous mixture of two or more substances; it is frequently, though not necessarily, a liquid. In a solution, the molecules of the solute (or dissolved substance) are uniformly distributed among those of the solvent. A suspension is a dispersion (mixture) in which a finely-divided species is combined with another species, with the former being so finely divided and mixed that it doesn't rapidly settle out. In everyday life, the most common suspensions are those of solids in liquid water. Among the acceptable vehicles and solvents that may be employed are water, Ringer's solution, and isotonic sodium chloride solution. In addition, sterile, fixed oils are conventionally employed as a solvent or suspending medium. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/or dextran. Optionally, the suspension may also contain stabilizers.

The compositions of the present invention may be in the form of a dispersible dry powder for delivery by inhalation or insufflation (either through the mouth or through the nose). Dry powder compositions may be prepared by processes known in the art, such as lyophilization and jet milling, as disclosed in International Patent Publication No. WO 91/16038 and as disclosed in U.S. Pat. No. 6,921,527, the disclosures of which are incorporated by reference. Spray drying, for example, is a process in which a homogeneous aqueous mixture of drug and the carrier is introduced via a nozzle (e.g., a two fluid nozzle), spinning disc or an equivalent device into a hot gas stream to atomize the solution to form fine droplets. The aqueous mixture may be a solution, suspension, slurry, or the like, but needs to be homogeneous to ensure uniform distribution of the components in the mixture and ultimately the powdered composition. The solvent, generally water, rapidly evaporates from the droplets producing a fine dry powder having particles from about 1 μm to 5 μm in diameter. The spray drying is done under conditions that result in a substantially amorphous powder of homogeneous constitution having a particle size that is respirable, a low moisture content and flow characteristics that allow for ready aerosolization. Preferably the particle size of the resulting powder is such that more than about 98% of the mass is in particles having a diameter of about 10 μm or less with about 90% of the mass being in particles having a diameter less than 5 μm. Alternatively, about 95% of the mass will have particles with a diameter of less than 10 μm with about 80% of the mass of the particles having a diameter of less than 5 μm. Dry powder compositions also may be prepared by lyophilization and jet milling, as disclosed in International Patent Publication No. WO 91/16038, the disclosure of which are incorporated by reference.

The term "dispersibility" or "dispersible" means a dry powder having a moisture content of less than about 10% by weight (% w) water, usually below about 5% w and preferably less than about 3% w; a particle size of about 1.0-5.0 μm mass median diameter (MMD), usually 1.0-4.0 μm MMD, and preferably 1.0-3.0 μm MMD; a delivered dose of about >30%, usually >40%, preferably >50%, and most preferred >60%; and an aerosol particle size distribution of about 1.0-5.0 μm mass median aerodynamic diameter (MMAD), usually 1.5-4.5 μm MMAD, and preferably 1.5-4.0 μm MMAD. Methods and compositions for improving dispersibility are disclosed in U.S. application Ser. No. 08/423,568, filed Apr. 14, 1995, the disclosure of which is hereby incorporated by reference.

The term "powder" means a composition that consists of finely dispersed solid particles that are free flowing and capable of being readily dispersed in an inhalation device and subsequently inhaled by a subject so that the particles reach the lungs to permit penetration into the alveoli. Thus, the powder is said to be "respirable." Preferably the average particle size is less than about 10 microns (μm) in diameter with a relatively uniform spheroidal shape distribution. More preferably the diameter is less than about 7.5 μm and most preferably less than about 5.0 μm. Usually the particle size distribution is between about 0.1 μm and about 5 μm in diameter, particularly about 0.3 μm to about 5 μm.

The term "dry" means that the composition has a moisture content such that the particles are readily dispersible in an inhalation device to form an aerosol. This moisture content is generally below about 10% by weight (% w) water, usually below about 5% w and preferably less than about 3% w.

The amount of the pharmaceutically acceptable carrier is that amount needed to provide the necessary stability, dispersibility, consistency and bulking characteristics to ensure a uniform pulmonary delivery of the composition to a subject in need thereof. Numerically the amount may be from about 0.05% w to about 99.95% w, depending on the activity of the drug being employed. Preferably about 5% w to about 95% will be used. The carrier may be one or a combination of two or more pharmaceutical excipients, but generally will be substantially free of any "penetration enhancers." Penetration enhancers are surface active compounds which promote penetration of a drug through a mucosal membrane or lining and are proposed for use in intranasal, intrarectal, and intravaginal drug formulations. Exemplary penetration enhancers include bile salts, e.g., taurocholate, glycocholate, and deoxycholate; fusidates, e.g., taurodehydrofusidate; and biocompatible detergents, e.g., Tweens, Laureth-9, and the like. The use of penetration enhancers in formulations for the lungs, however, is generally undesirable because the epithelial blood barrier in the lung can be adversely affected by such surface active compounds. The dry powder compositions of the present invention are readily absorbed in the lungs without the need to employ penetration enhancers.

The types of pharmaceutical excipients that are useful as carriers for pulmonary delivery include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable for pulmonary delivery include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-β-cyclodextrin; and polysaccharides, such as raffinose, maltodextrins, dextrans, and the like; alditols, such as mannitol, xylitol, and the like. A preferred group of carbohydrates includes lactose, trehalose, raffinose, maltodextrins, and mannitol. Suitable polypeptides include aspartame. Amino acids include alanine and glycine, with glycine being preferred.

Additives, which are minor components of the composition for pulmonary delivery, may be included for conformational stability during spray drying and for improving dispersibility of the powder. These additives include hydrophobic amino acids such as tryptophan, tyrosine, leucine, phenylalanine, and the like.

For delivery by inhalation or insufflation, the composition of the present invention is placed within a suitable dosage receptacle in an amount sufficient to provide a subject with a unit dosage treatment. The dosage receptacle is one that fits within a suitable inhalation device to allow for the aerosolization of the dry powder composition by dispersion into a gas stream to form an aerosol and then capturing the aerosol so produced in a chamber having a mouthpiece attached for subsequent inhalation by a subject in need of treatment. Such a dosage receptacle includes any container enclosing the composition known in the art such as gelatin or plastic capsules with a removable portion that allows a stream of gas (e.g., air) to be directed into the container to disperse the dry powder composition. Such containers are exemplified by those shown in U.S. Pat. No. 4,227,522; U.S. Pat. No. 4,192,309; and U.S. Pat. No. 4,105,027. Suitable containers also include those used in conjunction with Glaxo's Ventolin® Rotohaler brand powder inhaler or Fison's Spinhaler® brand powder inhaler. Another suitable unit-dose container which provides a superior moisture barrier is formed from an aluminum foil plastic laminate. The pharmaceutical-based powder is filled by weight or by volume into the depression in the formable foil and hermetically sealed with a covering foil-plastic laminate. Such a container for use with a powder inhalation device is described in U.S. Pat. No. 4,778,054 and is used with Glaxo's Diskhaler® (U.S. Pat. Nos. 4,627,432; 4,811,731; and 5,035,237). All of these references are incorporated herein by reference.

The compositions of the invention may be used in the form of drops or sprays (e.g., a nasal spray, aerosol spray, or pump spray) or other vehicles for nasal administration (intranasal delivery). Aerosol spray preparations can be contained in a pressurized container with a suitable propellant such as a hydrocarbon propellant. Pump spray dispensers can dispense a metered dose or a dose having a specific particle or droplet size. Any dispensing device can be arranged to dispense only a single dose, or a multiplicity of doses. More generally, compositions of the invention, especially those formulated for intranasal administration, can also be provided as solutions, suspensions, or viscous compositions (e.g., gels, lotions, creams, or ointments).

The compositions of the present invention may be in the form of suppositories for rectal administration of the composition. "Rectal" or "rectally" as used herein refers to introduction into the body through the rectum where absorption occurs through the walls of the rectum. These compositions can be prepared by mixing the drug with a suitable nonirritating excipient such as cocoa butter and polyethylene glycols which are solid at ordinary temperatures but liquid at the rectal temperature and will therefore melt in the rectum and release the drug. When formulated as a suppository the compositions of the invention may be formulated with traditional binders and carriers, such as triglycerides.

The term "topical" refers to administration of an inventive composition at, or immediately beneath, the point of application. The phrase "topically applying" describes application onto one or more surfaces(s) including epithelial surfaces. Although topical administration, in contrast to transdermal administration, generally provides a local rather than a systemic effect, as used herein, unless otherwise stated or implied, the terms topical administration and transdermal administration are used interchangeably. For the purpose of this application, topical applications shall include mouthwashes and gargles.

Topical administration may also involve the use of transdermal administration such as transdermal patches or iontophoresis devices which are prepared according to techniques and procedures well known in the art. The terms "transdermal delivery system," transdermal patch" or "patch" refer to an adhesive system placed on the skin to deliver a time released dose of a drug(s) by passage from the dosage form through the skin to be available for distribution via the systemic circulation. Transdermal patches are a well-accepted technology used to deliver a wide variety of pharmaceuticals, including, but not limited to, scopolamine for motion sickness, nitroglycerin for treatment of angina pectoris, clonidine for hypertension, estradiol for post-menopausal indications, and nicotine for smoking cessation.

Patches suitable for use in the present invention include, but are not limited to, (1) the matrix patch; (2) the reservoir patch; (3) the multi-laminate drug-in-adhesive patch; and (4) the monolithic drug-in-adhesive patch; Transdermal and Topical Drug Delivery Systems, pp. 249-297 (Tapash K. Ghosh et al. eds., 1997), hereby incorporated herein by reference. These patches are well known in the art and generally available commercially.

In some embodiments, the compositions of the present invention may be formulated with an excipient, vehicle or carrier selected from solvents, suspending agents, binding agents, fillers, lubricants, disintegrants, and wetting agents/surfactants/solubilizing agents. The terms "excipient", "vehicle", or "carrier" refer to substances that facilitate the use of, but do not deleteriously react with, the active compound(s) when mixed with it. The term "active" refers to the ingredient, component or constituent of the compositions of the present invention responsible for the intended therapeutic effect. Carriers must be of sufficiently high purity and of sufficiently low toxicity to render them suitable for administration to the subject being treated. The carrier can be inert, or it can possess pharmaceutical benefits.

The carrier can be liquid or solid and is selected with the planned manner of administration in mind to provide for the desired bulk, consistency, etc., when combined with an active and the other components of a given composition. Typical pharmaceutical carriers include, but are not limited to, binding agents (including, but not limited to pregelatinized maize starch, polyvinylpyrrolidone or hydroxypropyl methylcellulose); fillers (including but not limited to lactose and other sugars, microcrystalline cellulose, pectin, gelatin, calcium sulfate, ethyl cellulose, polyacrylates or calcium hydrogen phosphate.); lubricants (including, but not limited to magnesium stearate, talc, silica, sollidal silicon dioxide, stearic acid, metallic stearates, hydrogenated vegetable oils, corn starch, polyethylene glycols, sodium benzoate, sodium acetate); disintegrants (including but not limited to starch, sodium starch glycolate) and wetting agents (including but not limited to sodium lauryl sulfate). Additional suitable carriers for the compositions of the present invention include, but are not limited to, water, salt solutions, alcohol, vegetable oils, polyethylene glycols, gelatin, lactose, amylose, magnesium stearate, talc, silicic acid, viscous paraffin, perfume oil; fatty acid monoglycerides and diglycerides, petroethral fatty acid esters, hydroxymethylcellulose, polyvinylpyrrolidone, and the like. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds.

The term "pharmaceutically acceptable carrier" as used herein refers to any substantially non-toxic carrier conventionally useful for administration of pharmaceuticals in which the active component will remain stable and bioavailable. In some embodiments, the pharmaceutically acceptable carrier of the compositions of the present invention include a release agent such as a sustained release or delayed release carrier. In such embodiments, the carrier can be any material capable of sustained or delayed release of the leptin peptide active ingredient to provide a more efficient administration, resulting in less frequent and/or decreased dosage of the active ingredient, ease of handling, and extended or delayed effects. Non-limiting examples of such carriers include liposomes, microsponges, microspheres, or microcapsules of natural and synthetic polymers and the like. Liposomes may be formed from a variety of phospholipids such as cholesterol, stearylamines or phosphatidylcholines.

The therapeutically active leptin, leptin mimic, leptin agonist, or leptin derivative peptides, as well as leptin blockers and leptin antagonists of the present invention can be formulated per se or in salt form. The term "pharmaceutically acceptable salts" refers to nontoxic salts of the peptides of the present invention. The peptide salts which can be used for the invention are pharmaceutically acceptable salts of organic acids or pharmaceutically acceptable salts of inorganic acids. Examples of such pharmaceutically acceptable peptide salts include, but are not limited to, those formed with free amino groups such as those derived from hydrochloric, phosphoric, sulfuric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Additional compositions of the present invention can be prepared readily using technology is known in the art, such as that which is described in Remington's Pharmaceutical Sciences, 18th or 19th editions, published by the Mack Publishing Company of Easton, Pa., which is incorporated herein by reference.

In some embodiments, the compositions of the present invention can further include one or more compatible active ingredients aimed at providing the composition with another pharmaceutical effect in addition to that provided by a leptin, leptin mimic peptide or a derivative thereof. "Compatible" as used herein means that the active ingredients of such a composition are capable of being combined with each other in such a manner so that there is no interaction that would substantially reduce the efficacy of each active ingredient or the composition under ordinary use conditions. In another aspect of the present invention, the composition also may be administered serially or in combination with other compositions for treating diseases, conditions or disorders resulting from accumulation of amyloid peptides. For example, without limitation, such other compositions may include monoclonal antibodies (such as monoclonal anti-β-Amyloids and monoclonal anti-β-secretases); and anti-inflammatory compounds (including, but not limited to nonsteroidal anti-inflammatory drugs (NSAIDs), such as ibuprofen, indomethacin, and flurbiprofen). Anti-inflammatory compounds have been shown to direct Aβ-lowering properties in cell cultures as well as in transgenic models of AD-like amyloidosis.

A composition of the present invention, alone or in combination with other active ingredients, may be administered to a subject in a single dose or multiple doses over a period of time. As used herein, the terms "therapeutically effective amounts," and "pharmaceutically effective amounts" are used interchangeably to refer to the amount of the composition of the invention that results in a therapeutic or beneficial effect, including a subject's perception of health or general well-being, following its administration to a subject. Additionally, the terms "therapeutically effective amounts" and "pharmaceutically effective amounts" include prophylactic or preventative amounts of the compositions of the present invention. In prophylactic or preventative applications of the present invention, pharmaceutical compositions or medicaments are administered to a patient susceptible to, or otherwise at risk of, a disease, disorder or condition resulting from accumulation of an amyloid peptide in an amount sufficient to eliminate or reduce the risk, lessen the severity, or delay the onset of the disease, disorder or condition, including biochemical, histologic and/or behavioral symptoms of the disease, disorder or condition, its complications and intermediate pathological phenotypes presenting during development of the disease, disorder or condition.

The concentration of the active substance is selected so as to exert its therapeutic effect, but low enough to avoid significant side effects within the scope and sound judgment of the skilled artisan. The effective amount of the composition may vary with the age and physical condition of the biological subject being treated, the severity of the condition, the duration of the treatment, the nature of concurrent therapy, the specific compound, composition or other active ingredient employed, the particular carrier utilized, and like factors. Those of skill in the art can readily evaluate such factors and, based on this information, determine the particular effective concentration of a composition of the present invention to be used for an intended purpose. Additionally, in therapeutic applications of the present invention, compositions or medicants are administered to a patient suspected of, having, or already suffering from, such a disease, disorder or condition in an amount sufficient to cure, or at least partially arrest, the symptoms of the disease, disorder or condition, including its complications and intermediate pathological phenotypes in development of the disease, disorder or condition. In some methods, administration of the composition of the present invention reduces or eliminates cognitive impairment in patients that have not yet developed characteristic pathology of the disease, disorder or condition.

An amount adequate to accomplish therapeutic or prophylactic treatment is defined herein as a therapeutically-effective dose. In both prophylactic and therapeutic regimes, an amount of the compositions of the present invention is usually administered in several dosages until a sufficient beneficial response has been achieved. Typically, the response is monitored and repeated dosages are given if the response starts to wane. A skilled artisan can determine a pharmaceutically effective amount of the inventive compositions by determining the dose in a dosage unit (meaning unit of use) that elicits a given intensity of effect, hereinafter referred to as the "unit dose." The term "dose-intensity relationship" refers to the manner in which the intensity of effect in an individual recipient relates to dose. The intensity of effect generally designated is 50% of maximum intensity. The corresponding dose is called the 50% effective dose or individual ED50. The use of the term "individual" distinguishes the ED50 based on the intensity of effect as used herein from the median effective dose, also abbreviated ED50, determined from frequency of response data in a population. "Efficacy" as used herein refers to the property of the compositions of the present invention to achieve the desired response, and "maximum efficacy" refers to the maximum achievable effect. The amount of compounds in the compositions of the present invention which will be effective in the treatment of a particular disorder or condition will depend on the nature of the disorder or condition, and can be determined by standard clinical techniques. (See, for example, Goodman and Gilman's THE PHARMACOLOGICAL BASIS OF THERAPEUTICS, Joel G. Harman, Lee E. Limbird, Eds.; McGraw Hill, N.Y., 2001; THE PHYSICIAN'S DESK REFERENCE, Medical Economics Company, Inc., Oradell, N.J., 1995; and DRUG FACTS AND COMPARISONS, FACTS AND COMPARISONS, INC., St. Louis, Mo., 1993). The precise dose to be employed in the formulation will also depend on the route of administration, and the seriousness of the disease or disorder, and should be decided according to the judgment of the practitioner and each patient's circumstances. Various administration patterns will be apparent to those skilled in the art.

The dosage ranges for the administration of the compositions of the present invention are those large enough to produce the desired therapeutic effect. Preferably, the therapeutically effective amount of the compositions of the present invention is administered one or more times per day on a regular basis. A typical dose administered to a subject is between about 0.01 mg of the composition per kg (of body weight) per day and about 0.5 mg of the composition per kg (of body weight) per day. For example, without limitation, the minimum dose of the composition is contemplated as about 0.01 mg/kg/day, about 0.025 mg/kg/day, about 0.05 mg/kg/day, about 0.075 mg/kg/day, about 0.08 mg/kg/day, about 0.1 mg/kg/day, about 0.125 mg/kg/day, about 0.15 mg/kg/day, about 0.175 mg/kg/day, about 0.2 mg/kg/day, about 0.225 mg/kg/day, about 0.25 mg/kg/day, about 0.275 mg/kg/day, about 0.3 mg/kg/day, about 0.325 mg/kg/day, about 0.35 mg/kg/day, about 0.375 mg/kg/day, about 0.4 mg/kg/day, about 0.45 mg/kg/day, about 0.475 mg/kg/day, or about 0.5 mg/kg/day and the maximum dose is contemplated as about 0.5 mg/kg/day, about 0.475 mg/kg/day, about 0.45 mg/kg/day, about 0.4 mg/kg/day, about 0.375 mg/kg/day, about 0.35 mg/kg/day, about 0.325 mg/kg/day, about 0.3 mg/kg/day, about 0.275 mg/kg/day, about 0.25 mg/kg/day, bout 0.225 mg/kg/day, about 0.2 mg/kg/day, about 0.175 mg/kg/day, about 0.15 mg/kg/day, about 0.125 mg/kg/day, about 0.1 mg/kg/day, about 0.08 mg/kg/day, about 0.075 mg/kg/day, about 0.05 mg/kg/day, about 0.025 mg/kg/day, or about 0.01 mg/kg/day. In some embodiments of the invention in humans, the dose may be about 0.01 mg to about 0.3 mg of the composition per kg (of body weight) per day, and in other embodiments in humans, between 0.01 and 0.08 mg of the composition per kg (of body weight) per day.

Those skilled in the art will recognize that initial indications of the appropriate therapeutic dosage of the compositions of the invention can be determined in in vitro and in vivo animal model systems, and in human clinical trials. One of skill in the art would know to use animal studies and human experience to identify a dosage that can safely be administered without generating toxicity or other side effects. For acute treatment, it is preferred that the therapeutic dosage be close to the maximum tolerated dose. For chronic preventive use, lower dosages may be desirable because of concerns about long term effects.

The effectiveness of the compositions and methods of the present invention can be assayed by a variety of protocols. The effects of increasing cognitive flnction in a human subject can be determined by methods routine to those skilled in the art including, but not limited to, both paper and pencil, and computer tests. One of skill in the art can also directly measure amyloid peptide accumulation levels, neurofibrillary tangle formation and neurodegeneration in animal models. Furthermore, amyloid peptide may be measured in a sample of a subject's cerebrospinal fluid (CSF) obtained by spinal tap. One measure of accumulation of an amyloid peptide is an increase in levels circulating in the blood of a subject. Such levels may be measured by Sandwich Enzyme-linked-Immunoabsorbent-Assays (ELISAs), using a pair of antibodies, one for capture and the other for detection. These methods are well known by those of ordinary skill in the art.

Unless defined otherwise, all technical and scientific terms used herein have the same meaning as commonly understood by one of ordinary skill in the art to which this invention belongs. Although any methods and materials similar or equivalent to those described herein also can be used in the practice or testing of the present invention, the preferred methods and materials are now described. All publications mentioned herein are incorporated herein by reference to disclose and describe the methods and/or materials in connection with which the publications are cited.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

METHODS

Cell cultures, Treatments, Antibodies and Immunoassays. SY5Y cells (human neuroblastoma) were maintained in culture as described (Johnsingh et al., *FEBS Lett.* 465:53-8 (2000)). Primary neural cultures were obtained from ϵ16 rat embryonic cortex, as described (Shimoda et al., 1992. *Brain Res.* 586:319-31 (1992)). These were either grown as mixed cultures (Johnsingh et al., *FEBS Lett.* 465:53-8 (2000)) or grown under conditions that favor the isolation and proliferation of astrocytes (Takeshima et al., *J Neurosci.* 14:4769-79 (1994)).

Neuro2a (mouse neuroblastoma) stably transfected with hyg-sa134, a pcDNA3.1/Hygro plasmid (Invitrogen, CA) modified to express a fusion protein of secreted alkaline phosphatase (SEAP) and a fragment of APP consisting of the C-terminal 134 amino acids ("$CAPP_{134}$") (SEQ ID NO:10) were maintained in culture as described (Johnsingh et al., *J Neurosci.* 14:4769-79 (2000)) in the presence of 400 μg/ml of hygromycin. SEQ ID NO: 11 is the DNA sequence of the entire hygsa134 vector, which was derived from the pcDNA3.1/Hygro vector by genetic manipulation to insert the DNA sequences for SEAP and $CAPP_{134}$. The SEAP-CAPP cDNA insert from hyg-sa134 was also subcloned into an adenoviral vector using the Adeno Vator system (Qbiogene, Calif.). The DNA sequence for SEAP (corresponding to nucleotides 981-2441 of hyg-sa134) (SEQ ID NO: 9) is located 5' to the DNA sequence (SEQ ID NO: 12) coding for $CAPP_{134}$ (SEQ ID NO: 10).

SY5Y and hyg-sa134-Neuro2a cells were treated at 80% confluency (see below). Primary neural cultures from mouse embryos were allowed to grow for 6-12 days following plating and prior to viral infection and treatments.

About 5 μg/ml or about 10 μg/ml water-soluble cholesterol was added to cultures for 2 or 5 hours. Water soluble cholesterol (Sigma-Aldrich, MO) is a solution made of cholesterol balanced with cyclodextrin CDX (40 mg cholesterol per gr CDX). For comparison, cultures were treated with the equivalent amount of the resin alone, which leads to depletion of cholesterol in the cultures (Simons et al., *Proc Natl Acad Sci USA.* 95:6460-4 (1998)).

About 100 ng/ml or about 400 ng/ml leptin (Harbor-UCLA, CA), was added in cell culture medium for 2 or 5 h. Cells were approximately 80% confluent at the time of treatment. Peptide YY (3-36) (Phoenix Pharmaceuticals, Inc., CA), and CNTF (Sigma-Aldrich, Mo.) were added at about 25 μM or 150 μM for the same incubation periods. TOFA, etomoxir (Research Biochemicals International, MA) and cerulenin (Sigma-Aldrich, Mo.) were used as described below.

Cell lysates were used for the detection of full-length APP (SEQ ID NO: 1-SEQ ID NO: 3) and its C-terminal fragments generated by β- and α-secretase (10 kDa (SEQ ID NO: 8) and 8 kDa (SEQ ID NO: 16) respectively) as described (Johnsingh et al., *FEBS Lett.* 465:53-8 (2000)). This was performed either by $^{35}$S-[Met]/$^{35}$S-[Cys] metabolic labeling/immunoprecipitations or Western blots using a rabbit polyclonal antibody directed against the last 20 C-terminal amino acids of APP (Institute for Basic Research, NY) (Figueiredo-Pereira et al., *J Neurochem.* 72:1417-22 (1999); Johnsingh et al., *FEBS Lett.* 465:53-8. (2002)).

For the determination of Aβ peptide several methodologies also were used. SY5Y cells in culture were metabolically labeled with $^{35}$S-[Met] as described (Figueiredo-Pereira et al. *J Neurochem.* 72:1417-22 (1999)), followed by immunoprecipitation, resolution of the immunoprecipitates on SDS-PAGE, autoradiography, and densitometric analysis of the autoradiogram. Neuro2a cells were stably transfected with hyg-sa134 (K. Sambamurti, S. Carolina Medical Center, SC) and Aβ40 (SEQ ID NO: 4) plus Aβ42 (SEQ ID NO: 5) plus Aβ43 (SEQ ID NO: 6) (Total Aβ) in the medium then was quantified by sandwich ELISAs developed with 4G8 and 6 ϵ10 monoclonal antibodies (Signet, Mass.) as described (Figueiredo-Pereira et al., *J Neurochem.* 72:1417-22 (1999)). Commercially available ELISA kits (KMI Diagnostics, MN) were used for the separate determination of Aβ40 (SEQ ID NO:4) and Aβ42/43 (SEQ ID NO:5/SEQ ID NO:6) in formic acid extracts of mice brains. Flotillin was detected using monoclonal anti-flotillin-1 antibodies (BD Biosciences, CA). Actin was detected using monoclonal anti-actin antibodies (Research Diagnostics, Inc, NJ).

Leptin was detected using a rabbit polyclonal antibody raised against mouse leptin, corss-reacting with human leptin (obtained from Dr. A. F. Parlow, Harbor-UCLA, CA). Immunofluorescent confocal microscopy was performed on 2% paraformaldehyde-fixed primary neural cells. Filipin staining was performed as described (Feng et al., *Nat Cell Biol.* 5:781-92 (2003)).

Preparation of ApoE and binding with $^{125}$I-Aβ. ApoE was isolated from the conditioned media of human embryonic kidney (HEK-293) cells stably-transfected with human apoE (having the ϵ3 allele or the ϵ4 allele) cDNA (Tezapsidis et al., *FASEB J.* 17:1322-1324 (2003)). These preparations, while usually poor in lipid, are fully functional for uptake experiments. ApoE then was pre-incubated with $^{125}$I-Aβ overnight at 37° C. (Aβ/ApoE: 1/50 w/w) as described (Tezapsidis et al., *FASEB J.* 17:1322-1324 (2003)).

Aβ-uptake by SY5Y cells. Human $^{125}$I-Aβ (iodinated at Tyr-10, Amersham Biosciences, IM 294) uptake was measured following addition of 0.1 nM $^{125}$I-Aβ40 (SEQ ID NO: 4) to confluent SY5Y cells (60,000 cpm/ml) in the presence or absence of 100 ng/ml or 400 ng/ml leptin also included in a 24 h pre-incubation period. $^{125}$I-Aβ was either added alone or was previously incubated with apoϵ3. In controls, Receptor Associated Protein ("RAP", 1 μM) was added together with Aβ or the Aβ/apoE complex. RAP is an antagonist of a number of lipoprotein receptors (LaDu et al., *Neurochem Int.* 39:427-34 (2001)). After 24 h, the media were collected and subjected to scintillation counting for γ-Iradiation (Kang et al., 2000. *J Clin Invest.* 106:1159-66 (2000)). The amount of radioactivity was measured in both the trichloroacetic acid (10%) TCA pellets (representing intact Aβ) and the corresponding supernatants (representing degraded Aβ). 96.5±8.2% (mean±s.e.m., n=4 experiments, triplicate determinations) of the radioactivity found in the medium could be recovered in the TCA pellet and represented intact or oligomeric Aβ (not shown), when Aβ was pre-incubated with apoE. However, only 31.2±5.8% (n=4) of the radioactivity was recovered in the TCA pellet in the absence of apoE, suggesting that Aβ was degraded under those conditions, consistent with reports by others. This has been suggested to be due to the activity of Insulin-Degrading Enzyme (Farris et al., *Proc Natl Acad Sci USA.* 100:4162-4167 (2003)). Indeed, inclusion during the uptake of 1,10 phenanthroline, a general metalloprotease inhibitor that effectively inhibits degradation of secreted Aβ, in vitro, abolished Aβ degradation.

The amount of TCA-precipitable radioactivity in the soluble fraction of cell lysates was compared to that in the total lysates, the ratio of which was typically about 0.8 to about 0.9 (not shown), to further verify that radioactivity was reduced in the media as a reflection of Aβ uptake by the cells, rather than due to non-specific binding to the extracellular surface of membranes or oligomerization/aggregation of Aβ.

Measurement of Protein. Proteins were extracted from cells by treatment with the nonionic surfactant Igepal (SIGMA, 0.1%) and brief sonication. Protein content was determined by the Bradford method (Bradford, *Anal Biochem.* 72:248-54 (1976)).

SREBP cDNAs. Human SREBP-1 (SEQ ID NO: 17) and SREBP-2 (SEQ ID NO: 19) cDNAs were obtained by polymerase chain reaction ("PCR") using a human brain cDNA expression library as a template. Briefly, 5'-gaga ggatccaacagggcaggacacgaa-3' (linker italicized, BamHI site underlined) (SEQ ID NO: 20) was used as forward primer and 5'-gagagaattcgctgctgccaagggaca-3' (linker italicized, EcoRI site underlined) (SEQ ID NO: 21) was used as a reverse primer, generating a 1461nt fragment of human SREBP-1 (GenBank Accession No. U00968, GenInfo Identifier (GI): 409404) predicted to encode for SREBP-1 (1-445 amino acids) (SEQ ID NO: 24). The resulting 1.5-kb fragment was cloned into the BamHI and EcoRI sites of the pcDNA3.1 vector. Similarly, 5'-gagaggatccaaggttgtcgggtgtcatg-3' (linker italicized, BamHI site underlined) (SEQ ID NO: 22) was used as a forward primer and 5'-gaga gaattcgctggctcatctttgacctt-3' (linker italicized, EcoRI site underlined) (SEQ ID NO: 23) as a reverse primer, generating a 1492nt fragment of human SREBP-2 (GenBank Accession No. U02031, GI:451329), predicted to encode for SREBP-2 (1-467 amino acids) (SEQ ID NO: 25). The resulting 1.5-kb fragment was cloned into the BamHI and EcoRI sites of the pcDNA3.1 vector.

Leptin studies in mice. One year-old transgenic animals with the following genotypes were used: a) $APP_{swe}$/$PS1_{M146V}$ (double transgenic) (Holcomb et al., *Nat Med.* 4:97-100 (1998)); b) $PS1_{M46V}$ (Duff et al., *Nature.* 383:710-3 (1996)) and c) wild-type C57B1/6×SJL. SEQ ID NO: 13 is the amino acid sequence for $APP_{swe}$. A double mutation at codons 670 and 671 (APP isoform a) co-segregates with the disease in two large (probably related) early-onset Alzheimer's disease families from Sweden. Two base pair transversions (G to T, A to C) from the normal sequence predict L to N and M to L amino acid substitutions at codons 670 and 671 of the APP transcript. SEQ ID NO:14 is the amino acid sequence of PS1 in humans. SEQ ID NO: 15 is the amino acid sequence of $PS1_{M146V}$. A single mutation at codon 146 co-segregates with the disease in members of early-onset Alzheimer's disease families. A base pair change from the normal sequence predicts M to V amino acid substitution at codon 146.

Blood was withdrawn (approximately 1 ml) from deeply anaesthetized animals by cardiocentesis and mixed with 25 µl of 164 µM EDTA anticoagulant. Plasma was prepared immediately and frozen at −70° C. Plasma leptin concentrations were determined by a radioimmunoassay (RIA) (Chung et al., *Am. J Physiol.* 274:R985-R990 (1998)), using a kit from LINCO Research, Inc. (Missouri).

$APP_{swe}$ (SEQ ID NO: 13) expressing mice (Tg2576) or wild-type littermates were maintained in pathogen-free environment at 25° C. on a 12-12 h light-dark cycle. Mice were euthanized between the ages of 31 and 40 weeks. They were provided ad libidum access for up to 9 weeks (i.e., 1 week prior to leptin treatments and 8 weeks during such treatments) to a high fat diet (D12451) containing about 45% of the total calories from fat (Research Diets, NJ) or to a low fat diet (D12450B) containing about 10% of the total calories from fat. Equal number of male and female Tg2576 mice under each diet were administered leptin or a placebo (PBS) from the age of 32 wks to up to 40 wks of age. For this, mice were anaesthetized with intraperitoneal injection of ketamine (55 mg/ml) and xylazine (7-10 mg/ml) and surgically fitted with an Alzet miniosmotic pump (model 2004, Durect Co, CA) placed subcutaneously. Local subcutaneous injection of 0.5 ml of 0.5% lidocaine insured postoperative relief. Half of the mice received daily about 20 µg leptin in PBS (0.25 µl/h of 3.33 mg/ml recombinant murine leptin) and the other half were infused with PBS. Four from each group (two males and two females) were euthanized after 4 weeks treatment. Osmotic pumps were replaced in the rest and the mice then treated for a total period of 8 weeks. Wild-type littermates were also treated with leptin under high or low diet regimens. The animal protocol was reviewed and approved by the Institutional Animal Core and Use Committee (ACUC) at the Columbia University Medical Center.

For other subjects, including humans, recombinant leptin products can be prepared for use in the methods of the present invention by various methods. One such method is described in U.S. Pat. No. 6,001,968, the contents of which are incorporated by reference herein. Leptin includes, but is not limited to, recombinant human leptin (PEG-OB, Hoffman La Roche) and recombinant methionyl human leptin (Amgen). Leptin derivatives, e.g., truncated forms of leptin (see para. 33 above), useful in the present invention include: U.S. Pat. Nos. 5,552,524; 5,552,523; 5,552,522; 5,521,283; and PCT International Publication Nos. WO 96/23513; WO 96/23514; WO 96/23515; WO 96/23516; WO 96/23517; WO 96/23518; WO 96/23519; and WO 96/23520, the contents of which are incorporated by reference herein. Also leptin fusion products useful in the present invention include, but are not limited to, fc-leptin, which is a fusion peptide derived from leptin and the Fc immunoglobulin region (see U.S. Pat. No. 6,936,439 and U.S. Published Patent Application No. 20050163799, the contents of which are incorporated by reference herein). The terms "fusion protein" or "fusion product" as used herein refers to a protein created through genetic engineering from two or more proteins/peptides by creating a fusion gene (i.e., removing the stop codon from the DNA sequence of the first protein and appending the DNA sequence of the second protein in frame) so that the DNA sequence encoding the two or more proteins/peptides is expressed by a cell as a single protein.

Statistical analysis. All values are the mean±s.e.m. Variations between pairs of groups was evaluated with t-test and differences were considered significant when $p<0.05$.

Example 1

The Effects of Leptin on Aβ Production in Vitro

Human (SYSY) or mouse neuroblastoma cell-lines (Neuro2a) commonly are used to study amyloid β metabolism in vitro. Neuro2a cells are stably transfected with hyg-sa134 (SEQ ID NO: 11), a plasmid driving the expression of a recombinant fusion protein containing the human C-terminal fragment of APP of about 134 amino acids, $CAPP_{134}$ (SEQ ID NO: 10). Here, 5Y5Y or Neuro2a cultures were treated for 2 or 5 h with about 100 ng/ml or about 400 ng/ml leptin (FIG. 4*a*, 4*b*). Similarly, primary neurons from embryonic rat brain, infected with an adenovirus to direct the expression of $CAPP_{134}$ (SEQ ID NO:10) also were treated according to the same regimen.

Figure 4:
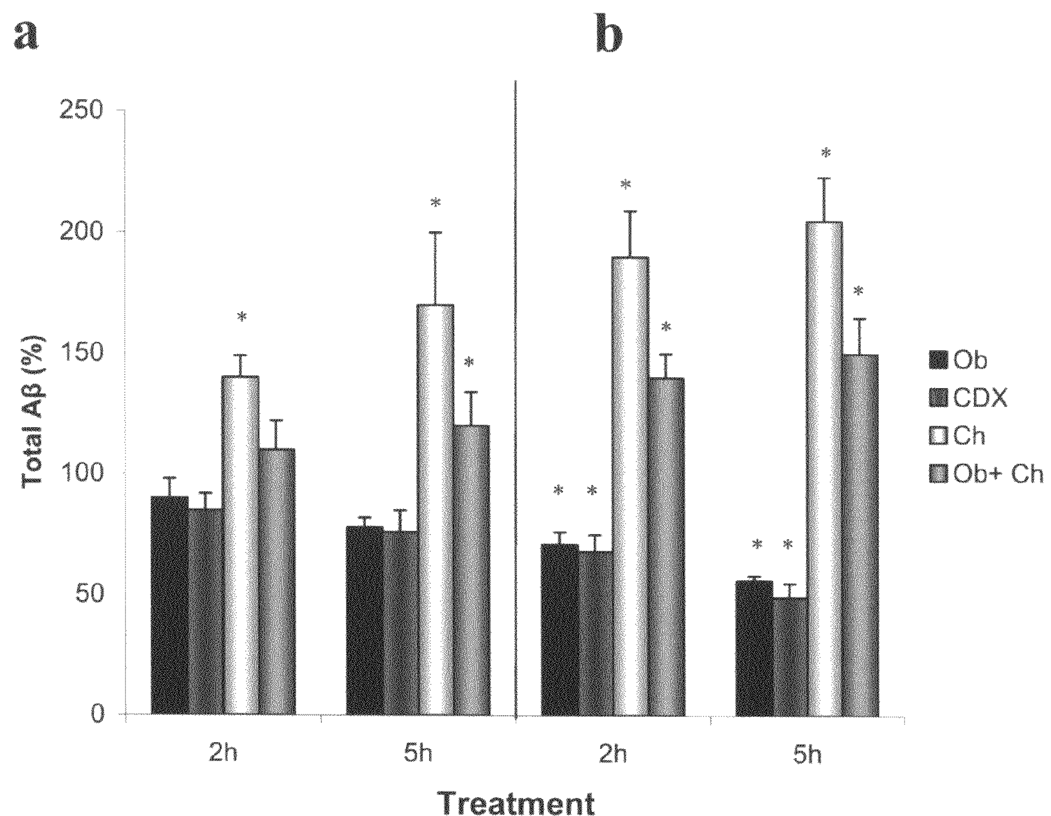
FIG. 4 shows that leptin affects Aβ production through BACE in rafts. Asterisks indicate that the value is significantly different from that of the corresponding control (set at $p<0.05$).
Figure 4:
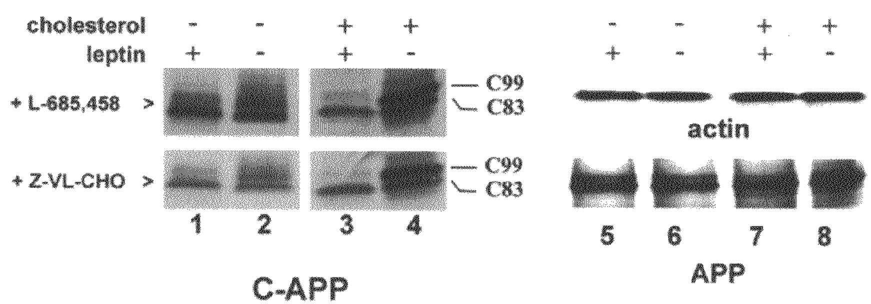
Figure 4:
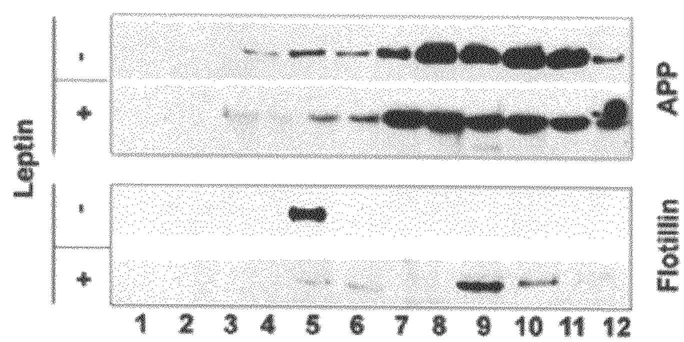
Figure 4:
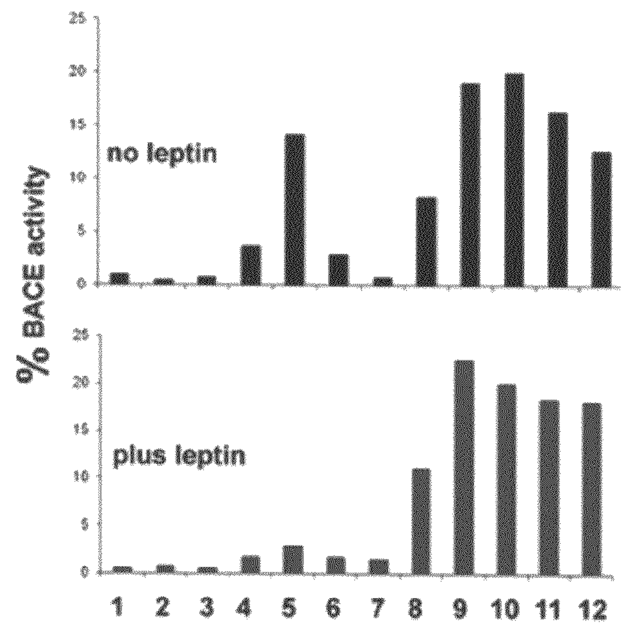

FIG. 4 shows that leptin affects Aβ production through BACE in rafts. In panel (a), Neuro2a cells stably transfected with hyg-sa134 were treated for about 2 h or about 5 h with about 100 ng/ml leptin, Ob (black); about 125 mg/ml cyclodextrin, CDX (striped gray); about 5 mg/ml cholesterol, Ch (pale gray); and leptin plus cholesterol, Ob+Ch (medium gray). Media were collected and assayed for total Aβ by ELISAs (Figueiredo-Pereira et al., *J Neurochem.* 72:1417-22 (1999)). Results are expressed as a percentage of the corresponding controls that did not receive drug treatment, measured at about 2 h and about 5 h respectively. Water soluble cholesterol (Sigma-Aldrich, Mo.) is a solution made of cholesterol balanced with CDX (40 mg cholesterol per gr CDX). In panel (b), Neuro2a cells stably transfected with hyg-sa134 were treated for about 2 h or 5 h with about 400 ng/ml leptin, Ob (black); about 250 mg/ml cyclodextrin, CDX (striped gray), about 10 mg/ml cholesterol, Ch (pale gray) and leptin plus cholesterol, Ob+Ch (medium gray) were used. In panel (c), SY5Y cells in culture were treated with about 400 ng/ml leptin or about 10 μg/ml cholesterol, or both, in the presence of the γ-secretase inhibitors L-685,458 (100 nM) or Z-VL-CHO (100 μM) for about 5 h. Extracts prepared from harvested cells were analysed by SDS-PAGE and Western blotting using an antibody directed against the C-terminal fraction of APP (C-APP, lanes 1-4) or actin (top lanes 5-8) or full-length APP (bottom lanes 5-8). Immunoreactive bands C99 and C83 correspond to β- and γ-secretase-generated fragments. In panel (d), extracts from SY5Y cells treated with and without leptin as above were solubilized in the presence of Triton X-100 and the insoluble fraction was applied to a discontinuous sucrose gradient as described (Cordy et al., 2003). Fractions collected from the bottom of the gradient were analysed by SDS-PAGE and Western blotting for the detection of APP and flotillin (marker for lipid rafts). A shift of the flotillin peak to more dense fractions of the gradient is observed following leptin treatment. In panel (e), fractions collected as above were assayed for β-secretase activity using a fluorescence-quenching assay (QTL Biosystems, NM). The results are expressed as the percent distribution of BACE activity within the gradient derived from cell cultures in the absence (black) or presence (gray) of leptin in the medium. Asterisks indicate that value is significantly different to that of the corresponding control (set at $p<0.05$).

Leptin caused a dose- and time-dependent decrease in the levels of Aβ detected in the media of transfected Neuro2a cells (56±5% following 5 h treatment with about 400 ng/ml leptin, FIG. 4*b*). Leptin was almost as efficient as methyl-β-cyclodextrin in lowering Aβ (FIG. 4*a*, 4*b*). In agreement with published data (Refolo et al., *Neurobiol Dis.* 7:321-31 (2000)), inclusion of water-soluble cholesterol in the culture media increased Aβ production (205±6% after 5 h with 10 μM, FIG. 4*b*). Leptin partially reduced the amyloidogenic potency of cholesterol when co-administered with cholesterol (150±4% after 5 h with the highest concentrations of leptin, FIG. 4*b*). When $^{125}$I-Aβ was included in the media during treatments in the presence or absence of 1 mM 1,10-phenanthroline, a general metalloprotease inhibitor which effectively inhibits degradation of secreted Aβ in vitro (Qiu et al., *J Biol Chem.* 272:6641-6646 (1997)), none of these treatments caused any significant differences in the degradation of Aβ in the medium, as assessed by measuring the percentage of $^{125}$I-Aβ converted to TCA soluble radioactivity. Treatment with 1,10-phenanthroline did not cause any significant difference in the tracer's uptake by the cells (see below).

Two approaches were used to investigate whether the observed changes in Aβ production were concomitant with fluctuations in β-secretase activity. First, cultures were treated in the presence of the γ-secretase inhibitors L-685,458 (Sigma, 100 nM) or Z-VL-CHO (Figueiredo-Pereira, M. E. (Figueiredo-Pereira et al., *J. Neurochem.* 72:1417-22 (1999)), (100 μM) to allow the accumulation of 10 kDa CAPPβ (C99) (SEQ ID NO: 8) and 8 kDa CAPPα (C83) (SEQ ID NO: 16), the C-terminal fragments of APP generated by β- and α-secretase respectively. Under those conditions, 5 h treatment with 10 μM cholesterol caused an increase in C99 (SEQ ID NO: 8) but not C83 (SEQ ID NO: 16) (FIG. 4*c*, lanes #2, 4), consistent with an increase in β-secretase activity. This increase was abolished in the presence of 400 ng/ml leptin (FIG. 4*c*, lane #3, 4). In addition, APP levels as detected by Western blotting were unchanged and $^{35}$S-Met metabolic labeling confirmed that neither APP synthesis (FIG. 4*c*, bottom lanes #5-8) nor proliferation, as detected by actin Western blots (FIG. 4*c*, top lanes #5-8), was affected. Leptin's effect on C99 (SEQ ID NO: 8) levels through possible inhibition of β-secretase also was observed in the absence of cholesterol (FIG. 4*c*, lanes #1, 2).

Second, activity of the beta-site amyloid precursor protein-cleaving enzyme (BACE) was measured in fractionated cell extracts using a fluorescence quenching assay (QTL Biosystems, NM) (FIG. 4*e*). LRs were prepared from a Triton X-100-insoluble membrane fraction further resolved by separation on a discontinuous sucrose gradient. All steps were carried out at 4° C. Confluent cells were scraped into 2 ml Mes-buffered saline (MBS, 25 mM Mes, 0.1 5M NaCl, pH 6.5) containing 1% (vol/vol) Triton X-100 and resuspended by passing them 5 times through a 25-gauge needle. An equal volume of 90% (wt/vol) sucrose in MBS then was added. Aliquots (1 ml) were placed in 5-ml ultracentrifuge tubes, and 4-ml discontinuous sucrose gradients consisting of 35% (wt/vol) sucrose in MBS (2 ml) and 5% (wt/vol) sucrose in MBS (2 ml) were layered on top. The sucrose gradients were centrifuged at 100,000×g for 18 h at 4° C. in a Beckman SW55 rotor, and fractions (0.5 ml) subsequently were harvested from the top to the bottom of the tube. (Cordy et al., *Proc Natl Acad Sci USA.* 100:11735-11740 (2003)). In agreement with others (Id.), BACE activity in extracts from control cells was detected in a low density fraction also containing flotillin (FIG. 4*d*), an integral membrane protein known to be a marker for neuronal LRs (Bickel et al., *J Biol Chem.* 272:13793-802 (1997)). Noticeably, the bulk of BACE activity was detected outside LRs, at higher density fractions. In addition, the distribution of APP immunoreactivity, as detected by Western blotting, was very similar to that of BACE activity in gradient fractions. Only a small fraction co-migrated with the flotillin peak (FIG. 4*d*). Leptin treatment resulted in a subtle change of the composition and/or density of LRs, as determined by the distribution of BACE activity, APP and flotillin on sucrose gradient fractions. Flotillin migrated at heavier subcellular fractions as compared to controls, and the activity of BACE in the low density fractions was almost absent. A similar shift in the elution position for both flotillin and BACE was observed when cells were treated with CDX (not shown). These data are consistent with the notion that a prerequisite for BACE to generate Aβ from APP is its association within LRs, and that the disruption of the lipid composition of those structures by leptin is sufficient to block the activity, presumably by hindering BACE's encounter with the substrate.

FIG. 6 shows that leptin can modulate free cholesterol-rich membrane domains and surplus cholesterol may trigger local leptin production. Neural cultures from ϵ15 rat cerebral cortex were processed for enrichment of neurons (a-d) or astrocytes (e-h) as described (Takeshima et al., J. Neurosci. Methods 67: 27-41 (1996)). After about 7 days to about 10 days in culture, cultures were treated for about 5 h with about 10 μg/ml cholesterol (b, f) or about 400 ng/ml leptin plus cholesterol (c, g) or leptin alone (d, h). Controls (a, e) were treated with culture media alone. Filipin staining was performed as described (Feng et al., Nat. Cell Biol. 5: 781-92 (2003)). Neurons (i-k) and astrocytes (l-n) prepared as above were treated with 0 μM (i, l), 5 μM (j, m) or 10 μM cholesterol (k, n) for 5 h. Immunostaining was performed for leptin (A.F.Parlow, Harbor-UCLA, CA).

In agreement with its ability to modulate the lipid composition of membranes, leptin treatment of primary neurons (FIG. 6*a-d*) and astrocytes (FIG. 6*e-h*) diminished filipin labelling (FIGS. 6*d* and 6*h*). Filipin is a fluorescent polyene antibiotic that binds to plasma membrane cholesterol (Feng et al., *Nat Cell Biol.* 5:781-92 (2003)). Further, the presence of leptin in cultures prohibited an increase in filipin labelling by cholesterol (FIGS. 6*b* and 6*f*) in both cell types (FIGS. 6*c* and 6*g*).

Leptin's ability to lower the production of Aβ was mimicked by (a) 5-(tetraecyloxyl-2-furoic acid (TOFA), a long chain fatty acid inhibitor of fatty acid synthesis that blocks the synthesis of malonyl-CoA by acetyl CoA carboxylase ("ACC") (Kempen et al. *J Lipid Res.* 36:1796-1806 (1995)) and (b) cerulenin, an ireversible fatty acid synthase ("FAS") inhibitor (Loftus et al., *Science.* 288:2379-81 (2000); Mobbs, *Science.* 288:2379-81 (2002)). In contrast, etomoxir (ethyl-2-[6-4-chlorophenoxy)hexyl)oxirane-2-carboxylate), an inhibitor of fatty acid oxidation at the level of carinitine palmitoyl transferase 1 (CPT1) (Minokoshi et al., 2002. *Nature.* 415:339-43 (2002)), increased Aβ production (Table 1). This is consistent with an association between leptin's prolipolytic/antilipogenic properties and APP metabolism. Similar results were obtained with SY5Y cells and adenovirus vector-infected primary neurons derived from embryonic rat brains (Table 1).

*robiol.* 13:357-407 (1999)). For the purpose of these experiments, however, lipid-poor apoE was utilized (Narita, J. Biochem. 132:743-749 (2002)).

FIG. 5 shows that leptin affects apoE-dependent Aβ-uptake and the possible involvement of SREBPs. In panel (a), Aβ uptake was measured in SY5Y cells following their treatment at 0 ng/ml, 100 ng/ml or 400 ng/ml leptin. Uptake also was measured in cells previously transfected with antisense DNA for PS1 as described (Tezapsidis et al., *FASEB J.* 17:1322-1324(2003)) (black). Uptake is expressed as the percentage of that observed with Aβ pre-incubated with apo∊3 (medium gray) in the absence of leptin (first set of columns). Inclusion of RAP (gray stripe) and omission of apoE (white) abolished uptake. Leptin induced a dose-dependent increase in Aβ uptake with a preference for apo∊3 (medium gray) over apo∊4 (light gray). In panel (b), SY5Y cells were pre-treated with 10 mg/ml cholesterol (+Chol) or normal medium (−Chol). Then Aβ uptake was measured following its preincubation with apo∊3 (∊3) or apo∊4 (∊4) in the absence (black) or the presence (gray) of about 400 ng/ml leptin. Cells were more resistant to taking-up Aβ when loaded with cholesterol. Asterisks indicate that the value is significantly different to that set as 100% (set at $p<0.05$). In panel (c), SY5Y cells were transiently transfected with SREBP-1 or SREBP-2 cDNA or an empty vector (Control). Then Aβ was measured in the medium by ELISAs (Figueiredo-Pereira et al., *J Neurochem.* 72:1417-22 (1999)) following treatment with (+) or without (−) leptin. Results are expressed as the percentage of the Aβ produced in cells transfected with empty vector that did not

TABLE 1

The effect of metabolic regulators on Aβ production by transfected Neuro2a cells, SY5Y cells or primary embryonic rat neurons infected with adenovirus.

| Inhibitor or Agent | Target or Action | Neuro2a/SEAP-APP Aβ(% control) | SY5Y Aβ (% control) | Neurons/SEAPP-APP Aβ (% control) |
|---|---|---|---|---|
| TOFA, 200 μM | ACC | 40 ± 15 | 58 ± 12 | 35 ± 4 |
| Cerulenin, 200 μM | FAS | 52 ± 12 | 65 ± 9, NS | 66 ± 5 |
| Etomoxir, 40 μM | CPT-1 | 154 ± 14 | 142 ± 14 | 158 ± 14 |
| Peptide YY (3-36), 25 μM | Anti-obesity | 92 ± 9, NS | 96 ± 7, NS | 98 ± 5, NS |
| Ciliary neurotrophic factor, 25 μM | Anti-obesity, neurotrophin | 95 ± 4, NS | 96 ± 8, NS | 89 ± 12, NS |
| Leptin, 400 ng/ml | Anti-obesity, Energy balance, immunomodulation | 56 ± 5 | 38 ± 7 | 35 ± 4 |

Results are expressed: as mean ± SEM from 4 experiments, each with 3 determinations. Values are expressed as a percentage of total Aβ found in the conditioned media of cells not receiving treatment. In 5 h SY5Y cells produced 252 ± 50 pM, Neuro2a-SEAP-APP produced 820 ± 210 pM and Neurons/SEAPP-APP produced 131 ± 83 pM. Student's t test was used and statistical significance was set at $p \leqq 0.05$. NS: statistically non-significant; TOFA: 5-(tetradecyloxy)-2-furancarboxylic acid; ACC: Acetyl CoA carboxylase; FAS: Fatty acid synthase; CPT-1: carnitine palmitoyl transferase-1

These findings confirm that metabolic pathways involving neuronal lipids and their distribution in membrane compartments influence Aβ production and establish that these can be controlled partially by exogenous leptin.

As Aβ homeostasis and lipid homeostasis are both the result of their production and clearance/uptake, respectively, the effect of leptin on the uptake of extracellular Aβ by SY5Y cells in culture also was investigated. It has been demonstrated that this process is facilitated by apolipoprotein E ("apoE"), which binds to Aβ and directs its capture via the Low-Density Lipoprotein Receptor Related Protein ("LRP") and the subsequent endocytosis/degradation of the protein-lipid complex by endosomes/lysosomes where only LRP is recycled. Without being limited by theory, this may be the primary mechanism by which neurons absorb lipids from circulating high-density lipoprotein-(HDL)-like lipoproteins from the brain interstitial space (Danik et al., *Crit Rev Neu-* receive leptin treatment, set at 100% (grey bar). In panel (d), Aβ uptake was measured in SY5Y cells prepared as in panel (c). Uptake was performed using Aβ/apo∊3 complexes. Results are expressed as the percentage of the Aβ taken-up by cells transfected with empty vector that did not receive leptin treatment, set at 100% (black bar).

Leptin increased the uptake of apoE-Aβ in a dose-dependent fashion (FIG. 5*a*, striped and white bars for apo∊3 and apo∊4, respectively). Interestingly, the ∊3 allele of apoE was more efficient in delivering Aβ to the cell than the ∊4 allele. This indicates that the apoE isoform associated with increased risk for AD may be more resistant to the beneficial action of leptin in promoting lipid delivery to neurons and degradation of Aβ. Next, SY5Y cells were preloaded with cholesterol by introducing a preincubation step with cholesterol/CDX, and compared to controls preincubated with medium. Only 22±6% of apo∊3-Aβ was taken up by cholesterol-loaded SY5Y cells compared to controls (FIG. 5*b*, black bars, first two pairs). Addition of about 400 ng/ml leptin during the cholesterol pre-incubation period and during the uptake almost completely reversed the phenotype of these cells to that of controls (FIG. 5*b*, striped bars with leptin, black bars without leptin). These results suggest that leptin increases the capacity of neurons to take-up apoE-Aβ (and presumably lipids) which may be of paramount importance under conditions of remodelling and/or repair. LRP-mediated apoE-lipoprotein internalization is arbitrated through clathrin-coated pits, suggesting that Aβ uptake may not involve membrane microdomains. However, there is increased awareness that LRs and clathrin-coated pits may not be exclusive concepts.

To gain insight into the specificity of leptin's ability to modulate Aβ production, cells were treated for 5 h with peptide YY (3-36), a gut-derived hormone affecting daily food intake that is believed to influence hypothalamic circuits (Batterham et al., *N Engl J Med.* 349:941-8 (2003)) and Ciliary Neurotrophic Factor (CNTF), a member of the gp130 family of cytokines that can regulate survival and differentiation of many types of developing and adult neurons (Sleeman et al., *Pharm Acta Helv.* 74:265-72 (2000)). At equimolar concentrations (25 μM) neither peptide changed Aβ production in a statistically significant way (Table 1), and this also was observed at higher (150 μM) concentrations (not shown).

To date, three SREBP isoforms, SREBP-1a (SEQ ID NO:17), SREBP-1c (SEQ ID NO:18) and SREBP-2 (SEQ ID NO:19) are known. Two isoforms, SREBP-1a and SREBP-1c, are transcribed from the SREBP-1 gene by alternative (or multiple) promoter usage for the same gene. The acidic transactivation domain that mediates interactions with chromatin modifying coactivators is shorter in SREBP-1c. As a result, SREBP-1c is a weaker transcriptional activator than SREBP-1a (Shimano et al. J. Cli. Inv. 99 (1997) 846-854). As used herein, the term SREBP-1 refers to the a isoform of SREBP-1. SREBP-2 (SEQ ID NO: 19) is more selective in activating the transcription of cholesterol biosynthetic genes, whereas SREBP-1 (SEQ ID NO: 17) and SREBP-1c (SEQ ID NO: 18) preferentially regulate fatty acid synthesis, however there is considerable overlap in their transcriptional activity.

The term "transactivation" as used herein refers to a technique used in molecular biology to control gene expression by stimulating transcription. It can be used to turn genes on and off. During transactivation, the transactivation gene and special promoters of DNA are inserted into the genome at areas of interest. The transactivator gene expresses a transcription factor that binds to specific promoter region(s) of DNA, causing that gene to be expressed. The expression of one transactivator gene can activate multiple genes, as long as they have the specific promoter region attached.

The term "coactivators" as used herein refers to a diverse array of gene regulatory proteins that do not themselves bind DNA but assemble on DNA-bound gene regulatory protein. They connect sequence-specific DNA binding activators to the general transcriptional machinery or help activators and the transcriptional apparatus navigate through the constraints of chromatin. Coactivator functions can be broadly divide into two classes: (a) adaptors that direct activator recruitment of the transcriptional apparatus, (b) chromatin-remodeling or -modifying enzymes.

It was of interest that SREBP-1c (SEQ ID NO: 18) MRNA and protein have been shown to be increased in the ob/ob mouse (Shimomura et al., *J Biol Chem.* 274:30028-32 (1999)), suggesting that leptin could regulate SREBP-1c (SEQ ID NO: 18) levels. To test this, SY5Y cells were transfected with modified pcDNA3.1 vectors to drive the expression of SREBP-1 (SEQ ID NO: 17) or SREBP-2 (SEQ ID NO: 19) under the CMV promoter, and some of the experiments of Aβ production or uptake in the presence or absence of leptin as already described were repeated.

As shown in FIG. 5, SREBP-2 (SEQ ID NO: 19) transfected cells were more resistant to the inhibition of Aβ production by leptin as compared to SREBP-1 (SEQ ID NO: 17) transfected cells (FIG. 5*c*). In addition, SREBP-2 (SEQ ID NO: 19) cells were resistant to the increase of apoE/Aβ uptake by leptin (FIG. 5*d*). Noticeably, transient expression of SREBP-1 (SEQ ID NO: 17) increased the production of Aβ to 138±22% as compared to controls (FIG. 5*c*) and reduced the uptake of apoE/Aβ to 41±5% as compared to controls (FIG. 5*d*). SREBP-2 (SEQ ID NO: 19) expression increased production of Aβ to 166±25% and inhibited uptake of apoE/Aβ to 25±8%. Without being limited by theory, at least two different scenarios could explain these results: a) leptin limits the availability of a common precursor for fatty acids and cholesterol (i.e. acetyl-CoA) or b) post-leptin receptor signaling events somehow turn-off SREBP-1 (SEQ ID NO: 17), causing a reduction in cholesterol, which is important for Aβ turnover. While the minor changes observed in SREBP-1 (SEQ ID NO: 17) transfected cells in the presence of leptin support the second possibility, both may be working in cohort.

In agreement with previous reports (Ur et al., *Neuroendocrinology.* 75:264-72 (2002)) leptin was detected immunocytochemically in dispersed neural cultures prepared from rat embryonic brain (FIG. 6*i*-6*n*) and by Western blotting of extracts of these cultures (data not shown). Similarly, the leptin receptor was detected in these cultures (not shown) (Couce et al., *Neuroendocrinology.* 66:145-50 (1997)). Interestingly, cholesterol treatment enhanced the levels of leptin-like immunoreactivity in both neurons (FIG. 6*i*-6*k*) and astrocytes (FIG. 6*l*-6*n*) in a dose dependent-fashion. Without being limited by theory, leptin appears to serve as a local feedback signal to inhibit further cholesterol synthesis and uptake, which in turn has an impact on Aβ production and uptake. Consequently, deficiencies in either leptin or transduction of its signal in neural cells could be contributory to AD-related pathways. Within the CNS, glia are the cell group prominently synthesizing apoE, cholesterol and phospholipid rich HDL-like lipoprotein particles (Fagan et al., *J Biol Chem.* 274:30001-7 (1999)). (As used herein, the terms "glia" or "glial cell" are used interchangeably to refer to the connective tissue cells of the CNS that serve as the supportive structure that holds together and protects neurons). Lipids are required by neurons during plasticity-related neuritic arborization/outgrowth or during neural progenitor cell proliferation. ("Neural plasticity" refers to the ability of neural circuits to undergo changes in function or organization due to previous activity). Nonetheless, excess cholesterol and Aβ can be harmful. Without being limited by theory, bi-directional communication between neurons and glia, based on local leptin (rather than leptin derived from the circulation) and leptin signaling pathways, may serve to balance local lipid requirement. It has been demonstrated previously that leptin can modulate hippocampal excitability via activation of large conductance calcium-activated potassium ion channels (Shanley et al., *Nat Neurosci.* 5:299-300 (2002)), supporting a link between endocrine factors and AD.

Example 2

In Vivo Leptin Activity

Plasma leptin levels were measured in transgenic mice engineered to express mutations linked to familial AD: APP with the Swedish mutation ($APP_{swe}$) (SEQ ID NO: 13), PS1 with the M146V substitution ($PS1_{M146V}$) (SEQ ID NO: 15), and both $APP_{Swe}$ (SEQ ID NO: 13) and $PS1_{M146V}$ (SEQ ID NO: 15). Among those, only the transgenic mice expressing $APP_{Swe}$ exhibit AD-like pathology. The $APP_{Swe}$-expressing mice in the $PS1_{M146V}$ background exhibit AD-like pathology at a younger age (6 months). The $PS1_{M146V}$ mice do not develop AD-like pathology.

FIG. 7 shows a deficiency of leptin in AD transgenic mice and the effect of leptin supplementation on amyloid load. In panel (a), plasma leptin was quantified in one year old mice with the following genotypes: i) double mutant $APP_{Swe}$/$PS1_{M146V}$ ii) single mutant $PS1_{M146V}$ and iii) wild-type (a cross between C57BL/6Ntac and B6SJLF2). Asterisk indicates that value is significantly different to that of non-transgenic controls (set at $p<0.05$). Plasma Aβ was also measured in these mice prior to treatment. Panel (b) shows Tg2576 mice under high fat (HFD) and low fat (LFD) diets one week prior to the implantation of the Alzet pump subcutaneously (s.c) for constant delivery of leptin (+) or vehicle PBS (−) at 8 months of age. The pump was replaced after 4 weeks. Formic acid extracts of brains obtained as described previously (Kawarabayashi et al., *J Neurosci.* 21:372-81 (2001)) were used to determine the Aβ40 (SEQ ID NO: 4) and Aβ42 (SEQ ID NO: 5) content by commercially available ELISA kits (KMI Diagnostics, MN), as decribed by the manufacturer. Only $APP_{Swe}$-expressing mice (Tg2576) contained detectable amounts of Aβ species. At 8 months of age the Tg2576 mouse has very low levels of Aβ. In panel (c), plasma leptin was determined by radioimmunoassay ("RIA") (LINCO Research, Inc.) in 8 month old Tg2576 and WT littermate mice and then again following treatments as described in FIG. 4*b*. Leptin also was measured in WT but not Tg2576 mice prior to treatment. In panel (d), plasma insulin was determined by RIA (LINCO Research, Inc.) in 8 month old WT and Tg2576 mice and then again following a 2 month LFD or HFD with (+) or without (−) leptin infusion. In panel (e), plasma total Aβ (Aβ40 (SEQ ID NO: 4) plus Aβ42/43 (SEQ ID NO: 5/SEQ ID NO: 6) was measured in 8 month Tg2576 mice and then again following a 2 month LFD or HFD with (+) or without (−) leptin infusion.

In both males and females, circulating leptin levels were approximately half of those in littermates not expressing the $APP_{Swe}$ (SEQ ID NO: 13), regardless of the expression of $PS1_{M146V}$ (SEQ ID NO: 15) (FIG. 7*a* and FIG. 7*c*).

Based on leptin's antiamyloidogenic activity in vitro as described above and the apparent leptin deficiency in the $APP_{Swe}$-expressing mice, the effect of chronic peripheral administration of leptin to animals under a high or low fat diet was investigated (FIG. 7*b*-7*f*). Constant subcutaneous (s.c.) infusion of murine leptin (0.25 μl/h of 3.33 mg/ml) (or PBS as placebo) was administered to Tg2576 or wild-type (WT) littermate mice for up to 8 weeks from about 8 months of age under the two different dietary regimens described above in Methods. Brain Aβ levels of the $APP_{Swe}$ hemizygous mouse rise between 6-9 months and lead to the appearance of the first thioflavin S positive amyloid plaques in the hippocampus and cerebral cortex, approximately 2 months later. (Thioflavin S is a histologic stain used to demonstrate amyloid containing neurofibrillary tangles and senile plaques in diseased brain tissue sections.) $APP_{Swe}$ expressing transgenic Tg2576 mice under the high fat diet had higher levels of both Aβ40 and Aβ42 in formic acid extracts of brain homogenates when compared to those under the low fat diet (FIG. 7*c*), in agreement with others (Refolo et al., *Neurobiol Dis.* 7:321-31 (2000)). Neuropathological examination was not performed because amyloid deposits in the form of cored or difuse plaques in the 10 month-old Tg2576 brains are too few (Kawarabayashi et al., *J Neurosci.* 21:372-81 (2001)) to allow statistically significant correlative studies. Further, plasma leptin and insulin levels were measured.

The level of leptin was confirmed to be lower in $APP_{Swe}$-expressing mice at 10 months, compared to controls, irrespective of diet and weight (FIG. 7*b*, 7*d*). In contrast, fasting insulin levels in mice of both genotypes fluctuated similarly and were elevated by high fat diet and lowered by low fat diet. Leptin treatment decreased fasting insulin levels in all groups, consistent with its ability to increase insulin sensitivity (FIG. 7*d*). Finally, quantification of total Aβ in the plasma (FIG. 7*e*) of the Tg2576 mouse revealed that leptin treatment was able to lower the levels of circulating Aβ under both diets. Without being limited by theory, it is not known whether this reflects the lowering of the CNS amyloid load shown in FIG. 7*c*, or is related to changes in peripheral Aβ production.

As the $APP_{Swe}$ transgene in the Tg2576 mouse is under the control of the Prion-protein promoter (Hsiao et al., *Science.* 274:99-102 (1996)), allowing its expression in the CNS and periphery (Ford et al., *Neuroscience.* 113:177-92. (2002); Lemaire-Vieille et al., *Proc Natl Acad Sci USA.* 97:5422-7 (2000)), and leptin is primarily produced in adipocytes, the adipose tissue extracted from these mice under high or low fat diets, plus or minus leptin treatment, was examined as described (Yu et al., *J Biol Chem.* 277:50876-84 (2002)). Higher levels of APP expression in adipocytes derived from the transgenic mice compared to expression in wild-type animals was detected. Leptin treatment had no apparent influence on this expression (data not shown). Interestingly, transgenic adipocytes were less responsive with regards to insulin-induced expression of leptin and glucose uptake than adipocytes from controls (data not shown). This was similar to the changes associated with senescence developed over time with normal aging in adipocytes (Yu and Zhu, *J Biol Chem.* 277:50876-84 (2003)).

Without being limited by theory, these studies support the conclusion that early leptin administration to Tg2576 mice has an impact on CNS amyloid deposition and should affect synaptic function and behavioral profile. These studies also demonstrate that a low fat diet in combination with leptin supplementation could be a potential palliative treatment for certain AD cases.

Without being limited by theory, the association between leptin/leptin signaling and AD-like pathobiology reported here in a mouse model is perhaps complementary, or works in parallel, to pathways involving insulin, as reviewed recently (Watson, *CNS Drugs.* 17:27-45 (2003)). Plasma leptin levels decrease with aging in a manner which is more profound in postmenopausal women (Isidori et al., *The Journal of Clinical Endocrinology & Metabolism.* 85:1954-1962 (2000)) and leptin receptors are present throughout the brain including the hippocampus and olfactory bulb, domains affected early during the course of the disease. Because dysregulation of pathways associated with leptin may play a critical role in the pathogenesis of AD, leptin treatment may be beneficial in some AD cases, specifically those experiencing weight loss and/or have low circulating leptin levels.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

The sequence listing in the form of a .txt file named "BioSeq.txt" containing SEQ ID NOs: 1-25, electronically filed on Dec. 4, 2006 as a substitute for the sequence listing originally filed with the application, is incorporated by reference herein.

What is claimed is:

1. A method for treating a progressive cognitive disease, cognitive disorder or cognitive condition resulting from accumulation of an amyloid peptide, the method comprising:

(a) administering to a subject in need thereof a first composition comprising:

(i) a therapeutically effective amount of a leptin, a pharmaceutically acceptable salt of the leptin, 5-tetradecyloxy-2-furoic acid (TOFA), cerulenin, or pharmaceutically acceptable salt of TOFA or cerulenin; and (ii) a pharmaceutically acceptable carrier, wherein the therapeutically effective amount is effective to modulate accumulation of the amyloid peptide in brain.

2. The method according to claim 1, the method further comprising the step of monitoring circulating levels of the amyloid peptide.

3. The method according to claim 2, wherein the circulating levels of amyloid peptide are detected in a sample of cerebrospinal fluid or blood.

4. The method according to claim 1, the method further comprising the step of placing the subject on a low fat diet.

5. The method according to claim 1, wherein the disease, disorder or condition is a dementia, an amyloidosis, Down's syndrome, or cerebral amyloid angiopathy.

6. The method according to claim 5, wherein the disease, condition or disorder is Alzheimer's disease.

7. The method according to claim 5, wherein the disease, condition or disorder is senile systemic amyloidosis.

8. The method according to claim 5, wherein the disease, condition or disorder is cerebrovascular amyloidosis.

9. The method according to claim 1, wherein the amyloid peptide is an amyloid β (Aβ) peptide.

10. The method according to claim 1, wherein the first composition in (a) further comprises (iii) a therapeutically effective amount of one or more lipolytic/antilipogenic compounds selected from the group consisting of 5-tetradecyloxy-2-furoic acid (TOPA), and cerulenin, wherein the one or more lipolytic/antilipogenic compound reduces Abeta (Aβ) production, increases apoE-Abeta (Aβ) uptake, or both.

11. The method according to claim 1, wherein the first composition modulates accumulation of the amyloid peptide in the cerebral nervous system.

12. The method according to claim 1, wherein the first composition is administered by at least one route selected from the group consisting of orally, buccally, parenterally, intranasally, rectally and topically.

13. The method according to claim 1, the method further comprising the step of serially administering a second composition comprising a therapeutically effective amount of one or more lipolytic/antilipogenic compounds selected from the group consisting of 5-tetradecyloxy-2-furoic acid (TOFA), and cerulenin, wherein the one or more lipolytic/antilipogenic compounds reduces Abeta production, increases apoE-Abeta uptake, or both.

14. The method according to claim 13, the method further comprising the step of placing the subject on a low fat diet.

15. The method according to claim 1, wherein the subject in need thereof has a systemic leptin deficiency.

16. The method according to claim 15, wherein the composition replenishes leptin.

17. The method according to claim 1, wherein the therapeutically effective amount amount is from about 0.01 mg per kg (of body weight) per day to about 0.5 mg per kg (of body weight) per day.

18. A method of improving resilience of cognitive function in a subject in need thereof, the method comprising the step of (a) administering to the subject a composition comprising:

i. a cognitive function-enhancing amount of a leptin, 5-tetradecyloxy-2-furoic acid (TOFA), cerulenin, a pharmaceutically acceptable salt of leptin, or a pharmaceutically acceptable salt of TOFA or cerulenin, and ii. a pharmaceutically acceptable carrier;

wherein the cognitive function-enhancing amount is effective to modulate-accumulation of an amyloid peptide in brain.

19. The method according to claim 18, wherein the composition is administered orally, buccally, parenterally, intranasally, rectally, or topically.

20. The method according to claim 18, further comprising the step (b) measuring the subject's ability to perform mental tasks.

21. The method according to claim 20, the subject's ability to perform mental tasks is measured by at least one test for memory, computation, or attention.

22. The method according to claim 18, wherein the cognitive function-enhancing amount of a leptin, 5-tetradecyloxy-2-furoic acid (TOFA), cerulenin, or a pharmaceutically acceptable salt of leptin, or a pharmaceutically acceptable salt of TOFA or cerulenin reduces Abeta (Aβ) production, increases apoE-Abeta (Aβ) uptake, or both.

23. The method according to claim 18, wherein the amyloid peptide is an amyloid β (Aβ) peptide.

24. The method according to claim 18, wherein the subject in need thereof has a systemic leptin deficiency.

25. The method according to claim 24, wherein the composition replenishes leptin.

26. The method according to claim 18, wherein the cognitive function-enhancing amount is from about 0.01 mg per kg (of body weight) per day to about 0.5 mg per kg (of body weight) per day.

* * * * *

SEQUENCE LISTING

<160> NUMBER OF SEQ ID NOS: 25

<210> SEQ ID NO 1
<211> LENGTH: 770
<212> TYPE: PRT
<213> ORGANISM: MAMMALIAN
<220> FEATURE:
<221> NAME/KEY: MISC_FEATURE
<223> OTHER INFORMATION: Human APP, isoform a

<400> SEQUENCE: 1

```
Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
    290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
            340                 345                 350
```

```
Thr Gln Glu Pro Leu Ala Arg Asp Pro Val Lys Leu Pro Thr Thr Ala
        355                 360                 365

Ala Ser Thr Pro Asp Ala Val Asp Lys Tyr Leu Glu Thr Pro Gly Asp
    370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
                405                 410                 415

Glu Arg Gln Ala Lys Asn Leu Pro Lys Ala Asp Lys Lys Ala Val Ile
            420                 425                 430

Gln His Phe Gln Glu Lys Val Glu Ser Leu Glu Gln Glu Ala Ala Asn
        435                 440                 445

Glu Arg Gln Gln Leu Val Glu Thr His Met Ala Arg Val Glu Ala Met
    450                 455                 460

Leu Asn Asp Arg Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
                485                 490                 495

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
        515                 520                 525

Gln Val Met Thr His Leu Arg Val Ile Tyr Glu Arg Met Asn Gln Ser
    530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
            580                 585                 590

Leu Met Pro Ser Leu Thr Glu Thr Lys Thr Thr Val Glu Leu Leu Pro
        595                 600                 605

Val Asn Gly Glu Phe Ser Leu Asp Asp Leu Gln Pro Trp His Ser Phe
    610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
            660                 665                 670

Ala Glu Phe Arg His Asp Ser Gly Tyr Glu Val His His Gln Lys Leu
        675                 680                 685

Val Phe Phe Ala Glu Asp Val Gly Ser Asn Lys Gly Ala Ile Ile Gly
    690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
        755                 760                 765

Gln Asn
```

770

<210> SEQ ID NO 2
<211> LENGTH: 751
<212> TYPE: PRT
<213> ORGANISM: MAMMALIAN
<220> FEATURE:
<221> NAME/KEY: MISC_FEATURE
<223> OTHER INFORMATION: Human APP, isoform b

<400> SEQUENCE: 2

```
Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
    290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Ile Pro Thr Thr Ala Ala Ser Thr
            340                 345                 350

Pro Asp Ala Val Asp Lys Tyr Leu Glu Thr Pro Gly Asp Glu Asn Glu
```

-continued

```
        355                 360                 365

His Ala His Phe Gln Lys Ala Lys Glu Arg Leu Glu Ala Lys His Arg
    370                 375                 380

Glu Arg Met Ser Gln Val Met Arg Glu Trp Glu Glu Ala Glu Arg Gln
385                 390                 395                 400

Ala Lys Asn Leu Pro Lys Ala Asp Lys Lys Ala Val Ile Gln His Phe
                405                 410                 415

Gln Glu Lys Val Glu Ser Leu Glu Gln Glu Ala Ala Asn Glu Arg Gln
            420                 425                 430

Gln Leu Val Glu Thr His Met Ala Arg Val Glu Ala Met Leu Asn Asp
        435                 440                 445

Arg Arg Arg Leu Ala Leu Glu Asn Tyr Ile Thr Ala Leu Gln Ala Val
    450                 455                 460

Pro Pro Arg Pro Arg His Val Phe Asn Met Leu Lys Lys Tyr Val Arg
465                 470                 475                 480

Ala Glu Gln Lys Asp Arg Gln His Thr Leu Lys His Phe Glu His Val
                485                 490                 495

Arg Met Val Asp Pro Lys Lys Ala Ala Gln Ile Arg Ser Gln Val Met
            500                 505                 510

Thr His Leu Arg Val Ile Tyr Glu Arg Met Asn Gln Ser Leu Ser Leu
        515                 520                 525

Leu Tyr Asn Val Pro Ala Val Ala Glu Glu Ile Gln Asp Glu Val Asp
    530                 535                 540

Glu Leu Leu Gln Lys Glu Gln Asn Tyr Ser Asp Asp Val Leu Ala Asn
545                 550                 555                 560

Met Ile Ser Glu Pro Arg Ile Ser Tyr Gly Asn Asp Ala Leu Met Pro
                565                 570                 575

Ser Leu Thr Glu Thr Lys Thr Thr Val Glu Leu Leu Pro Val Asn Gly
            580                 585                 590

Glu Phe Ser Leu Asp Asp Leu Gln Pro Trp His Ser Phe Gly Ala Asp
        595                 600                 605

Ser Val Pro Ala Asn Thr Glu Asn Glu Val Glu Pro Val Asp Ala Arg
    610                 615                 620

Pro Ala Ala Asp Arg Gly Leu Thr Thr Arg Pro Gly Ser Gly Leu Thr
625                 630                 635                 640

Asn Ile Lys Thr Glu Glu Ile Ser Glu Val Lys Met Asp Ala Glu Phe
                645                 650                 655

Arg His Asp Ser Gly Tyr Glu Val His His Gln Lys Leu Val Phe Phe
            660                 665                 670

Ala Glu Asp Val Gly Ser Asn Lys Gly Ala Ile Ile Gly Leu Met Val
        675                 680                 685

Gly Gly Val Val Ile Ala Thr Val Ile Val Ile Thr Leu Val Met Leu
    690                 695                 700

Lys Lys Lys Gln Tyr Thr Ser Ile His His Gly Val Val Glu Val Asp
705                 710                 715                 720

Ala Ala Val Thr Pro Glu Glu Arg His Leu Ser Lys Met Gln Gln Asn
                725                 730                 735

Gly Tyr Glu Asn Pro Thr Tyr Lys Phe Phe Glu Gln Met Gln Asn
            740                 745                 750
```

<210> SEQ ID NO 3
<211> LENGTH: 695
<212> TYPE: PRT
<213> ORGANISM: MAMMALIAN
<220> FEATURE:

```
<221> NAME/KEY: MISC_FEATURE
<223> OTHER INFORMATION: Human APP, Isoform c

<400> SEQUENCE: 3

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Val Pro Thr Thr Ala Ala Ser Thr Pro Asp Ala Val Asp Lys Tyr Leu
    290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
        355                 360                 365

Gln Glu Ala Ala Asn Glu Arg Gln Gln Leu Val Glu Thr His Met Ala
    370                 375                 380

Arg Val Glu Ala Met Leu Asn Asp Arg Arg Arg Leu Ala Leu Glu Asn
385                 390                 395                 400
```

```
Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
            420                 425                 430

Thr Leu Lys His Phe Glu His Val Arg Met Val Asp Pro Lys Lys Ala
        435                 440                 445

Ala Gln Ile Arg Ser Gln Val Met Thr His Leu Arg Val Ile Tyr Glu
    450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
            500                 505                 510

Tyr Gly Asn Asp Ala Leu Met Pro Ser Leu Thr Glu Thr Lys Thr Thr
        515                 520                 525

Val Glu Leu Leu Pro Val Asn Gly Glu Phe Ser Leu Asp Asp Leu Gln
    530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Lys Met Asp Ala Glu Phe Arg His Asp Ser Gly Tyr Glu Val
        595                 600                 605

His His Gln Lys Leu Val Phe Phe Ala Glu Asp Val Gly Ser Asn Lys
    610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
        675                 680                 685

Phe Phe Glu Gln Met Gln Asn
    690                 695


<210> SEQ ID NO 4
<211> LENGTH: 40
<212> TYPE: PRT
<213> ORGANISM: MAMMALIAN
<220> FEATURE:
<221> NAME/KEY: MISC_FEATURE
<223> OTHER INFORMATION: Abeta40

<400> SEQUENCE: 4

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40


<210> SEQ ID NO 5
<211> LENGTH: 42
```

```
<212> TYPE: PRT
<213> ORGANISM: MAMMALIAN
<220> FEATURE:
<221> NAME/KEY: MISC_FEATURE
<223> OTHER INFORMATION: Abeta42

<400> SEQUENCE: 5

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40


<210> SEQ ID NO 6
<211> LENGTH: 43
<212> TYPE: PRT
<213> ORGANISM: MAMMALIAN
<220> FEATURE:
<221> NAME/KEY: MISC_FEATURE
<223> OTHER INFORMATION: Abeta43

<400> SEQUENCE: 6

Asp Ala Glu Phe Arg His Asp Ser Gly Tyr Glu Val His His Gln Lys
1               5                   10                  15

Leu Val Phe Phe Ala Glu Asp Val Gly Ser Ile Ile Lys Gly Ala Ile
            20                  25                  30

Ile Gly Leu Met Val Gly Gly Val Val Ile Ala
        35                  40


<210> SEQ ID NO 7
<211> LENGTH: 671
<212> TYPE: PRT
<213> ORGANISM: MAMMALIAN
<220> FEATURE:
<221> NAME/KEY: MISC_FEATURE
<223> OTHER INFORMATION: sAPPbeta (based on SEQ ID NO:1)

<400> SEQUENCE: 7

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175
```

```
Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
    290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
            340                 345                 350

Thr Gln Glu Pro Leu Ala Arg Asp Pro Val Lys Leu Pro Thr Thr Ala
        355                 360                 365

Ala Ser Thr Pro Asp Ala Val Asp Lys Tyr Leu Glu Thr Pro Gly Asp
    370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
                405                 410                 415

Glu Arg Gln Ala Lys Asn Leu Pro Lys Ala Asp Lys Lys Ala Val Ile
            420                 425                 430

Gln His Phe Gln Glu Lys Val Glu Ser Leu Glu Gln Glu Ala Ala Asn
        435                 440                 445

Glu Arg Gln Gln Leu Val Glu Thr His Met Ala Arg Val Glu Ala Met
    450                 455                 460

Leu Asn Asp Arg Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
                485                 490                 495

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
        515                 520                 525

Gln Val Met Thr His Leu Arg Val Ile Tyr Glu Arg Met Asn Gln Ser
    530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
            580                 585                 590

Leu Met Pro Ser Leu Thr Glu Thr Lys Thr Thr Val Glu Leu Leu Pro
```

```
        595                 600                 605

Val Asn Gly Glu Phe Ser Leu Asp Asp Leu Gln Pro Trp His Ser Phe
    610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met
            660                 665                 670


<210> SEQ ID NO 8
<211> LENGTH: 99
<212> TYPE: PRT
<213> ORGANISM: MAMMALIAN
<220> FEATURE:
<221> NAME/KEY: MISC_FEATURE
<223> OTHER INFORMATION: 10 kDa CAPPbeta (C99)

<400> SEQUENCE: 8

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr Val Ile Val Ile Thr
        35                  40                  45

Leu Val Met Leu Lys Lys Lys Gln Tyr Thr Ser Ile His His Gly Val
    50                  55                  60

Val Glu Val Asp Ala Ala Val Thr Pro Glu Glu Arg His Leu Ser Lys
65                  70                  75                  80

Met Gln Gln Asn Gly Tyr Glu Asn Pro Thr Tyr Lys Phe Phe Glu Gln
                85                  90                  95

Met Gln Asn


<210> SEQ ID NO 9
<211> LENGTH: 1461
<212> TYPE: DNA
<213> ORGANISM: MAMMALIAN
<220> FEATURE:
<221> NAME/KEY: misc_feature
<223> OTHER INFORMATION: SEAP DNA sequence (corresponds to nucleotides
      981-2441) of hyg-sa134 vector (SEQ ID NO: 11)

<400> SEQUENCE: 9

gttgaggagg agaacccgga cttctggaac cgcgaggcag ccgaggccct gggtgccgcc      60

aagaagctgc agcctgcaca gacagccgcc aagaacctca tcatcttcct gggcgatggg     120

atgggggtgt ctacggtgac agctgccagg atcctaaaag ggcagaagaa ggacaaactg     180

gggcctgaga taccccctggc catggaccgc ttcccatatg tggctctgtc caagacatac     240

aatgtagaca aacatgtgcc agacagtgga gccacagcca cggcctacct gtgcggggtc     300

aagggcaact tccagaccat tggcttgagt gcagccgccc gctttaacca gtgcaacacg     360

acacgcggca acgaggtcat ctccgtgatg aatcgggcca agaaagcagg gaagtcagtg     420

ggagtggtaa ccaccacacg agtgcagcac gcctcgccag ccggcaccta cgcccacacg     480

gtgaaccgca actggtactc ggacgccgac gtgcctgcct cggcccgcca ggaggggtgc     540

caggacatcg ctacgcagct catctccaac atggacattg atgtgatcct aggtggaggc     600

cgaaagtaca tgtttcgcat gggaacccca gaccctgagt acccagatga ctacagccaa     660

ggtgggacca ggctggacgg gaagaatctg gtgcaggaat ggctcggcga acgccagggt     720
```

```
gcccggtacg tgtggaaccg cactgagctc atgcaggctt ccctggaccc gtctgtgacc    780

catctcatgg gtctctttga gcctggagac atgaaatacg agatccaccg agactccaca    840

ctggacccct ccctgatgga gatgacagag gctgccctgc gcctgctgag cagacacccc    900

cgcggcttct tcctcttcgt ggagggtggt cgcatcgacc atggtcatca tgaaagcagg    960

gcttaccggg cactgactga gacgatcatg ttcgacgacg ccattgagag ggcgggccag   1020

ctcaccagcg aggaggacac gctgagcctc gtcactgccg accactccca cgtcttctcc   1080

ttcggaggct accccctgcg agggagctcc ttcatcgggc tggccgctgg caaggcccgg   1140

gacaggaagg cctacacggt cctcctatac ggaaacggtc caggctatgt gctcaaggac   1200

ggcgcccggc cggatgttac cgagagcgag agcgggagcc ccgagtatcg gcagcagtca   1260

gcagtgcccc tggacgaaga gacccacgca ggcgaggacg tggcggtgtt cgcgcgcggc   1320

ccgcaggcgc acctggttca cggcgtgcag gagcagacct tcatagcgca cgtcatggcc   1380

ttcgccgcct gcctggagcc ctacaccgcc tgcgacctgg cgcccccgc cggcaccacc    1440

gacgccgcgc acccgggttg g                                             1461
```

```
<210> SEQ ID NO 10
<211> LENGTH: 134
<212> TYPE: PRT
<213> ORGANISM: MAMMALIAN
<220> FEATURE:
<221> NAME/KEY: MISC_FEATURE
<223> OTHER INFORMATION: Amino acid sequence of CAPP134 (amino acid
      residues 630-770 of human APP, isoform a, SEQ ID NO: 1)

<400> SEQUENCE: 10

Val Glu Pro Val Asp Ala Arg Pro Ala Ala Asp Arg Gly Leu Thr Thr
1               5                   10                  15

Arg Pro Gly Ser Gly Leu Thr Asn Ile Lys Thr Glu Glu Ile Ser Glu
            20                  25                  30

Val Lys Met Asp Ala Glu Phe Arg His Asp Ser Gly Tyr Glu Val His
        35                  40                  45

His Gln Lys Leu Val Phe Phe Ala Glu Asp Val Gly Ser Asn Lys Gly
    50                  55                  60

Ala Ile Ile Gly Leu Met Val Gly Gly Val Val Ile Ala Thr Val Ile
65                  70                  75                  80

Val Ile Thr Leu Val Met Leu Lys Lys Lys Gln Tyr Thr Ser Ile His
                85                  90                  95

His Gly Val Val Glu Val Asp Ala Ala Val Thr Pro Glu Glu Arg His
            100                 105                 110

Leu Ser Lys Met Gln Gln Asn Gly Tyr Glu Asn Pro Thr Tyr Lys Phe
        115                 120                 125

Phe Glu Gln Met Gln Asn
    130
```

```
<210> SEQ ID NO 11
<211> LENGTH: 7506
<212> TYPE: DNA
<213> ORGANISM: MAMMALIAN
<220> FEATURE:
<221> NAME/KEY: misc_feature
<223> OTHER INFORMATION: The DNA sequence of the entire hygsa134 vector
      (with inserts)

<400> SEQUENCE: 11

gacggatcgg gagatctccc gatcccctat ggtcgactct cagtacaatc tgctctgatg     60
```

```
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttctgc atgctgctgc tgctgctgct gctgggcctg aggctacagc    960
tctccctggg catcatccta gttgaggagg agaacccgga cttctggaac cgcgaggcag   1020
ccgaggccct gggtgccgcc aagaagctgc agcctgcaca gacagccgcc aagaacctca   1080
tcatcttcct gggcgatggg atgggggtgt ctacggtgac agctgccagg atcctaaaag   1140
ggcagaagaa ggacaaactg gggcctgaga taccccctggc catggaccgc ttcccatatg   1200
tggctctgtc caagacatac aatgtagaca aacatgtgcc agacagtgga gccacagcca   1260
cggcctacct gtgcggggtc aagggcaact tccagaccat tggcttgagt gcagccgccc   1320
gctttaacca gtgcaacacg acacgcggca acgaggtcat ctccgtgatg aatcgggcca   1380
agaaagcagg gaagtcagtg ggagtggtaa ccaccacacg agtgcagcac gcctcgccag   1440
ccggcaccta cgcccacacg gtgaaccgca actggtactc ggacgccgac gtgcctgcct   1500
cggcccgcca ggaggggtgc caggacatcg ctacgcagct catctccaac atggacattg   1560
atgtgatcct aggtggaggc cgaaagtaca tgtttcgcat gggaacccca gaccctgagt   1620
acccagatga ctacagccaa ggtgggacca ggctggacgg gaagaatctg gtgcaggaat   1680
ggctcggcga acgccagggt gcccggtacg tgtggaaccg cactgagctc atgcaggctt   1740
ccctggaccc gtctgtgacc catctcatgg gtctctttga gcctggagac atgaaatacg   1800
agatccaccg agactccaca ctggacccct ccctgatgga gatgacagag gctgccctgc   1860
gcctgctgag cagacacccc cgcggcttct tcctcttcgt ggagggtggt cgcatcgacc   1920
atggtcatca tgaaagcagg gcttaccggg cactgactga gacgatcatg ttcgacgacg   1980
ccattgagag ggcgggccag ctcaccagcg aggaggacac gctgagcctc gtcactgccg   2040
accactccca cgtcttctcc ttcggaggct accccctgcg agggagctcc ttcatcgggc   2100
tggccgctgg caaggcccgg gacaggaagg cctacacggt cctcctatac ggaaacggtc   2160
caggctatgt gctcaaggac ggcgcccggc cggatgttac cgagagcgag agcgggagcc   2220
ccgagtatcg gcagcagtca gcagtgcccc tggacgaaga gacccacgca ggcgaggacg   2280
tggcggtgtt cgcgcgcggc ccgcaggcgc acctggttca cggcgtgcag gagcagacct   2340
tcatagcgca cgtcatggcc ttcgccgcct gcctggagcc ctacaccgcc tgcgacctgg   2400
cgccccccgc cggcaccacc gacgccgcgc acccgggttg gaagatccta gttgagcctg   2460
```

```
ttgatgcccg ccctgctgcc gaccgaggac tgaccactcg accaggttct gggttgacaa   2520

atatcaagac ggaggagatc tctgaagtga agatggatgc agaattccga catgactcag   2580

gatatgaagt tcatcatcaa aaattggtgt tctttgcaga agatgtgggt tcaaacaaag   2640

gtgcaatcat tggactcatg gtgggcggtg ttgtcatagc gacagtgatc gtcatcacct   2700

tggtgatgct gaagaagaaa cagtacacat ccattcatca tggtgtggtg gaggttgacg   2760

ccgctgtcac cccagaggag cgccacctgt ccaagatgca gcagaacggc tacgaaaatc   2820

caacctacaa gttctttgag cagatgcaga actagacccc cgccacagca gcctctgaag   2880

ttggacagcc tcgagtctag agggcccgtt taaacccgct gatcagcctc gactgtgcct   2940

tctagttgcc agccatctgt tgtttgcccc tcccccgtgc cttccttgac cctggaaggt   3000

gccactccca ctgtcctttc ctaataaaat gaggaaattg catcgcattg tctgagtagg   3060

tgtcattcta ttctgggggg tggggtgggg caggacagca agggggagga ttgggaagac   3120

aatagcaggc atgctgggga tgcggtgggc tctatggctt ctgaggcgga aagaaccagc   3180

tggggctcta gggggtatcc ccacgcgccc tgtagcggcg cattaagcgc ggcgggtgtg   3240

gtggttacgc gcagcgtgac cgctacactt gccagcgccc tagcgcccgc tcctttcgct   3300

ttcttccctt cctttctcgc cacgttcgcc ggctttcccc gtcaagctct aaatcggggc   3360

atccctttag ggttccgatt tagtgcttta cggcacctcg accccaaaaa acttgattag   3420

ggtgatggtt cacgtagtgg gccatcgccc tgatagacgg tttttcgccc tttgacgttg   3480

gagtccacgt tctttaatag tggactcttg ttccaaactg gaacaacact caaccctatc   3540

tcggtctatt cttttgattt ataagggatt ttggggattt cggcctattg gttaaaaaat   3600

gagctgattt aacaaaaatt taacgcgaat taattctgtg gaatgtgtgt cagttagggt   3660

gtggaaagtc cccaggctcc ccaggcaggc agaagtatgc aaagcatgca tctcaattag   3720

tcagcaacca ggtgtggaaa gtccccaggc tccccagcag gcagaagtat gcaaagcatg   3780

catctcaatt agtcagcaac catagtcccg cccctaactc cgcccatccc gcccctaact   3840

ccgcccagtt ccgcccattc tccgccccat ggctgactaa ttttttttat ttatgcagag   3900

gccgaggccg cctctgcctc tgagctattc cagaagtagt gaggaggctt ttttggaggc   3960

ctaggctttt gcaaaaagct cccgggagct tgtatatcca ttttcggatc tgatcagcac   4020

gtgatgaaaa agcctgaact caccgcgacg tctgtcgaga agtttctgat cgaaaagttc   4080

gacagcgtct ccgacctgat gcagctctcg gagggcgaag aatctcgtgc tttcagcttc   4140

gatgtaggag ggcgtggata tgtcctgcgg gtaaatagct gcgccgatgg tttctacaaa   4200

gatcgttatg tttatcggca ctttgcatcg gccgcgctcc cgattccgga agtgcttgac   4260

attggggaat tcagcgagag cctgacctat tgcatctccc gccgtgcaca gggtgtcacg   4320

ttgcaagacc tgcctgaaac cgaactgccc gctgttctgc agccggtcgc ggaggccatg   4380

gatgcgatcg ctgcggccga tcttagccag acgagcgggt tcggcccatt cggaccgcaa   4440

ggaatcggtc aatacactac atggcgtgat ttcatatgcg cgattgctga tccccatgtg   4500

tatcactggc aaactgtgat ggacgacacc gtcagtgcgt ccgtcgcgca ggctctcgat   4560

gagctgatgc tttgggccga ggactgcccc gaagtccggc acctcgtgca cgcggatttc   4620

ggctccaaca atgtcctgac ggacaatggc cgcataacag cggtcattga ctggagcgag   4680

gcgatgttcg gggattccca atacgaggtc gccaacatct tcttctggag gccgtggttg   4740

gcttgtatgg agcagcagac gcgctacttc gagcggaggc atccggagct tgcaggatcg   4800

ccgcggctcc gggcgtatat gctccgcatt ggtcttgacc aactctatca gagcttggtt   4860
```

```
gacggcaatt tcgatgatgc agcttgggcg cagggtcgat gcgacgcaat cgtccgatcc   4920
ggagccggga ctgtcgggcg tacacaaatc gcccgcagaa gcgcggccgt ctggaccgat   4980
ggctgtgtag aagtactcgc cgatagtgga aaccgacgcc ccagcactcg tccgagggca   5040
aaggaatagc acgtgctacg agatttcgat tccaccgccg ccttctatga aaggttgggc   5100
ttcggaatcg ttttccggga cgccggctgg atgatcctcc agcgcgggga tctcatgctg   5160
gagttcttcg cccaccccaa cttgtttatt gcagcttata atggttacaa ataaagcaat   5220
agcatcacaa atttcacaaa taaagcattt ttttcactgc attctagttg tggtttgtcc   5280
aaactcatca atgtatctta tcatgtctgt ataccgtcga cctctagcta gagcttggcg   5340
taatcatggt catagctgtt tcctgtgtga aattgttatc cgctcacaat tccacacaac   5400
atacgagccg gaagcataaa gtgtaaagcc tggggtgcct aatgagtgag ctaactcaca   5460
ttaattgcgt tgcgctcact gcccgctttc cagtcgggaa acctgtcgtg ccagctgcat   5520
taatgaatcg gccaacgcgc ggggagaggc ggtttgcgta ttgggcgctc ttccgcttcc   5580
tcgctcactg actcgctgcg ctcggtcgtt cggctgcggc gagcggtatc agctcactca   5640
aaggcggtaa tacggttatc cacagaatca ggggataacg caggaaagaa catgtgagca   5700
aaaggccagc aaaaggccag gaaccgtaaa aaggccgcgt tgctggcgtt tttccatagg   5760
ctccgccccc ctgacgagca tcacaaaaat cgacgctcaa gtcagaggtg gcgaaacccg   5820
acaggactat aaagatacca ggcgtttccc cctggaagct ccctcgtgcg ctctcctgtt   5880
ccgaccctgc cgcttaccgg atacctgtcc gcctttctcc cttcgggaag cgtggcgctt   5940
tctcaatgct cacgctgtag gtatctcagt tcggtgtagg tcgttcgctc caagctgggc   6000
tgtgtgcacg aaccccccgt tcagcccgac cgctgcgcct tatccggtaa ctatcgtctt   6060
gagtccaacc cggtaagaca cgacttatcg ccactggcag cagccactgg taacaggatt   6120
agcagagcga ggtatgtagg cggtgctaca gagttcttga agtggtggcc taactacggc   6180
tacactagaa ggacagtatt tggtatctgc gctctgctga agccagttac cttcggaaaa   6240
agagttggta gctcttgatc cggcaaacaa accaccgctg gtagcggtgg tttttttgtt   6300
tgcaagcagc agattacgcg cagaaaaaaa ggatctcaag aagatccttt gatcttttct   6360
acggggtctg acgctcagtg gaacgaaaac tcacgttaag ggattttggt catgagatta   6420
tcaaaaagga tcttcaccta gatcctttta aattaaaaat gaagttttaa atcaatctaa   6480
agtatatatg agtaaacttg gtctgacagt taccaatgct taatcagtga ggcacctatc   6540
tcagcgatct gtctatttcg ttcatccata gttgcctgac tccccgtcgt gtagataact   6600
acgatacggg agggcttacc atctggcccc agtgctgcaa tgataccgcg agacccacgc   6660
tcaccggctc cagatttatc agcaataaac cagccagccg gaagggccga gcgcagaagt   6720
ggtcctgcaa ctttatccgc ctccatccag tctattaatt gttgccggga agctagagta   6780
agtagttcgc cagttaatag tttgcgcaac gttgttgcca ttgctacagg catcgtggtg   6840
tcacgctcgt cgtttggtat ggcttcattc agctccggtt cccaacgatc aaggcgagtt   6900
acatgatccc ccatgttgtg caaaaaagcg gttagctcct tcggtcctcc gatcgttgtc   6960
agaagtaagt tggccgcagt gttatcactc atggttatgg cagcactgca taattctctt   7020
actgtcatgc catccgtaag atgcttttct gtgactggtg agtactcaac caagtcattc   7080
tgagaatagt gtatgcggcg accgagttgc tcttgcccgg cgtcaatacg ggataatacc   7140
gcgccacata gcagaacttt aaaagtgctc atcattggaa aacgttcttc ggggcgaaaa   7200
ctctcaagga tcttaccgct gttgagatcc agttcgatgt aacccactcg tgcacccaac   7260
```

```
tgatcttcag catcttttac tttcaccagc gtttctgggt gagcaaaaac aggaaggcaa   7320

aatgccgcaa aaaagggaat aagggcgaca cggaaatgtt gaatactcat actcttcctt   7380

tttcaatatt attgaagcat ttatcagggt tattgtctca tgagcggata catatttgaa   7440

tgtatttaga aaaataaaca aataggggtt ccgcgcacat ttccccgaaa agtgccacct   7500

gacgtc                                                              7506


<210> SEQ ID NO 12
<211> LENGTH: 440
<212> TYPE: DNA
<213> ORGANISM: MAMMALIAN
<220> FEATURE:
<221> NAME/KEY: misc_feature
<223> OTHER INFORMATION: CAPP134 cDNA insert in hygsa134 vector

<400> SEQUENCE: 12

agttgagcct gttgatgccc gccctgctgc cgaccgagga ctgaccactc gaccaggttc     60

tgggttgaca aatatcaaga cggaggagat ctctgaagtg aagatggatg cagaattccg    120

acatgactca ggatatgaag ttcatcatca aaaattggtg ttctttgcag aagatgtggg    180

ttcaaacaaa ggtgcaatca ttggactcat ggtgggcggt gttgtcatag cgacagtgat    240

cgtcatcacc ttggtgatgc tgaagaagaa acagtacaca tccattcatc atggtgtggt    300

ggaggttgac gccgctgtca ccccagagga gcgccacctg tccaagatgc agcagaacgg    360

ctacgaaaat ccaacctaca agttctttga gcagatgcag aactagaccc ccgccacagc    420

agcctctgaa gttggacagc                                                440


<210> SEQ ID NO 13
<211> LENGTH: 770
<212> TYPE: PRT
<213> ORGANISM: MAMMALIAN
<220> FEATURE:
<221> NAME/KEY: MISC_FEATURE
<223> OTHER INFORMATION: APPswe

<400> SEQUENCE: 13

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175
```

```
Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
    290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
            340                 345                 350

Thr Gln Glu Pro Leu Ala Arg Asp Pro Val Lys Leu Pro Thr Thr Ala
        355                 360                 365

Ala Ser Thr Pro Asp Ala Val Asp Lys Tyr Leu Glu Thr Pro Gly Asp
    370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
                405                 410                 415

Glu Arg Gln Ala Lys Asn Leu Pro Lys Ala Asp Lys Lys Ala Val Ile
            420                 425                 430

Gln His Phe Gln Glu Lys Val Glu Ser Leu Glu Gln Glu Ala Ala Asn
        435                 440                 445

Glu Arg Gln Gln Leu Val Glu Thr His Met Ala Arg Val Glu Ala Met
    450                 455                 460

Leu Asn Asp Arg Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
                485                 490                 495

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
        515                 520                 525

Gln Val Met Thr His Leu Arg Val Ile Tyr Glu Arg Met Asn Gln Ser
    530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
            580                 585                 590

Leu Met Pro Ser Leu Thr Glu Thr Lys Thr Thr Val Glu Leu Leu Pro
```

```
        595                 600                 605

Val Asn Gly Glu Phe Ser Leu Asp Asp Leu Gln Pro Trp His Ser Phe
    610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Asn Leu Asp
            660                 665                 670

Ala Glu Phe Arg His Asp Ser Gly Tyr Glu Val His His Gln Lys Leu
        675                 680                 685

Val Phe Phe Ala Glu Asp Val Gly Ser Asn Lys Gly Ala Ile Ile Gly
    690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
        755                 760                 765

Gln Asn
    770


<210> SEQ ID NO 14
<211> LENGTH: 467
<212> TYPE: PRT
<213> ORGANISM: MAMMALIAN
<220> FEATURE:
<221> NAME/KEY: MISC_FEATURE
<223> OTHER INFORMATION: Presenilin 1 (PS1) amino acid sequence (homo
      sapiens)

<400> SEQUENCE: 14

Met Thr Glu Leu Pro Ala Pro Leu Ser Tyr Phe Gln Asn Ala Gln Met
1               5                   10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45

Pro Leu Ser Asn Gly Arg Pro Gln Gly Asn Ser Arg Gln Val Val Glu
    50                  55                  60

Gln Asp Glu Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
            100                 105                 110

Leu Ile Tyr Thr Pro Phe Thr Glu Asp Thr Glu Thr Val Gly Gln Arg
        115                 120                 125

Ala Leu His Ser Ile Leu Asn Ala Ala Ile Met Ile Ser Val Ile Val
    130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175
```

```
Phe Ser Phe Ile Tyr Leu Gly Glu Val Phe Lys Thr Tyr Asn Val Ala
            180                 185                 190

Val Asp Tyr Ile Thr Val Ala Leu Leu Ile Trp Asn Phe Gly Val Val
        195                 200                 205

Gly Met Ile Ser Ile His Trp Lys Gly Pro Leu Arg Leu Gln Gln Ala
    210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
            260                 265                 270

Glu Thr Ala Gln Glu Arg Asn Glu Thr Leu Phe Pro Ala Leu Ile Tyr
        275                 280                 285

Ser Ser Thr Met Val Trp Leu Val Asn Met Ala Glu Gly Asp Pro Glu
    290                 295                 300

Ala Gln Arg Arg Val Ser Lys Asn Ser Lys Tyr Asn Ala Glu Ser Thr
305                 310                 315                 320

Glu Arg Glu Ser Gln Asp Thr Val Ala Glu Asn Asp Asp Gly Gly Phe
                325                 330                 335

Ser Glu Glu Trp Glu Ala Gln Arg Asp Ser His Leu Gly Pro His Arg
            340                 345                 350

Ser Thr Pro Glu Ser Arg Ala Ala Val Gln Glu Leu Ser Ser Ser Ile
        355                 360                 365

Leu Ala Gly Glu Asp Pro Glu Glu Arg Gly Val Lys Leu Gly Leu Gly
    370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Leu Ala Ile Phe Lys Lys Ala Leu
            420                 425                 430

Pro Ala Leu Pro Ile Ser Ile Thr Phe Gly Leu Val Phe Tyr Phe Ala
        435                 440                 445

Thr Asp Tyr Leu Val Gln Pro Phe Met Asp Gln Leu Ala Phe His Gln
    450                 455                 460

Phe Tyr Ile
465


<210> SEQ ID NO 15
<211> LENGTH: 467
<212> TYPE: PRT
<213> ORGANISM: MAMMALIAN
<220> FEATURE:
<221> NAME/KEY: MISC_FEATURE
<223> OTHER INFORMATION: PS1M146V : A single mutation at codon 146
      co-segregates with the disease in members of early-onset
      Alzheimer's disease families. A base pair change from the normal
      sequence predicts M to V amino acid substitution at codon 146.

<400> SEQUENCE: 15

Met Thr Glu Leu Pro Ala Pro Leu Ser Tyr Phe Gln Asn Ala Gln Met
1               5                   10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45
```

```
Pro Leu Ser Asn Gly Arg Pro Gln Gly Asn Ser Arg Gln Val Val Glu
    50                  55                  60

Gln Asp Glu Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
            100                 105                 110

Leu Ile Tyr Thr Pro Phe Thr Glu Asp Thr Glu Thr Val Gly Gln Arg
        115                 120                 125

Ala Leu His Ser Ile Leu Asn Ala Ala Ile Met Ile Ser Val Ile Val
    130                 135                 140

Val Val Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Ala
            180                 185                 190

Val Asp Tyr Ile Thr Val Ala Leu Leu Ile Trp Asn Phe Gly Val Val
        195                 200                 205

Gly Met Ile Ser Ile His Trp Lys Gly Pro Leu Arg Leu Gln Gln Ala
    210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
            260                 265                 270

Glu Thr Ala Gln Glu Arg Asn Glu Thr Leu Phe Pro Ala Leu Ile Tyr
        275                 280                 285

Ser Ser Thr Met Val Trp Leu Val Asn Met Ala Glu Gly Asp Pro Glu
    290                 295                 300

Ala Gln Arg Arg Val Ser Lys Asn Ser Lys Tyr Asn Ala Glu Ser Thr
305                 310                 315                 320

Glu Arg Glu Ser Gln Asp Thr Val Ala Glu Asn Asp Asp Gly Gly Phe
                325                 330                 335

Ser Glu Glu Trp Glu Ala Gln Arg Asp Ser His Leu Gly Pro His Arg
            340                 345                 350

Ser Thr Pro Glu Ser Arg Ala Ala Val Gln Glu Leu Ser Ser Ser Ile
        355                 360                 365

Leu Ala Gly Glu Asp Pro Glu Glu Arg Gly Val Lys Leu Gly Leu Gly
    370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Leu Ala Ile Phe Lys Lys Ala Leu
            420                 425                 430

Pro Ala Leu Pro Ile Ser Ile Thr Phe Gly Leu Val Phe Tyr Phe Ala
        435                 440                 445

Thr Asp Tyr Leu Val Gln Pro Phe Met Asp Gln Leu Ala Phe His Gln
    450                 455                 460

Phe Tyr Ile
465
```

<210> SEQ ID NO 16
<211> LENGTH: 83
<212> TYPE: PRT
<213> ORGANISM: MAMMALIAN
<220> FEATURE:
<221> NAME/KEY: MISC_FEATURE
<223> OTHER INFORMATION: 8 kDa CAPPalpha (C83)

<400> SEQUENCE: 16

```
Leu Val Phe Phe Ala Glu Asp Val Gly Ser Asn Lys Gly Ala Ile Ile
1               5                   10                  15

Gly Leu Met Val Gly Gly Val Val Ile Ala Thr Val Ile Val Ile Thr
            20                  25                  30

Leu Val Met Leu Lys Lys Lys Gln Tyr Thr Ser Ile His His Gly Val
        35                  40                  45

Val Glu Val Asp Ala Ala Val Thr Pro Glu Glu Arg His Leu Ser Lys
    50                  55                  60

Met Gln Gln Asn Gly Tyr Glu Asn Pro Thr Tyr Lys Phe Phe Glu Gln
65                  70                  75                  80

Met Gln Asn
```

<210> SEQ ID NO 17
<211> LENGTH: 4154
<212> TYPE: DNA
<213> ORGANISM: MAMMALIAN
<220> FEATURE:
<221> NAME/KEY: misc_feature
<223> OTHER INFORMATION: SREBP-1a; SREBP-1 (whole mRNA sequence from Gene Bank Accession No. U00968, GI:409404); CDS 167...3610; for cloning in pcDNA3.1, see SEQ ID Nos. 20 and 21; product is 1461 nucleotides (nucleotides 42-1503),
<220> FEATURE:
<223> OTHER INFORMATION: corresponding to -125 from start codon to 1336 of ORF: start codon ATG of ORF at nucleotides 167-169

<400> SEQUENCE: 17

```
taacgaggaa cttttcgccg gcgccgggcc gcctctgagg ccagggcagg acacgaacgc      60

gcggagcggc ggcggcgact gagagccggg gccgcggcgg cgctccctag gaagggccgt     120

acgaggcggc gggcccggcg ggcctcccgg aggaggcggc tgcgccatgg acgagccacc     180

cttcagcgag gcggctttgg agcaggcgct gggcgagccg tgcgatctgg acgcggcgct     240

gctgaccgac atcgaagaca tgcttcagct tatcaacaac caagacagtg acttccctgg     300

cctatttgac ccaccctatg ctgggagtgg ggcagggggc acagaccctg ccagccccga     360

taccagctcc ccaggcagct tgtctccacc tcctgccaca ttgagctcct ctcttgaagc     420

cttcctgagc gggccgcagg cagcgccctc acccctgtcc cctccccagc ctgcacccac     480

tccattgaag atgtacccgt ccatgcccgc tttctcccct gggcctggta tcaaggaaga     540

gtcagtgcca ctgagcatcc tgcagacccc caccccacag cccctgccag ggccctcct     600

gccacagagc ttcccagccc cagccccacc gcagttcagc tccacccctg tgttaggcta     660

ccccagccct ccgggaggct tctctacagg aagccctccc gggaacaccc agcagccgct     720

gcctggcctg ccactggctt ccccgccagg ggtcccgccc gtctccttgc acacccaggt     780

ccagagtgtg gtcccccagc agctactgac agtcacagct gcccccacgg cagcccctgt     840

aacgaccact gtgacctcgc agatccagca ggtcccggtc ctgctgcagc cccacttcat     900

caaggcagac tcgctgcttc tgacagccat gaagacagac ggagccactg tgaaggcggc     960

aggtctcagt cccctggtct ctggcaccac tgtgcagaca gggcctttgc cgaccctggt    1020
```

-continued

```
gagtggcgga accatcttgg caacagtccc actggtcgta gatgcggaga agctgcctat   1080
caaccggctc gcagctggca gcaaggcccc ggcctctgcc cagagccgtg gagagaagcg   1140
cacagcccac aacgccattg agaagcgcta ccgctcctcc atcaatgaca aaatcattga   1200
gctcaaggat ctggtggtgg gcactgaggc aaagctgaat aaatctgctg tcttgcgcaa   1260
ggccatcgac tacattcgct ttctgcaaca cagcaaccag aaactcaagc aggagaacct   1320
aagtctgcgc actgctgtcc acaaaagcaa atctctgaag gatctggtgt cggcctgtgg   1380
cagtggaggg aacacagacg tgctcatgga gggcgtgaag actgaggtgg aggacacact   1440
gaccccaccc ccctcggatg ctggctcacc tttccagagc agccccttgt cccttggcag   1500
caggggcagt ggcagcggtg gcagtggcag tgactcggag cctgacagcc cagtctttga   1560
ggacagcaag gcaaagccag agcagcggcc gtctctgcac agccggggca tgctggaccg   1620
ctcccgcctg gccctgtgca cgctcgtctt cctctgcctg tcctgcaacc ccttggcctc   1680
cttgctgggg gcccgggggc ttcccagccc ctcagatacc accagcgtct accatagccc   1740
tgggcgcaac gtgctgggca ccgagagcag agatggccct ggctgggccc agtggctgct   1800
gcccccagtg gtctggctgc tcaatgggct gttggtgctc gtctccttgg tgcttctctt   1860
tgtctacggt gagccagtca cacggcccca ctcaggcccc gccgtgtact tctggaggca   1920
tcgcaagcag gctgacctgg acctggcccg gggagacttt gcccaggctg cccagcagct   1980
gtggctggcc ctgcgggcac tgggccggcc cctgcccacc tcccacctgg acctggcttg   2040
tagcctcctc tggaacctca tccgtcacct gctgcagcgt ctctgggtgg gccgctggct   2100
ggcaggccgg gcagggggcc tgcagcagga ctgtgctctg cgagtggatg ctagcgccag   2160
cgcccgagac gcagccctgg tctaccataa gctgcaccag ctgcacacca tggggaagca   2220
cacaggcggg cacctcactg ccaccaacct ggcgctgagt gccctgaacc tggcagagtg   2280
tgcaggggat gccgtgtctg tggcgacgct ggccgagatc tatgtggcgg ctgcattgag   2340
agtgaagacc agtctcccac gggccttgca ttttctgaca cgcttcttcc tgagcagtgc   2400
ccgccaggcc tgcctggcac agagtggctc agtgcctcct gccatgcagt ggctctgcca   2460
ccccgtgggc caccgtttct tcgtggatgg ggactggtcc gtgctcagta ccccatggga   2520
gagcctgtac agcttggccg ggaacccagt ggacccccctg gcccaggtga ctcagctatt   2580
ccgggaacat ctcttagagc gagcactgaa ctgtgtgacc cagcccaacc ccagccctgg   2640
gtcagctgat ggggacaagg aattctcgga tgccctcggg tacctgcagc tgctgaacag   2700
ctgttctgat gctgcggggg ctcctgccta cagcttctcc atcagttcca gcatggccac   2760
caccaccggc gtagacccgg tggccaagtg gtgggcctct ctgacagctg tggtgatcca   2820
ctggctgcgg cgggatgagg aggcggctga gcggctgtgc ccgctggtgg agcacctgcc   2880
ccgggtgctg caggagtctg agagacccct gcccagggca gctctgcact ccttcaaggc   2940
tgcccgggcc ctgctgggct gtgccaaggc agagtctggt ccagccagcc tgaccatctg   3000
tgagaaggcc agtgggtacc tgcaggacag cctggctacc acaccagcca gcagctccat   3060
tgacaaggcc gtgcagctgt tcctgtgtga cctgcttctt gtggtgcgca ccagcctgtg   3120
gcggcagcag cagcccccgg ccccggcccc agcagcccag ggcgccagca gcaggcccca   3180
ggcttccgcc cttgagctgc gtggcttcca acgggacctg agcagcctga ggcggctggc   3240
acagagcttc cggcccgcca tgcggagggt gttcctacat gaggccacgg cccggctgat   3300
ggcgggggcc agccccacac ggacacacca gctcctcgac cgcagtctga ggcggcgggc   3360
aggccccggt ggcaaaggag gcgcggtggc ggagctggag ccgcggccca cgcggcggga   3420
```

```
gcacgcggag gccttgctgc tggcctcctg ctacctgccc cccggcttcc tgtcggcgcc   3480

cgggcagcgc gtgggcatgc tggctgaggc ggcgcgcaca ctcgagaagc ttggcgatcg   3540

ccggctgctg cacgactgtc agcagatgct catgcgcctg ggcggtggga ccactgtcac   3600

ttccagctag accccgtgtc cccggcctca gcacccctgt ctctagccac tttggtcccg   3660

tgcagcttct gtcctgcgtc gaagctttga aggccgaagg cagtgcaaga gactctggcc   3720

tccacagttc gacctgcggc tgctgtgtgc cttcgcggtg gaaggcccga ggggcgcgat   3780

cttgacccta agaccggcgg ccatgatggt gctgacctct ggtggccgat cggggcactg   3840

caggggccga gccattttgg ggggcccccc tccttgctct gcaggcacct tagtggcttt   3900

tttcctcctg tgtacaggga agagaggggt acatttccct gtgctgacgg aagccaactt   3960

ggctttcccg gactgcaagc agggctctgc cccagaggcc tctctctccg tcgtgggaga   4020

gagacgtgta catagtgtag gtcagcgtgc ttagcctcct gacctgaggc tcctgtgcta   4080

ctttgccttt tgcaaacttt attttcatag attgagaagt tttgtacaga gaattaaaaa   4140

tgaaattatt tata                                                     4154
```

<210> SEQ ID NO 18
<211> LENGTH: 1123
<212> TYPE: PRT
<213> ORGANISM: MAMMALIAN
<220> FEATURE:
<221> NAME/KEY: MISC_FEATURE
<223> OTHER INFORMATION: SREBP-1c amino acid sequence; identical to SREBP-1a (SEQ ID NO: 24) except amino acid residues 1-6 of SREBP-1c (from SREBP-1c specific exon) differ from residues 1-30 of SREBP-1a (SEQ ID NO: 24)

<400> SEQUENCE: 18

```
Met Asp Cys Thr Phe Glu Asp Met Leu Gln Leu Ile Asn Asn Gln Asp
1               5                   10                  15

Ser Asp Phe Pro Gly Leu Phe Asp Pro Pro Tyr Ala Gly Ser Gly Ala
            20                  25                  30

Gly Gly Thr Asp Pro Ala Ser Pro Asp Thr Ser Ser Pro Gly Ser Leu
        35                  40                  45

Ser Pro Pro Pro Ala Thr Leu Ser Ser Ser Leu Glu Ala Phe Leu Ser
    50                  55                  60

Gly Pro Gln Ala Ala Pro Ser Pro Leu Ser Pro Pro Gln Pro Ala Pro
65                  70                  75                  80

Thr Pro Leu Lys Met Tyr Pro Ser Met Pro Ala Phe Ser Pro Gly Pro
                85                  90                  95

Gly Ile Lys Glu Glu Ser Val Pro Leu Ser Ile Leu Gln Thr Pro Thr
            100                 105                 110

Pro Gln Pro Leu Pro Gly Ala Leu Leu Pro Gln Ser Phe Pro Ala Pro
        115                 120                 125

Ala Pro Pro Gln Phe Ser Ser Thr Pro Val Leu Gly Tyr Pro Ser Pro
    130                 135                 140

Pro Gly Gly Phe Ser Thr Gly Ser Pro Pro Gly Asn Thr Gln Gln Pro
145                 150                 155                 160

Leu Pro Gly Leu Pro Leu Ala Ser Pro Pro Gly Val Pro Pro Val Ser
                165                 170                 175

Leu His Thr Gln Val Gln Ser Val Val Pro Gln Gln Leu Leu Thr Val
            180                 185                 190

Thr Ala Ala Pro Thr Ala Ala Pro Val Thr Thr Thr Val Thr Ser Gln
        195                 200                 205

Ile Gln Gln Val Pro Val Leu Leu Gln Pro His Phe Ile Lys Ala Asp
```

```
    210                 215                 220

Ser Leu Leu Leu Thr Ala Met Lys Thr Asp Gly Ala Thr Val Lys Ala
225                 230                 235                 240

Ala Gly Leu Ser Pro Leu Val Ser Gly Thr Thr Val Gln Thr Gly Pro
                245                 250                 255

Leu Pro Thr Leu Val Ser Gly Gly Thr Ile Leu Ala Thr Val Pro Leu
            260                 265                 270

Val Val Asp Ala Glu Lys Leu Pro Ile Asn Arg Leu Ala Ala Gly Ser
        275                 280                 285

Lys Ala Pro Ala Ser Ala Gln Ser Arg Gly Glu Lys Arg Thr Ala His
    290                 295                 300

Asn Ala Ile Glu Lys Arg Tyr Arg Ser Ser Ile Asn Asp Lys Ile Ile
305                 310                 315                 320

Glu Leu Lys Asp Leu Val Val Gly Thr Glu Ala Lys Leu Asn Lys Ser
                325                 330                 335

Ala Val Leu Arg Lys Ala Ile Asp Tyr Ile Arg Phe Leu Gln His Ser
            340                 345                 350

Asn Gln Lys Leu Lys Gln Glu Asn Leu Ser Leu Arg Thr Ala Val His
        355                 360                 365

Lys Ser Lys Ser Leu Lys Asp Leu Val Ser Ala Cys Gly Ser Gly Gly
    370                 375                 380

Asn Thr Asp Val Leu Met Glu Gly Val Lys Thr Glu Val Glu Asp Thr
385                 390                 395                 400

Leu Thr Pro Pro Pro Ser Asp Ala Gly Ser Pro Phe Gln Ser Ser Pro
                405                 410                 415

Leu Ser Leu Gly Ser Arg Gly Ser Gly Ser Gly Gly Ser Gly Ser Asp
            420                 425                 430

Ser Glu Pro Asp Ser Pro Val Phe Glu Asp Ser Lys Ala Lys Pro Glu
        435                 440                 445

Gln Arg Pro Ser Leu His Ser Arg Gly Met Leu Asp Arg Ser Arg Leu
    450                 455                 460

Ala Leu Cys Thr Leu Val Phe Leu Cys Leu Ser Cys Asn Pro Leu Ala
465                 470                 475                 480

Ser Leu Leu Gly Ala Arg Gly Leu Pro Ser Pro Ser Asp Thr Thr Ser
                485                 490                 495

Val Tyr His Ser Pro Gly Arg Asn Val Leu Gly Thr Glu Ser Arg Asp
            500                 505                 510

Gly Pro Gly Trp Ala Gln Trp Leu Leu Pro Pro Val Val Trp Leu Leu
        515                 520                 525

Asn Gly Leu Leu Val Leu Val Ser Leu Val Leu Leu Phe Val Tyr Gly
    530                 535                 540

Glu Pro Val Thr Arg Pro His Ser Gly Pro Ala Val Tyr Phe Trp Arg
545                 550                 555                 560

His Arg Lys Gln Ala Asp Leu Asp Leu Ala Arg Gly Asp Phe Ala Gln
                565                 570                 575

Ala Ala Gln Gln Leu Trp Leu Ala Leu Arg Ala Leu Gly Arg Pro Leu
            580                 585                 590

Pro Thr Ser His Leu Asp Leu Ala Cys Ser Leu Leu Trp Asn Leu Ile
        595                 600                 605

Arg His Leu Leu Gln Arg Leu Trp Val Gly Arg Trp Leu Ala Gly Arg
    610                 615                 620

Ala Gly Gly Leu Gln Gln Asp Cys Ala Leu Arg Val Asp Ala Ser Ala
625                 630                 635                 640
```

```
Ser Ala Arg Asp Ala Ala Leu Val Tyr His Lys Leu His Gln Leu His
                645                 650                 655

Thr Met Gly Lys His Thr Gly Gly His Leu Thr Ala Thr Asn Leu Ala
            660                 665                 670

Leu Ser Ala Leu Asn Leu Ala Glu Cys Ala Gly Asp Ala Val Ser Val
        675                 680                 685

Ala Thr Leu Ala Glu Ile Tyr Val Ala Ala Ala Leu Arg Val Lys Thr
    690                 695                 700

Ser Leu Pro Arg Ala Leu His Phe Leu Thr Arg Phe Phe Leu Ser Ser
705                 710                 715                 720

Ala Arg Gln Ala Cys Leu Ala Gln Ser Gly Ser Val Pro Pro Ala Met
                725                 730                 735

Gln Trp Leu Cys His Pro Val Gly His Arg Phe Phe Val Asp Gly Asp
            740                 745                 750

Trp Ser Val Leu Ser Thr Pro Trp Glu Ser Leu Tyr Ser Leu Ala Gly
        755                 760                 765

Asn Pro Val Asp Pro Leu Ala Gln Val Thr Gln Leu Phe Arg Glu His
    770                 775                 780

Leu Leu Glu Arg Ala Leu Asn Cys Val Thr Gln Pro Asn Pro Ser Pro
785                 790                 795                 800

Gly Ser Ala Asp Gly Asp Lys Glu Phe Ser Asp Ala Leu Gly Tyr Leu
                805                 810                 815

Gln Leu Leu Asn Ser Cys Ser Asp Ala Ala Gly Ala Pro Ala Tyr Ser
            820                 825                 830

Phe Ser Ile Ser Ser Ser Met Ala Thr Thr Thr Gly Val Asp Pro Val
        835                 840                 845

Ala Lys Trp Trp Ala Ser Leu Thr Ala Val Val Ile His Trp Leu Arg
    850                 855                 860

Arg Asp Glu Glu Ala Ala Glu Arg Leu Cys Pro Leu Val Glu His Leu
865                 870                 875                 880

Pro Arg Val Leu Gln Glu Ser Glu Arg Pro Leu Pro Arg Ala Ala Leu
                885                 890                 895

His Ser Phe Lys Ala Ala Arg Ala Leu Leu Gly Cys Ala Lys Ala Glu
            900                 905                 910

Ser Gly Pro Ala Ser Leu Thr Ile Cys Glu Lys Ala Ser Gly Tyr Leu
        915                 920                 925

Gln Asp Ser Leu Ala Thr Thr Pro Ala Ser Ser Ser Ile Asp Lys Ala
    930                 935                 940

Val Gln Leu Phe Leu Cys Asp Leu Leu Leu Val Val Arg Thr Ser Leu
945                 950                 955                 960

Trp Arg Gln Gln Gln Pro Pro Ala Pro Ala Pro Ala Ala Gln Gly Ala
                965                 970                 975

Ser Ser Arg Pro Gln Ala Ser Ala Leu Glu Leu Arg Gly Phe Gln Arg
            980                 985                 990

Asp Leu Ser Ser Leu Arg Arg Leu  Ala Gln Ser Phe Arg  Pro Ala Met
        995                 1000                1005

Arg Arg  Val Phe Leu His Glu  Ala Thr Ala Arg Leu  Met Ala Gly
    1010                1015                1020

Ala Ser  Pro Thr Arg Thr His  Gln Leu Leu Asp Arg  Ser Leu Arg
    1025                1030                1035

Arg Arg  Ala Gly Pro Gly Gly  Lys Gly Gly Ala Val  Ala Glu Leu
    1040                1045                1050

Glu Pro  Arg Pro Thr Arg Arg  Glu His Ala Glu Ala  Leu Leu Leu
    1055                1060                1065
```

```
Ala Ser Cys Tyr Leu Pro Pro Gly Phe Leu Ser Ala Pro Gly Gln
    1070                1075                1080

Arg Val Gly Met Leu Ala Glu Ala Ala Arg Thr Leu Glu Lys Leu
    1085                1090                1095

Gly Asp Arg Arg Leu Leu His Asp Cys Gln Gln Met Leu Met Arg
    1100                1105                1110

Leu Gly Gly Gly Thr Thr Val Thr Ser Ser
    1115                1120
```

<210> SEQ ID NO 19
<211> LENGTH: 4249
<212> TYPE: DNA
<213> ORGANISM: MAMMALIAN
<220> FEATURE:
<221> NAME/KEY: misc_feature
<223> OTHER INFORMATION: SREBP-2; whole mRNA sequence from Gene Bank Accession No. U02031, GI:451329; CDS 118...3543; for cloning in pcDNA3.1, see SEQ ID Nos. 22 and 23; product is 1492 nucleotides (nucleotides 27-1519),
<220> FEATURE:
<223> OTHER INFORMATION: corresponding to nucleotide -91 from start codon to nucleotide 1401 of ORF: start ATG sequence of ORF at nucleotides 118-120

<400> SEQUENCE: 19

```
ccgtcggtga ggcggtgccg ggcgggggtt gtcgggtgtc atgggcggtg gcgacggcac     60
cgcccccgcg tctccctgag cgggacggca ggggggggctt ctgcgctgag ccgggcgatg    120
gacgacagcg gcgagctggg tggtctggag accatggaga ccctcacgga gctgggcgac    180
gagctgaccc tgggagacat cgacgagatg ctgcaatttg tcagtaatca agtgggagag    240
ttccctgact tgttttcaga acagctgtgt agctcctttc ctggcagtgg tggtagtggt    300
agcagcagcg gcagcagtgg cagcagcagc agcagcagca atggcagggg cagcagcagc    360
ggagctgtgg acccttcagt gcaacggtca ttcacccagg tcacattacc ttccttctct    420
ccctcggcgg cctccccaca ggctccaact ctgcaagtca aggtttctcc cacctcagtt    480
cccaccacac ccagggcaac tcctattctt cagccccgcc cccagcccca gcctcaacct    540
caaactcagc tgcaacaaca gacggtaatg atcacgccaa cattcagcac cactccgcag    600
acgaggatca tccagcagcc tttgatatac cagaatgcag ctactagctt tcaagtcctt    660
cagcctcaag tccaaagcct ggtgacatcc tcccaggtac agccggtcac cattcagcag    720
caggtgcaga cagtacaggc ccagcgggtg ctgacacaaa cggccaatgg cacgctgcag    780
acccttgccc cggctacggt gcagacagtt gctgcgccac aggtgcagca ggtcccggtc    840
ctggtccagc ctcagatcat caagacagat tcccttgttt tgaccacact gaagacagat    900
ggcagccctg ttatggctgc ggtccagaac ccggccctca ccgccctcac cacccctatc    960
cagacggctg cccttcaagt accaaccctg gtgggcagca gtgggaccat tctgaccaca   1020
atgcctgtaa tgatggggca agagaaagtg cccattaagc aggtacctgg gggagtcaag   1080
cagcttgagc cccccaaaga aggagaaagg cggacaaccc ataatatcat tgagaaacga   1140
tatcgctcct ccatcaatga caaaatcatc gaattgaaag acctggtcat ggggacagac   1200
gccaagatgc acaagtctgg cgttctgagg aaggccattg attacatcaa atacttgcag   1260
caggtcaatc ataaactgcg ccaggagaac atggtgctga agctggcaaa tcaaaagaac   1320
aagcttctaa agggcatcga cctaggcagt ctggtggaca atgaggtgga cctgaagatc   1380
gaggacttta atcagaatgt ccttctgatg tcccccccag cctctgactc agggtcccag   1440
gctggcttct ctccctactc cattgactct gagccaggaa gccctctatt ggatgatgca   1500
```

```
aaggtcaaag atgagccaga ctctcctcct gtggcgctgg gcatggtaga ccgctcacgg   1560
attcttctgt gtgtcctcac cttcctgtgc ctctccttta accccctgac ttccctgctg   1620
cagtggggag gggcccacga ctctgaccag cacccacact caggctctgg ccgcagtgtc   1680
ctgtcattcg agtcaggttc tgggggctgg tttgactgga tgatgcctac tcttctctta   1740
tggctggtaa atggtgtgat tgtcctgagc gtctttgtga agctgctggt tcatggggag   1800
ccagtgatcc ggccacactc gcgctcctcg gtcaccttct ggaggcaccg gaaacaggca   1860
gatctggatc tcgccagagg agattttgca gctgctgccg ccaacctaca aacctgcctg   1920
gcagttttgg gccgggcact gcccacctcc cgcctggacc tggcctgcag cctctcctgg   1980
aacgtgatcc gctacagcct gcagaagcta cgcctggtgc gctggctgct caagaaagtc   2040
ttccagtgcc ggcgggccac gccagccact gaggcaggct ttgaagacga agctaagacc   2100
agcgcccggg atgcggctct ggcctatcac cggctgcacc agctgcacat cacagggaag   2160
cttcctgcag gatccgcctg ttccgatgta cacatggcgt tgtgtgccgt gaacctggct   2220
gaatgtgcag aggagaagat cccaccgagc acactggttg agatccatct gactgctgcc   2280
atggggctca agacccggtg tggaggcaag ctgggcttcc tggccagcta cttcctcagc   2340
cgagcccaga gcctgtgtgg ccccgagcac agtgctgttc ctgactccct gcgctggctc   2400
tgccaccccc tgggccagaa gtttttcatg gagcggagct ggtctgtgaa gtcagctgcc   2460
aaggagagtc tatactgtgc ccagaggaac ccagctgacc ccattgcgca ggtccaccag   2520
gccttctgca agaacctgct ggagcgagct atagagtcct tggtgaaacc tcaggccaag   2580
aagaaggctg gagaccagga agaagagagc tgtgaattct ccagtgctct ggagtacttg   2640
aaattacttc attcttttgt ggactctgtg gggttatga gccccccact ctccaggagc   2700
tccgtgctca agtccgccct gggtccagac atcatctgtc ggtggtggac gtctgcaatc   2760
actgtggcca tcagctggct ccagggagac gatgcagctg tgcgctctca ttttaccaaa   2820
gtggaacgca tccccaaggc cctggaagtg acagagagcc ccctggtgaa ggccatcttc   2880
catgcctgca gagccatgca tgcctcactc cctgggaaag cagatgggca gcagagttcc   2940
ttctgccatt gcgagagggc cagtggccac ctatggagca gcctcaacgt cagtgggggc   3000
acctctgacc ctgccctcaa ccacgtggtc cagctgctca cctgtgacct gctactgtcg   3060
ctacggacag cgctctggca aaaacaggcc agtgccagcc aggctgtggg ggagacctac   3120
cacgcgtcag gcgctgaact ggcgggcttc caacgggacc tgggcagcct gcgcaggctg   3180
gcacacagct tccgcccagc ataccgcaag gtgttcctgc atgaagccac cgtgcgcctg   3240
atggcaggag gcagccccac ccgcacccac cagctgctgg aacacagcct gcggcggcgc   3300
accacgcaga gcaccaagca cggagaggtg gatgcctggc ccggccagcg agagcgggcc   3360
accgccatcc tgctggcctg ccgccacctg cccctctcct tcctctcctc cccgggccag   3420
cgggcagtgc tgctggccga agctgcccgc accctggaga aggtgggcga ccggcgctcc   3480
tgcaacgact gccagcagat gattgttaag ctgggtggtg gcactgccat tgccgcctcc   3540
tgaccaccag gctcagccca cccctccacc tctctctcga tttctctctc tccccctcag   3600
catcttcccg ctgagagtgg tggggaagag ccttgtcttc ttagctgtca cctgccgagg   3660
cttctgggcc actcaggcca gtgcacccct gggcagagcc ccttaaagct gctgtcacta   3720
gatgcccatg gtccagggcc tggtgggcgt gagaggatag gtggcagggc agaaactggg   3780
cagccctgac ttgatagcag caggggggagc tcccaagctg ccaagcccct gcctccagcc   3840
ttcctgagtt tctctctcct gaaccctact ctctcctttt tgcttcctca gtttttatca   3900
```

```
ggctttctct gggggacagc agtctctgag caccagggag cagttgccct caggcctgtg   3960

cccagcatgc cctccccttt ttatacgaat gttttctacc agtgtgcttg ggtttgccat   4020

gatgcgaggc tgagttgctg tagcgtcttg attctctccc tgggtctgcg ttccctcccc   4080

tgggcctgac tgagcctgct cattgttttt ccctttatta cacaggacag ccaggggagg   4140

agggggcccc agccctggga ggctggtggg aggcaggggg caggcctgcg gatgcatgaa   4200

ataatgttgg cattattttt taattttta aaaaataaat ggtatctta               4249


<210> SEQ ID NO 20
<211> LENGTH: 28
<212> TYPE: DNA
<213> ORGANISM: MAMMALIAN
<220> FEATURE:
<221> NAME/KEY: misc_feature
<223> OTHER INFORMATION: SREBP-1 forward primer; BamHI site at
      nucleotides 5-10; target sequence at nucleotides 13-28

<400> SEQUENCE: 20

gagaggatcc aacagggcag gacacgaa                                        28


<210> SEQ ID NO 21
<211> LENGTH: 28
<212> TYPE: DNA
<213> ORGANISM: MAMMALIAN
<220> FEATURE:
<221> NAME/KEY: misc_feature
<223> OTHER INFORMATION: SREBP-1 reverse primer; EcoRI site at
      nucleotides 5-10; target sequence at nucleotides 13-28

<400> SEQUENCE: 21

gagagaattc ggctgctgcc aagggaca                                        28


<210> SEQ ID NO 22
<211> LENGTH: 29
<212> TYPE: DNA
<213> ORGANISM: MAMMALIAN
<220> FEATURE:
<221> NAME/KEY: misc_feature
<223> OTHER INFORMATION: SREBP-2 forward primer; BamHI site at
      nucleotides 5-10; target sequence at nucleotides 13-29

<400> SEQUENCE: 22

gagaggatcc aaggttgtcg ggtgtcatg                                       29


<210> SEQ ID NO 23
<211> LENGTH: 31
<212> TYPE: DNA
<213> ORGANISM: MAMMALIAN
<220> FEATURE:
<221> NAME/KEY: misc_feature
<223> OTHER INFORMATION: SREBP-2 reverse primer; EcoRI site at
      nucleotides 5-10; target sequence at nucleotides 13-31

<400> SEQUENCE: 23

gagagaattc ggctggctca tctttgacct t                                    31


<210> SEQ ID NO 24
<211> LENGTH: 1147
<212> TYPE: PRT
<213> ORGANISM: MAMMALIAN
<220> FEATURE:
<221> NAME/KEY: MISC_FEATURE
<223> OTHER INFORMATION: Whole SREBP-1 protein amino-acid sequence
      shown. The PCR product generates an NH2-terminal fragment
      of SREBP-1 (amino acid residues 1-445), a dominant
      positive fragment of SREBP-1
```

<400> SEQUENCE: 24

```
Met Asp Glu Pro Pro Phe Ser Glu Ala Ala Leu Glu Gln Ala Leu Gly
1               5                   10                  15

Glu Pro Cys Asp Leu Asp Ala Ala Leu Leu Thr Asp Ile Glu Asp Met
            20                  25                  30

Leu Gln Leu Ile Asn Asn Gln Asp Ser Asp Phe Pro Gly Leu Phe Asp
        35                  40                  45

Pro Pro Tyr Ala Gly Ser Gly Ala Gly Gly Thr Asp Pro Ala Ser Pro
    50                  55                  60

Asp Thr Ser Ser Pro Gly Ser Leu Ser Pro Pro Pro Ala Thr Leu Ser
65                  70                  75                  80

Ser Ser Leu Glu Ala Phe Leu Ser Gly Pro Gln Ala Ala Pro Ser Pro
                85                  90                  95

Leu Ser Pro Pro Gln Pro Ala Pro Thr Pro Leu Lys Met Tyr Pro Ser
            100                 105                 110

Met Pro Ala Phe Ser Pro Gly Pro Gly Ile Lys Glu Glu Ser Val Pro
        115                 120                 125

Leu Ser Ile Leu Gln Thr Pro Thr Pro Gln Pro Leu Pro Gly Ala Leu
    130                 135                 140

Leu Pro Gln Ser Phe Pro Ala Pro Ala Pro Pro Gln Phe Ser Ser Thr
145                 150                 155                 160

Pro Val Leu Gly Tyr Pro Ser Pro Pro Gly Gly Phe Ser Thr Gly Ser
                165                 170                 175

Pro Pro Gly Asn Thr Gln Gln Pro Leu Pro Gly Leu Pro Leu Ala Ser
            180                 185                 190

Pro Pro Gly Val Pro Pro Val Ser Leu His Thr Gln Val Gln Ser Val
        195                 200                 205

Val Pro Gln Gln Leu Leu Thr Val Thr Ala Ala Pro Thr Ala Ala Pro
    210                 215                 220

Val Thr Thr Thr Val Thr Ser Gln Ile Gln Gln Val Pro Val Leu Leu
225                 230                 235                 240

Gln Pro His Phe Ile Lys Ala Asp Ser Leu Leu Leu Thr Ala Met Lys
                245                 250                 255

Thr Asp Gly Ala Thr Val Lys Ala Ala Gly Leu Ser Pro Leu Val Ser
            260                 265                 270

Gly Thr Thr Val Gln Thr Gly Pro Leu Pro Thr Leu Val Ser Gly Gly
        275                 280                 285

Thr Ile Leu Ala Thr Val Pro Leu Val Val Asp Ala Glu Lys Leu Pro
    290                 295                 300

Ile Asn Arg Leu Ala Ala Gly Ser Lys Ala Pro Ala Ser Ala Gln Ser
305                 310                 315                 320

Arg Gly Glu Lys Arg Thr Ala His Asn Ala Ile Glu Lys Arg Tyr Arg
                325                 330                 335

Ser Ser Ile Asn Asp Lys Ile Ile Glu Leu Lys Asp Leu Val Val Gly
            340                 345                 350

Thr Glu Ala Lys Leu Asn Lys Ser Ala Val Leu Arg Lys Ala Ile Asp
        355                 360                 365

Tyr Ile Arg Phe Leu Gln His Ser Asn Gln Lys Leu Lys Gln Glu Asn
    370                 375                 380

Leu Ser Leu Arg Thr Ala Val His Lys Ser Lys Ser Leu Lys Asp Leu
385                 390                 395                 400

Val Ser Ala Cys Gly Ser Gly Gly Asn Thr Asp Val Leu Met Glu Gly
                405                 410                 415
```

```
Val Lys Thr Glu Val Glu Asp Thr Leu Thr Pro Pro Pro Ser Asp Ala
            420                 425                 430

Gly Ser Pro Phe Gln Ser Ser Pro Leu Ser Leu Gly Ser Arg Gly Ser
        435                 440                 445

Gly Ser Gly Gly Ser Gly Ser Asp Ser Glu Pro Asp Ser Pro Val Phe
    450                 455                 460

Glu Asp Ser Lys Ala Lys Pro Glu Gln Arg Pro Ser Leu His Ser Arg
465                 470                 475                 480

Gly Met Leu Asp Arg Ser Arg Leu Ala Leu Cys Thr Leu Val Phe Leu
                485                 490                 495

Cys Leu Ser Cys Asn Pro Leu Ala Ser Leu Leu Gly Ala Arg Gly Leu
            500                 505                 510

Pro Ser Pro Ser Asp Thr Thr Ser Val Tyr His Ser Pro Gly Arg Asn
        515                 520                 525

Val Leu Gly Thr Glu Ser Arg Asp Gly Pro Gly Trp Ala Gln Trp Leu
    530                 535                 540

Leu Pro Pro Val Val Trp Leu Leu Asn Gly Leu Leu Val Leu Val Ser
545                 550                 555                 560

Leu Val Leu Leu Phe Val Tyr Gly Glu Pro Val Thr Arg Pro His Ser
                565                 570                 575

Gly Pro Ala Val Tyr Phe Trp Arg His Arg Lys Gln Ala Asp Leu Asp
            580                 585                 590

Leu Ala Arg Gly Asp Phe Ala Gln Ala Ala Gln Gln Leu Trp Leu Ala
        595                 600                 605

Leu Arg Ala Leu Gly Arg Pro Leu Pro Thr Ser His Leu Asp Leu Ala
    610                 615                 620

Cys Ser Leu Leu Trp Asn Leu Ile Arg His Leu Leu Gln Arg Leu Trp
625                 630                 635                 640

Val Gly Arg Trp Leu Ala Gly Arg Ala Gly Gly Leu Gln Gln Asp Cys
                645                 650                 655

Ala Leu Arg Val Asp Ala Ser Ala Ser Ala Arg Asp Ala Ala Leu Val
            660                 665                 670

Tyr His Lys Leu His Gln Leu His Thr Met Gly Lys His Thr Gly Gly
        675                 680                 685

His Leu Thr Ala Thr Asn Leu Ala Leu Ser Ala Leu Asn Leu Ala Glu
    690                 695                 700

Cys Ala Gly Asp Ala Val Ser Val Ala Thr Leu Ala Glu Ile Tyr Val
705                 710                 715                 720

Ala Ala Ala Leu Arg Val Lys Thr Ser Leu Pro Arg Ala Leu His Phe
                725                 730                 735

Leu Thr Arg Phe Phe Leu Ser Ser Ala Arg Gln Ala Cys Leu Ala Gln
            740                 745                 750

Ser Gly Ser Val Pro Pro Ala Met Gln Trp Leu Cys His Pro Val Gly
        755                 760                 765

His Arg Phe Phe Val Asp Gly Asp Trp Ser Val Leu Ser Thr Pro Trp
    770                 775                 780

Glu Ser Leu Tyr Ser Leu Ala Gly Asn Pro Val Asp Pro Leu Ala Gln
785                 790                 795                 800

Val Thr Gln Leu Phe Arg Glu His Leu Leu Glu Arg Ala Leu Asn Cys
                805                 810                 815

Val Thr Gln Pro Asn Pro Ser Pro Gly Ser Ala Asp Gly Asp Lys Glu
            820                 825                 830

Phe Ser Asp Ala Leu Gly Tyr Leu Gln Leu Leu Asn Ser Cys Ser Asp
```

```
        835                 840                 845

Ala Ala Gly Ala Pro Ala Tyr Ser Phe Ser Ile Ser Ser Ser Met Ala
    850                 855                 860

Thr Thr Thr Gly Val Asp Pro Val Ala Lys Trp Trp Ala Ser Leu Thr
865                 870                 875                 880

Ala Val Val Ile His Trp Leu Arg Arg Asp Glu Glu Ala Ala Glu Arg
                885                 890                 895

Leu Cys Pro Leu Val Glu His Leu Pro Arg Val Leu Gln Glu Ser Glu
            900                 905                 910

Arg Pro Leu Pro Arg Ala Ala Leu His Ser Phe Lys Ala Ala Arg Ala
        915                 920                 925

Leu Leu Gly Cys Ala Lys Ala Glu Ser Gly Pro Ala Ser Leu Thr Ile
    930                 935                 940

Cys Glu Lys Ala Ser Gly Tyr Leu Gln Asp Ser Leu Ala Thr Thr Pro
945                 950                 955                 960

Ala Ser Ser Ser Ile Asp Lys Ala Val Gln Leu Phe Leu Cys Asp Leu
                965                 970                 975

Leu Leu Val Val Arg Thr Ser Leu Trp Arg Gln Gln Gln Pro Pro Ala
            980                 985                 990

Pro Ala Pro Ala Ala Gln Gly Ala  Ser Ser Arg Pro Gln  Ala Ser Ala
        995                 1000                 1005

Leu Glu  Leu Arg Gly Phe Gln  Arg Asp Leu Ser Ser  Leu Arg Arg
    1010                 1015                 1020

Leu Ala  Gln Ser Phe Arg Pro  Ala Met Arg Arg Val  Phe Leu His
    1025                 1030                 1035

Glu Ala  Thr Ala Arg Leu Met  Ala Gly Ala Ser Pro  Thr Arg Thr
    1040                 1045                 1050

His Gln  Leu Leu Asp Arg Ser  Leu Arg Arg Arg Ala  Gly Pro Gly
    1055                 1060                 1065

Gly Lys  Gly Gly Ala Val Ala  Glu Leu Glu Pro Arg  Pro Thr Arg
    1070                 1075                 1080

Arg Glu  His Ala Glu Ala Leu  Leu Leu Ala Ser Cys  Tyr Leu Pro
    1085                 1090                 1095

Pro Gly  Phe Leu Ser Ala Pro  Gly Gln Arg Val Gly  Met Leu Ala
    1100                 1105                 1110

Glu Ala  Ala Arg Thr Leu Glu  Lys Leu Gly Asp Arg  Arg Leu Leu
    1115                 1120                 1125

His Asp  Cys Gln Gln Met Leu  Met Arg Leu Gly Gly  Gly Thr Thr
    1130                 1135                 1140

Val Thr  Ser Ser
    1145
```

<210> SEQ ID NO 25
<211> LENGTH: 1141
<212> TYPE: PRT
<213> ORGANISM: MAMMALIAN
<220> FEATURE:
<221> NAME/KEY: MISC_FEATURE
<223> OTHER INFORMATION: Whole SREBP-2 protein amino-acid sequence shown. The PCR product generates an NH2-terminal fragment of SREBP-2 (amino acid residues 1-467), a dominant positive fragment of SREBP-2

<400> SEQUENCE: 25

```
Met Asp Asp Ser Gly Glu Leu Gly Gly Leu Glu Thr Met Glu Thr Leu
1               5                   10                  15

Thr Glu Leu Gly Asp Glu Leu Thr Leu Gly Asp Ile Asp Glu Met Leu
```

```
            20                  25                  30

Gln Phe Val Ser Asn Gln Val Gly Glu Phe Pro Asp Leu Phe Ser Glu
        35                  40                  45

Gln Leu Cys Ser Ser Phe Pro Gly Ser Gly Gly Ser Gly Ser Ser Ser
    50                  55                  60

Gly Ser Ser Gly Ser Ser Ser Ser Ser Ser Asn Gly Arg Gly Ser Ser
65                  70                  75                  80

Ser Gly Ala Val Asp Pro Ser Val Gln Arg Ser Phe Thr Gln Val Thr
                85                  90                  95

Leu Pro Ser Phe Ser Pro Ser Ala Ala Ser Pro Gln Ala Pro Thr Leu
            100                 105                 110

Gln Val Lys Val Ser Pro Thr Ser Val Pro Thr Thr Pro Arg Ala Thr
        115                 120                 125

Pro Ile Leu Gln Pro Arg Pro Gln Pro Gln Pro Gln Pro Gln Thr Gln
    130                 135                 140

Leu Gln Gln Gln Thr Val Met Ile Thr Pro Thr Phe Ser Thr Thr Pro
145                 150                 155                 160

Gln Thr Arg Ile Ile Gln Gln Pro Leu Ile Tyr Gln Asn Ala Ala Thr
                165                 170                 175

Ser Phe Gln Val Leu Gln Pro Gln Val Gln Ser Leu Val Thr Ser Ser
            180                 185                 190

Gln Val Gln Pro Val Thr Ile Gln Gln Gln Val Gln Thr Val Gln Ala
        195                 200                 205

Gln Arg Val Leu Thr Gln Thr Ala Asn Gly Thr Leu Gln Thr Leu Ala
    210                 215                 220

Pro Ala Thr Val Gln Thr Val Ala Ala Pro Gln Val Gln Gln Val Pro
225                 230                 235                 240

Val Leu Val Gln Pro Gln Ile Ile Lys Thr Asp Ser Leu Val Leu Thr
                245                 250                 255

Thr Leu Lys Thr Asp Gly Ser Pro Val Met Ala Ala Val Gln Asn Pro
            260                 265                 270

Ala Leu Thr Ala Leu Thr Thr Pro Ile Gln Thr Ala Ala Leu Gln Val
        275                 280                 285

Pro Thr Leu Val Gly Ser Ser Gly Thr Ile Leu Thr Thr Met Pro Val
    290                 295                 300

Met Met Gly Gln Glu Lys Val Pro Ile Lys Gln Val Pro Gly Gly Val
305                 310                 315                 320

Lys Gln Leu Glu Pro Pro Lys Glu Gly Glu Arg Arg Thr Thr His Asn
                325                 330                 335

Ile Ile Glu Lys Arg Tyr Arg Ser Ser Ile Asn Asp Lys Ile Ile Glu
            340                 345                 350

Leu Lys Asp Leu Val Met Gly Thr Asp Ala Lys Met His Lys Ser Gly
        355                 360                 365

Val Leu Arg Lys Ala Ile Asp Tyr Ile Lys Tyr Leu Gln Gln Val Asn
    370                 375                 380

His Lys Leu Arg Gln Glu Asn Met Val Leu Lys Leu Ala Asn Gln Lys
385                 390                 395                 400

Asn Lys Leu Leu Lys Gly Ile Asp Leu Gly Ser Leu Val Asp Asn Glu
                405                 410                 415

Val Asp Leu Lys Ile Glu Asp Phe Asn Gln Asn Val Leu Leu Met Ser
            420                 425                 430

Pro Pro Ala Ser Asp Ser Gly Ser Gln Ala Gly Phe Ser Pro Tyr Ser
        435                 440                 445
```

```
Ile Asp Ser Glu Pro Gly Ser Pro Leu Leu Asp Asp Ala Lys Val Lys
    450                 455                 460

Asp Glu Pro Asp Ser Pro Pro Val Ala Leu Gly Met Val Asp Arg Ser
465                 470                 475                 480

Arg Ile Leu Leu Cys Val Leu Thr Phe Leu Cys Leu Ser Phe Asn Pro
                485                 490                 495

Leu Thr Ser Leu Leu Gln Trp Gly Gly Ala His Asp Ser Asp Gln His
            500                 505                 510

Pro His Ser Gly Ser Gly Arg Ser Val Leu Ser Phe Glu Ser Gly Ser
        515                 520                 525

Gly Gly Trp Phe Asp Trp Met Met Pro Thr Leu Leu Leu Trp Leu Val
    530                 535                 540

Asn Gly Val Ile Val Leu Ser Val Phe Val Lys Leu Leu Val His Gly
545                 550                 555                 560

Glu Pro Val Ile Arg Pro His Ser Arg Ser Ser Val Thr Phe Trp Arg
                565                 570                 575

His Arg Lys Gln Ala Asp Leu Asp Leu Ala Arg Gly Asp Phe Ala Ala
            580                 585                 590

Ala Ala Ala Asn Leu Gln Thr Cys Leu Ala Val Leu Gly Arg Ala Leu
        595                 600                 605

Pro Thr Ser Arg Leu Asp Leu Ala Cys Ser Leu Ser Trp Asn Val Ile
    610                 615                 620

Arg Tyr Ser Leu Gln Lys Leu Arg Leu Val Arg Trp Leu Leu Lys Lys
625                 630                 635                 640

Val Phe Gln Cys Arg Arg Ala Thr Pro Ala Thr Glu Ala Gly Phe Glu
                645                 650                 655

Asp Glu Ala Lys Thr Ser Ala Arg Asp Ala Ala Leu Ala Tyr His Arg
            660                 665                 670

Leu His Gln Leu His Ile Thr Gly Lys Leu Pro Ala Gly Ser Ala Cys
        675                 680                 685

Ser Asp Val His Met Ala Leu Cys Ala Val Asn Leu Ala Glu Cys Ala
    690                 695                 700

Glu Glu Lys Ile Pro Pro Ser Thr Leu Val Glu Ile His Leu Thr Ala
705                 710                 715                 720

Ala Met Gly Leu Lys Thr Arg Cys Gly Gly Lys Leu Gly Phe Leu Ala
                725                 730                 735

Ser Tyr Phe Leu Ser Arg Ala Gln Ser Leu Cys Gly Pro Glu His Ser
            740                 745                 750

Ala Val Pro Asp Ser Leu Arg Trp Leu Cys His Pro Leu Gly Gln Lys
        755                 760                 765

Phe Phe Met Glu Arg Ser Trp Ser Val Lys Ser Ala Ala Lys Glu Ser
    770                 775                 780

Leu Tyr Cys Ala Gln Arg Asn Pro Ala Asp Pro Ile Ala Gln Val His
785                 790                 795                 800

Gln Ala Phe Cys Lys Asn Leu Leu Glu Arg Ala Ile Glu Ser Leu Val
                805                 810                 815

Lys Pro Gln Ala Lys Lys Lys Ala Gly Asp Gln Glu Glu Glu Ser Cys
            820                 825                 830

Glu Phe Ser Ser Ala Leu Glu Tyr Leu Lys Leu Leu His Ser Phe Val
        835                 840                 845

Asp Ser Val Gly Val Met Ser Pro Pro Leu Ser Arg Ser Ser Val Leu
    850                 855                 860

Lys Ser Ala Leu Gly Pro Asp Ile Ile Cys Arg Trp Trp Thr Ser Ala
865                 870                 875                 880
```

```
Ile Thr Val Ala Ile Ser Trp Leu Gln Gly Asp Asp Ala Ala Val Arg
                885                 890                 895

Ser His Phe Thr Lys Val Glu Arg Ile Pro Lys Ala Leu Glu Val Thr
            900                 905                 910

Glu Ser Pro Leu Val Lys Ala Ile Phe His Ala Cys Arg Ala Met His
        915                 920                 925

Ala Ser Leu Pro Gly Lys Ala Asp Gly Gln Gln Ser Ser Phe Cys His
    930                 935                 940

Cys Glu Arg Ala Ser Gly His Leu Trp Ser Ser Leu Asn Val Ser Gly
945                 950                 955                 960

Gly Thr Ser Asp Pro Ala Leu Asn His Val Val Gln Leu Leu Thr Cys
                965                 970                 975

Asp Leu Leu Leu Ser Leu Arg Thr Ala Leu Trp Gln Lys Gln Ala Ser
            980                 985                 990

Ala Ser Gln Ala Val Gly Glu Thr  Tyr His Ala Ser Gly  Ala Glu Leu
        995                 1000                1005

Ala Gly  Phe Gln Arg Asp Leu  Gly Ser Leu Arg Arg  Leu Ala His
    1010                1015                1020

Ser Phe  Arg Pro Ala Tyr Arg  Lys Val Phe Leu His  Glu Ala Thr
    1025                1030                1035

Val Arg  Leu Met Ala Gly Gly  Ser Pro Thr Arg Thr  His Gln Leu
    1040                1045                1050

Leu Glu  His Ser Leu Arg Arg  Arg Thr Thr Gln Ser  Thr Lys His
    1055                1060                1065

Gly Glu  Val Asp Ala Trp Pro  Gly Gln Arg Glu Arg  Ala Thr Ala
    1070                1075                1080

Ile Leu  Leu Ala Cys Arg His  Leu Pro Leu Ser Phe  Leu Ser Ser
    1085                1090                1095

Pro Gly  Gln Arg Ala Val Leu  Leu Ala Glu Ala Ala  Arg Thr Leu
    1100                1105                1110

Glu Lys  Val Gly Asp Arg Arg  Ser Cys Asn Asp Cys  Gln Gln Met
    1115                1120                1125

Ile Val  Lys Leu Gly Gly Gly  Thr Ala Ile Ala Ala  Ser
    1130                1135                1140
```